(12) United States Patent
Schmura et al.

(10) Patent No.: US 11,540,927 B2
(45) Date of Patent: *Jan. 3, 2023

(54) INTERVERTEBRAL IMPLANTS, SYSTEMS, AND METHODS OF USE

(71) Applicant: DePuy Synthes Products, Inc., Raynham, MA (US)

(72) Inventors: Kurt Schmura, Middleboro, MA (US); Edwin Chan, Woodbridge, NJ (US); Benjamin Chronister, Parkesburg, PA (US); Raymond Murphy, Manville, RI (US); Michael Jacene, Northbridge, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/876,292

(22) Filed: May 18, 2020

(65) Prior Publication Data

US 2020/0281740 A1    Sep. 10, 2020

Related U.S. Application Data

(63) Continuation of application No. 16/174,173, filed on Oct. 29, 2018, now Pat. No. 10,702,394, which is a
(Continued)

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4455* (2013.01); *A61F 2/4637* (2013.01);
(Continued)

(58) Field of Classification Search
CPC .......... A61F 2/44; A61F 2/4455; A61F 2/446; A61F 2/447; A61F 2/4637;
(Continued)

(56) References Cited

U.S. PATENT DOCUMENTS 424,836 A    4/1890 Thompson
438,892 A    10/1890 Lippy
(Continued)

FOREIGN PATENT DOCUMENTS

AU    2004232317 A1    11/2004
CA    2111598 A1    6/1994
(Continued)

OTHER PUBLICATIONS

Trial Transcript, United States District Court District of Delaware, Civil Action No. 1:11-cv-00652-LPS, Jun. 7, 2013, 97 pages.
(Continued)

*Primary Examiner* — Eric S Gibson
(74) *Attorney, Agent, or Firm* — BakerHostetler

(57) ABSTRACT

An intervertebral implant frame that is configured to engage a spacer can include a pair of arms that extend longitudinally from a support member such that the arms engage the spacer. The spacer can be made from bone graft, and include a first spacer body made of cortical bone, and a second spacer body made of cancellous bone.

18 Claims, 34 Drawing Sheets

Related U.S. Application Data continuation of application No. 15/992,464, filed on May 30, 2018, now Pat. No. 10,130,492, which is a continuation of application No. 15/704,308, filed on Sep. 14, 2017, now Pat. No. 10,010,432, which is a continuation of application No. 14/520,690, filed on Oct. 22, 2014, now Pat. No. 9,867,718.

(51) Int. Cl.
  *A61F 2/30* (2006.01)
  *A61B 17/86* (2006.01)

(52) U.S. Cl.
  CPC ............ H05K 999/99 (2013.01); *A61B 17/86* (2013.01); *A61F 2002/30057* (2013.01); *A61F 2002/30131* (2013.01); *A61F 2002/30433* (2013.01); *A61F 2002/30774* (2013.01); *A61F 2002/30787* (2013.01); *A61F 2002/30904* (2013.01); *A61F 2002/4628* (2013.01); *A61F 2310/00023* (2013.01); *A61F 2310/00359* (2013.01)

(58) Field of Classification Search
  CPC .... A61F 2002/30057; A61F 2002/4475; A61F 2002/4642
  USPC ............................................ 623/17.11–17.16
  See application file for complete search history.

(56) References Cited

U.S. PATENT DOCUMENTS

| | | |
|---|---|---|
| 1,105,105 A | 7/1914 | Sherman |
| 1,200,797 A | 10/1916 | Barbe |
| 2,151,919 A | 3/1939 | Jacobson |
| 2,372,888 A | 4/1945 | Duggan |
| 2,621,145 A | 12/1952 | Sano |
| 2,782,827 A | 2/1957 | Rosan |
| 2,906,311 A | 9/1959 | Boyd |
| 2,972,367 A | 2/1961 | Wootton |
| 3,062,253 A | 11/1962 | Miliheiser |
| 3,272,249 A | 9/1966 | Houston |
| 3,350,103 A | 10/1967 | Ahlstone |
| 3,426,364 A | 2/1969 | Lumb |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy et al. |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Kovaleva et al. |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Caspar et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz et al. |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker et al. |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,932,973 A | 6/1990 | Gendler |
| 4,936,851 A | 6/1990 | Fox et al. |
| 4,946,378 A | 8/1990 | Hirayama et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney et al. |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stengel |
| 5,020,949 A | 6/1991 | Davidson et al. |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Toermaelae et al. |
| 5,085,660 A | 2/1992 | Lin |
| 5,096,150 A | 3/1992 | Westwood |
| 5,108,438 A | 4/1992 | Stone |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,163,949 A | 11/1992 | Bonutti |
| 5,163,960 A | 11/1992 | Bonutti |
| 5,180,381 A | 1/1993 | Aust et al. |
| 5,192,327 A | 3/1993 | Brantigan |
| 5,197,971 A | 3/1993 | Bonutti |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stengel |
| 5,258,031 A | 11/1993 | Salib et al. |
| 5,269,785 A | 12/1993 | Bonutti |
| 5,275,601 A | 1/1994 | Gogolewski et al. |
| 5,281,226 A | 1/1994 | Davydov et al. |
| 5,282,861 A | 2/1994 | Kaplan |
| 5,284,655 A | 2/1994 | Bogdansky et al. |
| 5,290,312 A | 3/1994 | Kojimoto et al. |
| 5,295,994 A | 3/1994 | Bonutti |
| 5,298,254 A | 3/1994 | Prewett et al. |
| 5,304,021 A | 4/1994 | Oliver et al. |
| 5,306,307 A | 4/1994 | Senter et al. |
| 5,306,308 A | 4/1994 | Gross et al. |
| 5,306,309 A | 4/1994 | Wagner et al. |
| 5,314,476 A | 5/1994 | Prewett et al. |
| 5,314,477 A | 5/1994 | Marnay |
| 5,329,846 A | 7/1994 | Bonutti |
| 5,330,535 A | 7/1994 | Moser et al. |
| 5,331,975 A | 7/1994 | Bonutti |
| 5,345,927 A | 9/1994 | Bonutti |
| 5,348,788 A | 9/1994 | White |
| 5,368,593 A | 11/1994 | Stark |

(56) References Cited

U.S. PATENT DOCUMENTS

| | | |
|---|---|---|
| 5,380,323 A | 1/1995 | Howland |
| 5,385,583 A | 1/1995 | Cotrel |
| 5,397,364 A | 3/1995 | Kozak et al. |
| 5,403,317 A | 4/1995 | Bonutti |
| 5,403,348 A | 4/1995 | Bonutti |
| 5,405,391 A | 4/1995 | Henderson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,441,538 A | 8/1995 | Bonutti |
| 5,443,514 A | 8/1995 | Steffee |
| 5,443,515 A | 8/1995 | Cohen et al. |
| 5,454,365 A | 10/1995 | Bonutti |
| 5,458,638 A | 10/1995 | Kuslich et al. |
| 5,458,641 A | 10/1995 | Ramirez Jimenez |
| 5,458,643 A | 10/1995 | Oka et al. |
| 5,464,426 A | 11/1995 | Bonutti |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,496,348 A | 3/1996 | Bonutti |
| 5,507,818 A | 4/1996 | McLaughlin |
| 5,514,153 A | 5/1996 | Bonutti |
| 5,514,180 A | 5/1996 | Heggeness et al. |
| 5,520,690 A | 5/1996 | Errico et al. |
| 5,522,846 A | 6/1996 | Bonutti |
| 5,522,899 A | 6/1996 | Michelson |
| 5,527,343 A | 6/1996 | Bonutti |
| 5,531,746 A | 7/1996 | Errico et al. |
| 5,534,012 A | 7/1996 | Bonutti |
| 5,534,030 A | 7/1996 | Navarro et al. |
| 5,534,031 A | 7/1996 | Matsuzaki et al. |
| 5,534,032 A | 7/1996 | Hodorek |
| 5,545,222 A | 8/1996 | Bonutti |
| 5,545,842 A | 8/1996 | Balsells |
| 5,549,612 A | 8/1996 | Yapp et al. |
| 5,549,630 A | 8/1996 | Bonutti |
| 5,549,631 A | 8/1996 | Bonutti |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,305 A | 10/1996 | Bonutti |
| 5,569,308 A | 10/1996 | Sottosanti |
| 5,570,983 A | 11/1996 | Hollander |
| 5,571,109 A | 11/1996 | Bertagnoli |
| 5,571,190 A | 11/1996 | Ulrich et al. |
| 5,571,192 A | 11/1996 | Schonhoffer |
| 5,577,517 A | 11/1996 | Bonutti |
| 5,578,034 A | 11/1996 | Estes |
| 5,584,862 A | 12/1996 | Bonutti |
| 5,593,409 A | 1/1997 | Michelson |
| 5,593,425 A | 1/1997 | Bonutti et al. |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,620,448 A | 4/1997 | Puddu |
| 5,624,462 A | 4/1997 | Bonutti |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,662,710 A | 9/1997 | Bonutti |
| 5,667,520 A | 9/1997 | Bonutti |
| 5,669,909 A | 9/1997 | Zdeblick et al. |
| 5,674,296 A | 10/1997 | Bryan et al. |
| 5,676,666 A | 10/1997 | Oxland et al. |
| 5,676,699 A | 10/1997 | Gogolewski et al. |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,685,826 A | 11/1997 | Bonutti |
| 5,694,951 A | 12/1997 | Bonutti |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,707,390 A | 1/1998 | Bonutti |
| 5,713,899 A | 2/1998 | Marnay et al. |
| 5,713,900 A | 2/1998 | Benzel et al. |
| 5,716,325 A | 2/1998 | Bonutti |
| 5,725,531 A | 3/1998 | Shapiro |
| 5,725,588 A | 3/1998 | Errico et al. |
| 5,728,159 A * | 3/1998 | Stroever ............ A61F 2/28 623/23.5 |
| 5,733,306 A | 3/1998 | Bonutti |
| 5,735,853 A | 4/1998 | Olerud |
| 5,735,875 A | 4/1998 | Bonutti et al. |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,827,318 A | 10/1998 | Bonutti |
| 5,836,948 A | 11/1998 | Zucherman et al. |
| 5,845,645 A | 12/1998 | Bonutti |
| 5,860,973 A | 1/1999 | Michelson |
| 5,860,997 A | 1/1999 | Bonutti |
| 5,861,041 A * | 1/1999 | Tienboon ............ A61F 2/4455 606/279 |
| 5,865,845 A | 2/1999 | Thalgott |
| 5,865,849 A | 2/1999 | Stone |
| 5,872,915 A | 2/1999 | Dykes et al. |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,196 A | 3/1999 | Bonutti |
| 5,888,219 A | 3/1999 | Bonutti |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,928,267 A | 7/1999 | Bonutti et al. |
| 5,931,838 A | 8/1999 | Vito |
| 5,935,131 A | 8/1999 | Bonutti |
| 5,941,900 A | 8/1999 | Bonutti |
| 5,944,755 A | 8/1999 | Stone |
| 5,951,558 A | 9/1999 | Fiz |
| 5,954,722 A | 9/1999 | Bono |

(56) References Cited

U.S. PATENT DOCUMENTS

| | | |
|---|---|---|
| 5,954,739 A | 9/1999 | Bonutti |
| 5,958,314 A | 9/1999 | Draenert |
| 5,964,807 A | 10/1999 | Gan et al. |
| 5,968,098 A | 10/1999 | Winslow |
| 5,972,031 A | 10/1999 | Biedermann et al. |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,010,525 A | 1/2000 | Bonutti et al. |
| 6,013,853 A | 1/2000 | Athanasiou et al. |
| 6,017,305 A | 1/2000 | Bonutti |
| 6,017,345 A | 1/2000 | Richelsoph |
| 6,025,538 A * | 2/2000 | Yaccarino, III ...... A61L 27/3608 623/23.72 |
| 6,033,405 A | 3/2000 | Winslow et al. |
| 6,033,438 A | 3/2000 | Bianchi et al. |
| 6,039,762 A | 3/2000 | McKay |
| 6,042,596 A | 3/2000 | Bonutti |
| 6,045,579 A | 4/2000 | Hochschuler et al. |
| 6,045,580 A | 4/2000 | Scarborough et al. |
| 6,056,749 A | 5/2000 | Kuslich |
| 6,059,817 A | 5/2000 | Bonutti et al. |
| 6,066,175 A | 5/2000 | Henderson et al. |
| 6,077,292 A | 6/2000 | Bonutti |
| 6,080,158 A | 6/2000 | Lin |
| 6,080,193 A | 6/2000 | Hochschuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,102,928 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,132,472 A | 10/2000 | Bonutti |
| 6,136,001 A | 10/2000 | Michelson |
| 6,139,550 A | 10/2000 | Michelson |
| RE36,974 E | 11/2000 | Bonutti |
| 6,143,030 A | 11/2000 | Schroder |
| 6,143,033 A | 11/2000 | Paul et al. |
| 6,146,421 A | 11/2000 | Gordon et al. |
| 6,156,070 A | 12/2000 | Incavo et al. |
| 6,159,215 A | 12/2000 | Urbahns et al. |
| 6,159,234 A | 12/2000 | Bonutti et al. |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 * | 3/2001 | Anderson ............... A61L 27/14 623/16.11 |
| 6,203,565 B1 | 3/2001 | Bonutti et al. |
| 6,206,922 B1 | 3/2001 | Zdeblick et al. |
| 6,217,617 B1 | 4/2001 | Bonutti |
| 6,224,602 B1 | 5/2001 | Hayes |
| 6,231,592 B1 | 5/2001 | Bonutti et al. |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,277,136 B1 | 8/2001 | Bonutti |
| 6,287,325 B1 | 9/2001 | Bonutti |
| 6,306,139 B1 | 10/2001 | Fuentes |
| 6,322,562 B1 | 11/2001 | Wolter |
| 6,331,179 B1 | 12/2001 | Freid et al. |
| 6,342,074 B1 | 1/2002 | Simpson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti et al. |
| 6,371,986 B1 | 4/2002 | Bagby |
| 6,371,987 B1 | 4/2002 | Weiland et al. |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,443,987 B1 | 9/2002 | Bryan |
| 6,447,512 B1 | 9/2002 | Landry et al. |
| 6,447,516 B1 | 9/2002 | Bonutti |
| 6,447,546 B1 | 9/2002 | Bramlet et al. |
| 6,451,042 B1 | 9/2002 | Bonutti |
| 6,454,771 B1 | 9/2002 | Michelson |
| 6,458,158 B1 * | 10/2002 | Anderson ................ A61F 2/28 623/16.11 |
| 6,461,359 B1 | 10/2002 | Tribus et al. |
| 6,464,713 B2 | 10/2002 | Bonutti |
| 6,468,289 B1 | 10/2002 | Bonutti |
| 6,468,293 B2 | 10/2002 | Bonutti et al. |
| 6,468,311 B2 * | 10/2002 | Boyd ........................ A61F 2/28 623/17.11 |
| 6,471,724 B2 | 10/2002 | Zdeblick et al. |
| 6,475,230 B1 | 11/2002 | Bonutti et al. |
| 6,482,233 B1 | 11/2002 | Aebi et al. |
| 6,500,195 B2 | 12/2002 | Bonutti |
| 6,503,250 B2 | 1/2003 | Paul |
| 6,503,267 B2 | 1/2003 | Bonutti et al. |
| 6,503,277 B2 | 1/2003 | Bonutti |
| 6,511,509 B1 | 1/2003 | Ford et al. |
| 6,524,312 B2 | 2/2003 | Landry et al. |
| 6,543,455 B2 | 4/2003 | Bonutti |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,565,605 B2 | 5/2003 | Goble et al. |
| 6,569,187 B1 | 5/2003 | Bonutti et al. |
| 6,569,201 B2 | 5/2003 | Moumene et al. |
| 6,575,975 B2 | 6/2003 | Brace et al. |
| 6,575,982 B1 | 6/2003 | Bonutti |
| 6,576,017 B2 | 6/2003 | Foley et al. |
| 6,579,290 B1 | 6/2003 | Hardcastle et al. |
| 6,585,750 B2 | 7/2003 | Bonutti et al. |
| 6,592,531 B2 | 7/2003 | Bonutti |
| 6,592,609 B1 | 7/2003 | Bonutti |
| 6,592,624 B1 | 7/2003 | Fraser et al. |
| 6,602,291 B1 | 8/2003 | Ray et al. |
| 6,605,090 B1 | 8/2003 | Trieu et al. |
| 6,607,534 B2 | 8/2003 | Bonutti |
| 6,616,671 B2 | 9/2003 | Landry et al. |
| 6,620,163 B1 | 9/2003 | Michelson |
| 6,620,181 B1 | 9/2003 | Bonutti |
| 6,623,486 B1 | 9/2003 | Weaver et al. |
| 6,629,998 B1 | 10/2003 | Lin |
| 6,630,000 B1 | 10/2003 | Bonutti |
| 6,635,073 B2 | 10/2003 | Bonutti |
| 6,638,309 B2 | 10/2003 | Bonutti |

(56) References Cited

U.S. PATENT DOCUMENTS

| | | | |
|---|---|---|---|
| 6,638,310 B2 * | 10/2003 | Lin | A61F 2/28 623/17.11 |
| 6,645,212 B2 | 11/2003 | Goldhahn et al. | |
| 6,652,525 B1 | 11/2003 | Assaker et al. | |
| 6,652,532 B2 | 11/2003 | Bonutti | |
| 6,656,181 B2 | 12/2003 | Dixon et al. | |
| 6,679,887 B2 | 1/2004 | Nicholson et al. | |
| 6,682,561 B2 | 1/2004 | Songer et al. | |
| 6,682,563 B2 | 1/2004 | Scharf | |
| 6,695,846 B2 | 2/2004 | Richelsoph et al. | |
| 6,695,851 B2 | 2/2004 | Zdeblick et al. | |
| 6,702,821 B2 | 3/2004 | Bonutti | |
| 6,702,856 B2 | 3/2004 | Bonutti | |
| 6,706,067 B2 * | 3/2004 | Shimp | A61F 2/4455 623/17.11 |
| 6,709,456 B2 | 3/2004 | Langberg et al. | |
| 6,712,818 B1 | 3/2004 | Michelson | |
| 6,719,803 B2 | 4/2004 | Bonutti | |
| 6,730,127 B2 | 5/2004 | Michelson | |
| 6,736,850 B2 | 5/2004 | Davis | |
| 6,736,853 B2 | 5/2004 | Bonutti | |
| 6,743,257 B2 | 6/2004 | Castro | |
| 6,761,738 B1 * | 7/2004 | Boyd | A61F 2/4455 623/17.11 |
| 6,761,739 B2 * | 7/2004 | Shepard | A61F 2/28 623/23.61 |
| 6,770,078 B2 | 8/2004 | Bonutti | |
| 6,770,096 B2 | 8/2004 | Bolger et al. | |
| 6,776,938 B2 | 8/2004 | Bonutti | |
| 6,786,909 B1 | 9/2004 | Dransfeld et al. | |
| 6,800,092 B1 | 10/2004 | Williams et al. | |
| 6,800,093 B2 | 10/2004 | Nicholson et al. | |
| 6,805,714 B2 | 10/2004 | Sutcliffe | |
| 6,808,537 B2 | 10/2004 | Michelson | |
| 6,824,564 B2 | 11/2004 | Crozet | |
| 6,833,006 B2 | 12/2004 | Foley et al. | |
| 6,835,198 B2 | 12/2004 | Bonutti | |
| 6,837,905 B1 | 1/2005 | Lieberman | |
| 6,849,093 B2 | 2/2005 | Michelson | |
| 6,855,167 B2 * | 2/2005 | Shimp | A61F 2/28 623/17.11 |
| 6,855,168 B2 | 2/2005 | Crozet | |
| 6,860,885 B2 | 3/2005 | Bonutti | |
| 6,860,904 B2 | 3/2005 | Bonutti | |
| 6,863,673 B2 | 3/2005 | Gerbec et al. | |
| 6,872,915 B2 | 3/2005 | Koga et al. | |
| 6,884,242 B2 | 4/2005 | Lehuec et al. | |
| 6,890,334 B2 | 5/2005 | Brace et al. | |
| 6,896,701 B2 | 5/2005 | Boyd et al. | |
| 6,899,735 B2 | 5/2005 | Coates et al. | |
| 6,902,578 B1 * | 6/2005 | Anderson | A61L 27/3608 623/16.11 |
| 6,905,517 B2 | 6/2005 | Bonutti | |
| 6,908,466 B1 | 6/2005 | Bonutti et al. | |
| 6,916,320 B2 | 7/2005 | Michelson | |
| 6,923,756 B2 | 8/2005 | Sudakov et al. | |
| 6,932,835 B2 | 8/2005 | Bonutti et al. | |
| 6,953,477 B2 | 10/2005 | Berry | |
| 6,962,606 B2 | 11/2005 | Michelson | |
| 6,964,664 B2 | 11/2005 | Freid et al. | |
| 6,964,687 B1 | 11/2005 | Bernard et al. | |
| 6,972,019 B2 | 12/2005 | Michelson | |
| 6,972,035 B2 | 12/2005 | Michelson | |
| 6,974,479 B2 | 12/2005 | Trieu | |
| 6,984,234 B2 | 1/2006 | Bray | |
| 6,986,788 B2 * | 1/2006 | Paul | A61F 2/4455 623/17.11 |
| 6,989,029 B2 | 1/2006 | Bonutti | |
| 6,990,982 B1 | 1/2006 | Bonutti | |
| 7,001,385 B2 | 2/2006 | Bonutti | |
| 7,001,432 B2 | 2/2006 | Keller et al. | |
| 7,018,412 B2 * | 3/2006 | Ferreira | A61F 2/4455 606/247 |
| 7,018,416 B2 * | 3/2006 | Hanson | A61B 17/1671 623/17.16 |
| 7,033,394 B2 | 4/2006 | Michelson | |
| 7,041,135 B2 | 5/2006 | Michelson | |
| 7,044,968 B1 | 5/2006 | Yaccarino et al. | |
| 7,044,972 B2 | 5/2006 | Mathys et al. | |
| 7,048,755 B2 | 5/2006 | Bonutti et al. | |
| 7,048,765 B1 | 5/2006 | Grooms et al. | |
| 7,060,097 B2 | 6/2006 | Fraser et al. | |
| 7,066,961 B2 | 6/2006 | Michelson | |
| 7,070,557 B2 | 7/2006 | Bonutti | |
| 7,077,864 B2 | 7/2006 | Byrd et al. | |
| 7,087,073 B2 | 8/2006 | Bonutti | |
| 7,094,251 B2 | 8/2006 | Bonutti et al. | |
| 7,104,996 B2 | 9/2006 | Bonutti | |
| 7,112,223 B2 | 9/2006 | Davis | |
| 7,119,999 B2 | 9/2006 | Fraser et al. | |
| 7,114,500 B2 | 10/2006 | Bonutti | |
| 7,128,753 B1 | 10/2006 | Bonutti et al. | |
| 7,134,437 B2 | 11/2006 | Bonutti | |
| 7,135,024 B2 | 11/2006 | Cook et al. | |
| 7,135,043 B2 | 11/2006 | Nakahara et al. | |
| 7,137,984 B2 | 11/2006 | Michelson | |
| 7,147,652 B2 | 12/2006 | Bonutti et al. | |
| 7,147,665 B1 | 12/2006 | Bryan et al. | |
| 7,163,561 B2 | 1/2007 | Michelson | |
| 7,172,627 B2 | 2/2007 | Fiere et al. | |
| 7,172,672 B2 | 2/2007 | Silverbrook | |
| 7,208,013 B1 | 4/2007 | Bonutti | |
| 7,217,273 B2 | 5/2007 | Bonutti | |
| 7,217,290 B2 | 5/2007 | Bonutti | |
| 7,226,452 B2 | 6/2007 | Zubok | |
| 7,226,482 B2 * | 6/2007 | Messerli | A61F 2/28 623/17.11 |
| 7,232,463 B2 | 6/2007 | Falahee | |
| 7,232,464 B2 | 6/2007 | Mathieu et al. | |
| 7,238,203 B2 | 7/2007 | Bagga et al. | |
| 7,255,698 B2 | 8/2007 | Michelson | |
| 7,276,082 B2 | 10/2007 | Zdeblick et al. | |
| 7,311,719 B2 | 12/2007 | Bonutti | |
| 7,320,708 B1 | 1/2008 | Bernstein | |
| 7,323,011 B2 | 1/2008 | Shepard et al. | |
| 7,329,263 B2 | 2/2008 | Bonutti et al. | |
| 7,398,623 B2 | 7/2008 | Martel et al. | |
| 7,429,266 B2 | 9/2008 | Bonutti et al. | |
| 7,442,209 B2 | 10/2008 | Michelson | |
| 7,462,200 B2 | 12/2008 | Bonutti | |
| 7,481,831 B2 | 1/2009 | Bonutti | |
| 7,485,145 B2 | 2/2009 | Purcell | |
| 7,491,237 B2 * | 2/2009 | Randall | A61F 2/4611 623/17.11 |
| 7,510,557 B1 | 3/2009 | Bonutti | |
| 7,534,265 B1 | 5/2009 | Boyd et al. | |
| 7,594,932 B2 | 9/2009 | Aferzon et al. | |
| 7,601,173 B2 | 10/2009 | Messerli et al. | |
| 7,608,107 B2 | 10/2009 | Michelson | |
| 7,615,054 B1 | 11/2009 | Bonutti | |
| 7,618,456 B2 | 11/2009 | Mathieu et al. | |
| 7,621,960 B2 | 11/2009 | Boyd et al. | |
| 7,625,380 B2 | 12/2009 | Drewry et al. | |
| 7,635,390 B1 | 12/2009 | Bonutti | |
| 7,637,951 B2 | 12/2009 | Michelson | |
| 7,655,042 B2 | 2/2010 | Foley et al. | |
| 7,704,279 B2 | 4/2010 | Moskowitz et al. | |
| 7,708,740 B1 | 5/2010 | Bonutti | |
| 7,708,741 B1 | 5/2010 | Bonutti | |
| 7,727,283 B2 | 6/2010 | Bonutti | |
| 7,749,229 B1 | 7/2010 | Bonutti | |
| 7,776,067 B2 | 8/2010 | Jackson | |
| 7,780,670 B2 | 8/2010 | Bonutti | |
| 7,806,896 B1 | 10/2010 | Bonutti | |
| 7,806,897 B1 | 10/2010 | Bonutti | |
| 7,828,852 B2 | 11/2010 | Bonutti | |
| 7,833,271 B2 * | 11/2010 | Mitchell | A61F 2/447 623/17.11 |
| 7,837,736 B2 | 11/2010 | Bonutti | |
| 7,846,188 B2 | 12/2010 | Moskowitz et al. | |
| 7,846,207 B2 | 12/2010 | Lechmann et al. | |
| 7,854,750 B2 | 12/2010 | Bonutti et al. | |

(56) References Cited

U.S. PATENT DOCUMENTS

| | | | |
|---|---|---|---|
| 7,862,616 B2 | 1/2011 | Lechmann et al. | |
| 7,875,076 B2 | 1/2011 | Mathieu et al. | |
| 7,879,072 B2 | 2/2011 | Bonutti et al. | |
| 7,892,236 B1 | 2/2011 | Bonutti | |
| 7,892,261 B2 | 2/2011 | Bonutti | |
| 7,896,880 B2 | 3/2011 | Bonutti | |
| 7,931,690 B1 | 4/2011 | Bonutti | |
| 7,942,903 B2 | 5/2011 | Moskowitz et al. | |
| 7,959,635 B1 | 6/2011 | Bonutti | |
| 7,985,255 B2 | 7/2011 | Bray et al. | |
| 7,993,403 B2 | 8/2011 | Foley et al. | |
| 8,062,303 B2 | 11/2011 | Berry et al. | |
| 8,100,976 B2 | 1/2012 | Bray et al. | |
| 8,105,383 B2 | 1/2012 | Michelson | |
| 8,128,669 B2 | 3/2012 | Bonutti | |
| 8,128,700 B2 | 3/2012 | Delurio et al. | |
| 8,133,229 B1 | 3/2012 | Bonutti | |
| 8,162,977 B2 | 4/2012 | Bonutti et al. | |
| 8,182,532 B2 | 5/2012 | Anderson et al. | |
| 8,187,329 B2 | 5/2012 | Theofilos | |
| 8,211,148 B2 | 7/2012 | Zhang et al. | |
| 8,273,127 B2 | 9/2012 | Jones et al. | |
| 8,308,804 B2 | 11/2012 | Krueger | |
| 8,328,872 B2 | 12/2012 | Duffield et al. | |
| 8,343,220 B2 | 1/2013 | Michelson | |
| 8,343,222 B2 | 1/2013 | Cope | |
| 8,353,913 B2 | 1/2013 | Moskowitz et al. | |
| 8,382,768 B2 | 2/2013 | Berry et al. | |
| 8,425,522 B2 | 4/2013 | Bonutti | |
| 8,425,607 B2 | 4/2013 | Waugh et al. | |
| 8,444,696 B2 | 5/2013 | Michelson | |
| 8,465,546 B2 | 6/2013 | Jodaitis et al. | |
| 8,486,066 B2 | 7/2013 | Bonutti | |
| 8,540,774 B2 | 9/2013 | Kueenzi et al. | |
| 8,545,567 B1 | 10/2013 | Krueger | |
| 8,613,772 B2 | 12/2013 | Bray et al. | |
| 8,623,030 B2 | 1/2014 | Bonutti | |
| 8,632,552 B2 | 1/2014 | Bonutti | |
| 8,641,726 B2 | 2/2014 | Bonutti | |
| 8,641,743 B2 | 2/2014 | Michelson | |
| 8,641,768 B2 | 2/2014 | Duffield et al. | |
| 8,690,944 B2 | 4/2014 | Bonutti | |
| 8,739,797 B2 | 6/2014 | Bonutti | |
| 8,747,439 B2 | 6/2014 | Bonutti et al. | |
| 8,764,831 B2 | 7/2014 | Lechmann et al. | |
| 8,784,495 B2 | 7/2014 | Bonutti | |
| 8,795,363 B2 | 8/2014 | Bonutti | |
| 8,814,902 B2 | 8/2014 | Bonutti | |
| 8,834,490 B2 | 9/2014 | Bonutti | |
| 8,840,629 B2 | 9/2014 | Bonutti | |
| 8,845,699 B2 | 9/2014 | Bonutti | |
| 8,858,557 B2 | 10/2014 | Bonutti | |
| 8,956,417 B2 | 2/2015 | Bonutti | |
| 9,005,295 B2 | 4/2015 | Kueenzi et al. | |
| 9,044,322 B2 | 6/2015 | Bonutti | |
| 9,044,341 B2 | 6/2015 | Bonutti | |
| 9,050,152 B2 | 6/2015 | Bonutti | |
| 9,149,365 B2* | 10/2015 | Lawson | A61B 17/8042 |
| 9,192,419 B2 | 11/2015 | McDonough et al. | |
| 9,220,604 B2 | 12/2015 | McDonough et al. | |
| 9,241,809 B2 | 1/2016 | McDonough et al. | |
| 9,364,340 B2* | 6/2016 | Lawson | A61F 2/442 |
| 9,414,935 B2 | 8/2016 | McDonough et al. | |
| 9,463,097 B2 | 10/2016 | Lechmann et al. | |
| 9,572,681 B2 | 2/2017 | Mathieu et al. | |
| 9,744,049 B2 | 8/2017 | Kueenzi et al. | |
| 9,848,992 B2 | 12/2017 | McDonough et al. | |
| 9,867,718 B2* | 1/2018 | Schmura | H05K 999/99 |
| 9,883,950 B2 | 2/2018 | Bertagnoli et al. | |
| 10,010,432 B2* | 7/2018 | Schmura | A61F 2/447 |
| 10,130,492 B2* | 11/2018 | Schmura | A61F 2/4455 |
| 10,492,922 B2 | 12/2019 | Mathieu et al. | |
| 10,507,117 B2 | 12/2019 | McDonough et al. | |
| 10,702,394 B2* | 7/2020 | Schmura | A61F 2/447 |
| 2001/0001129 A1 | 5/2001 | McKay et al. | |
| 2001/0005796 A1 | 6/2001 | Zdeblick et al. | |
| 2001/0010021 A1 | 7/2001 | Boyd et al. | |
| 2001/0016777 A1 | 8/2001 | Biscup | |
| 2001/0020186 A1 | 9/2001 | Boyce et al. | |
| 2001/0023371 A1 | 9/2001 | Bonutti | |
| 2001/0031254 A1 | 10/2001 | Bianchi et al. | |
| 2001/0039456 A1* | 11/2001 | Boyer, II | A61F 2/28 623/23.63 |
| 2001/0041941 A1 | 11/2001 | Boyer et al. | |
| 2001/0049560 A1* | 12/2001 | Paul | A61F 2/28 623/17.11 |
| 2002/0004683 A1 | 1/2002 | Michelson | |
| 2002/0010511 A1 | 1/2002 | Michelson | |
| 2002/0016595 A1 | 2/2002 | Michelson | |
| 2002/0022843 A1 | 2/2002 | Michelson | |
| 2002/0029055 A1 | 3/2002 | Bonutti | |
| 2002/0029084 A1* | 3/2002 | Paul | A61F 2/44 623/925 |
| 2002/0040246 A1 | 4/2002 | Bonutti | |
| 2002/0049497 A1 | 4/2002 | Mason | |
| 2002/0065517 A1 | 5/2002 | Paul | |
| 2002/0077702 A1 | 6/2002 | Castro | |
| 2002/0082597 A1 | 6/2002 | Fraser | |
| 2002/0082603 A1 | 6/2002 | Dixon et al. | |
| 2002/0082803 A1 | 6/2002 | Schiffbauer | |
| 2002/0091447 A1 | 7/2002 | Shimp et al. | |
| 2002/0095155 A1 | 7/2002 | Michelson | |
| 2002/0095160 A1 | 7/2002 | Bonutti | |
| 2002/0099376 A1 | 7/2002 | Michelson | |
| 2002/0099378 A1 | 7/2002 | Michelson | |
| 2002/0099444 A1* | 7/2002 | Boyd | A61F 2/4455 623/23.76 |
| 2002/0995155 | 7/2002 | Michelson | |
| 2002/0106393 A1* | 8/2002 | Bianchi | A61L 27/3683 424/549 |
| 2002/0107571 A1 | 8/2002 | Foley | |
| 2002/0111680 A1 | 8/2002 | Michelson | |
| 2002/0128712 A1 | 9/2002 | Michelson | |
| 2002/0128717 A1 | 9/2002 | Alfaro et al. | |
| 2002/0147450 A1 | 10/2002 | Lehuec et al. | |
| 2002/0169508 A1 | 11/2002 | Songer et al. | |
| 2002/0161444 A1 | 12/2002 | Choi | |
| 2002/0193880 A1 | 12/2002 | Fraser | |
| 2003/0004576 A1 | 1/2003 | Thalgott | |
| 2003/0009147 A1 | 1/2003 | Bonutti | |
| 2003/0023260 A1 | 1/2003 | Bonutti | |
| 2003/0040798 A1 | 2/2003 | Michelson | |
| 2003/0045939 A1 | 3/2003 | Casutt | |
| 2003/0065396 A1 | 4/2003 | Michelson | |
| 2003/0078666 A1 | 4/2003 | Ralph et al. | |
| 2003/0078668 A1 | 4/2003 | Michelson | |
| 2003/0125739 A1 | 7/2003 | Bagga et al. | |
| 2003/0135277 A1 | 7/2003 | Bryan et al. | |
| 2003/0149484 A1 | 8/2003 | Michelson | |
| 2003/0153975 A1 | 8/2003 | Byrd et al. | |
| 2003/0167092 A1 | 9/2003 | Foley | |
| 2003/0181981 A1 | 9/2003 | Lemaire | |
| 2003/0195626 A1 | 10/2003 | Huppert | |
| 2003/0195632 A1 | 10/2003 | Foley et al. | |
| 2003/0199881 A1 | 10/2003 | Bonutti | |
| 2003/0199983 A1 | 10/2003 | Michelson | |
| 2004/0010287 A1 | 1/2004 | Bonutti | |
| 2004/0078078 A1* | 4/2004 | Shepard | A61F 2/447 623/17.11 |
| 2004/0078081 A1 | 4/2004 | Ferree | |
| 2004/0092929 A1 | 5/2004 | Zindrick | |
| 2004/0093084 A1 | 5/2004 | Michelson | |
| 2004/0097794 A1 | 5/2004 | Bonutti | |
| 2004/0098016 A1 | 5/2004 | Bonutti | |
| 2004/0102848 A1 | 5/2004 | Michelson | |
| 2004/0102850 A1* | 5/2004 | Shepard | A61F 2/28 623/17.16 |
| 2004/0126407 A1 | 7/2004 | Falahee | |
| 2004/0133278 A1 | 7/2004 | Marino et al. | |
| 2004/0138689 A1 | 7/2004 | Bonutti | |
| 2004/0138690 A1 | 7/2004 | Bonutti | |
| 2004/0143270 A1 | 7/2004 | Zucherman et al. | |
| 2004/0143285 A1 | 7/2004 | Bonutti | |
| 2004/0172033 A1 | 9/2004 | Bonutti | |

(56) References Cited

U.S. PATENT DOCUMENTS

| | | |
|---|---|---|
| 2004/0176853 A1 | 9/2004 | Sennett et al. |
| 2004/0193181 A1 | 9/2004 | Bonutti |
| 2004/0193269 A1 | 9/2004 | Fraser et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0220668 A1 | 11/2004 | Eisermann et al. |
| 2004/0230223 A1 | 11/2004 | Bonutti et al. |
| 2004/0249377 A1 | 12/2004 | Kaes et al. |
| 2004/0254644 A1 | 12/2004 | Taylor |
| 2004/0260427 A1 | 12/2004 | Wimsatt |
| 2005/0015149 A1 | 1/2005 | Michelson |
| 2005/0021042 A1 | 1/2005 | Marnay et al. |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1* | 3/2005 | Gross ............... A61F 2/28 623/17.11 |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0113918 A1* | 5/2005 | Messerli ............ A61F 2/28 623/17.11 |
| 2005/0113920 A1 | 5/2005 | Foley et al. |
| 2005/0125029 A1 | 6/2005 | Bernard et al. |
| 2005/0149193 A1 | 7/2005 | Zucherman et al. |
| 2005/0154391 A1 | 7/2005 | Doherty et al. |
| 2005/0159813 A1 | 7/2005 | Molz, IV |
| 2005/0159818 A1 | 7/2005 | Blain |
| 2005/0159819 A1 | 7/2005 | McCormack et al. |
| 2005/0171606 A1 | 8/2005 | Michelson |
| 2005/0171607 A1 | 8/2005 | Michelson |
| 2005/0177236 A1 | 8/2005 | Mathieu et al. |
| 2005/0216059 A1 | 9/2005 | Bonutti et al. |
| 2005/0222683 A1 | 10/2005 | Berry |
| 2005/0240267 A1* | 10/2005 | Randall ............. A61F 2/4611 623/17.11 |
| 2005/0240271 A1 | 10/2005 | Zubok et al. |
| 2005/0261767 A1 | 11/2005 | Anderson et al. |
| 2005/0267534 A1 | 12/2005 | Bonutti et al. |
| 2005/0283236 A1 | 12/2005 | Razian |
| 2006/0020342 A1* | 1/2006 | Ferree ............. A61B 17/8605 623/17.14 |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna et al. |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0167495 A1 | 7/2006 | Bonutti et al. |
| 2006/0195189 A1 | 8/2006 | Link et al. |
| 2006/0195193 A1 | 8/2006 | Bloemer |
| 2006/0206208 A1 | 9/2006 | Michelson |
| 2006/0229725 A1 | 10/2006 | Lechmann et al. |
| 2006/0235470 A1 | 10/2006 | Bonutti et al. |
| 2006/0265009 A1 | 11/2006 | Bonutti |
| 2007/0088358 A1 | 4/2007 | Yuan et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0177236 A1 | 8/2007 | Kijima et al. |
| 2007/0208378 A1 | 9/2007 | Bonutti et al. |
| 2007/0219365 A1 | 9/2007 | Joyce et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0039873 A1 | 2/2008 | Bonutti et al. |
| 2008/0047567 A1 | 2/2008 | Bonutti |
| 2008/0051890 A1 | 2/2008 | Waugh et al. |
| 2008/0058822 A1 | 3/2008 | Bonutti |
| 2008/0065140 A1 | 3/2008 | Bonutti |
| 2008/0082169 A1 | 4/2008 | Gittings et al. |
| 2008/0103519 A1 | 5/2008 | Bonutti |
| 2008/0108916 A1 | 5/2008 | Bonutti et al. |
| 2008/0114399 A1 | 5/2008 | Bonutti |
| 2008/0119933 A1 | 5/2008 | Aebi et al. |
| 2008/0132949 A1 | 6/2008 | Aferzon et al. |
| 2008/0133013 A1 | 6/2008 | Duggal et al. |
| 2008/0140116 A1 | 6/2008 | Bonutti |
| 2008/0140117 A1 | 6/2008 | Bonutti et al. |
| 2008/0161925 A1 | 7/2008 | Brittan et al. |
| 2008/0177307 A1* | 7/2008 | Moskowitz ............ A61F 2/447 606/301 |
| 2008/0188940 A1* | 8/2008 | Cohen .................. A61F 2/4465 623/17.16 |
| 2008/0200984 A1 | 8/2008 | Jodaitis et al. |
| 2008/0206297 A1 | 8/2008 | Roeder et al. |
| 2008/0234822 A1* | 9/2008 | Govil .................. A61F 2/3094 623/17.16 |
| 2008/0249569 A1 | 10/2008 | Waugh et al. |
| 2008/0249575 A1 | 10/2008 | Waugh et al. |
| 2008/0249622 A1* | 10/2008 | Gray .................. A61F 2/4455 606/86 A |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0281425 A1* | 11/2008 | Thalgott ................ A61F 2/447 623/17.16 |
| 2008/0306596 A1 | 12/2008 | Jones et al. |
| 2008/0312742 A1 | 12/2008 | Abernathie |
| 2009/0076608 A1 | 3/2009 | Gordon et al. |
| 2009/0088849 A1* | 4/2009 | Armstrong ........... A61F 2/4455 623/17.16 |
| 2009/0099601 A1 | 4/2009 | Aferzon et al. |
| 2009/0099661 A1* | 4/2009 | Bhattacharya ........ A61F 2/4455 623/17.11 |
| 2009/0105830 A1 | 4/2009 | Jones et al. |
| 2009/0132051 A1 | 5/2009 | Moskowitz et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2010/0305704 A1* | 12/2010 | Messerli ................ A61F 2/442 623/17.16 |
| 2010/0312346 A1 | 12/2010 | Kueenzi et al. |
| 2011/0087327 A1 | 4/2011 | Lechmann et al. |
| 2011/0118843 A1 | 5/2011 | Mathieu et al. |
| 2011/0137417 A1* | 6/2011 | Lee .................... A61F 2/4455 623/16.11 |
| 2011/0166660 A1 | 7/2011 | Laurence |
| 2011/0230971 A1* | 9/2011 | Donner .................. A61F 2/442 606/246 |
| 2011/0238184 A1 | 9/2011 | Zdeblick et al. |
| 2011/0295371 A1 | 12/2011 | Moskowitz et al. |
| 2012/0010623 A1 | 1/2012 | Bonutti |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1* | 7/2012 | McDonough ...... A61B 17/1757 623/17.16 |
| 2012/0197401 A1* | 8/2012 | Duncan ................ A61F 2/442 29/428 |

(56) References Cited

U.S. PATENT DOCUMENTS

| | | | |
|---|---|---|---|
| 2012/0215226 A1 | 8/2012 | Bonutti | |
| 2012/0215233 A1 | 8/2012 | Bonutti et al. | |
| 2012/0221017 A1 | 8/2012 | Bonutti | |
| 2012/0323330 A1* | 12/2012 | Kueenzi | A61F 2/4455 623/17.16 |
| 2013/0073046 A1 | 3/2013 | Zaveloff et al. | |
| 2013/0073047 A1* | 3/2013 | Laskowitz | A61F 2/447 623/17.16 |
| 2013/0166032 A1* | 6/2013 | McDonough | A61F 2/4455 623/17.16 |
| 2013/0173013 A1 | 7/2013 | Anderson et al. | |
| 2013/0226185 A1 | 8/2013 | Bonutti | |
| 2013/0237989 A1 | 9/2013 | Bonutti | |
| 2013/0268008 A1 | 10/2013 | McDonough et al. | |
| 2013/0289729 A1 | 10/2013 | Bonutti | |
| 2014/0018854 A1 | 1/2014 | Bonutti et al. | |
| 2014/0025110 A1 | 1/2014 | Bonutti et al. | |
| 2014/0025111 A1 | 1/2014 | Bonutti et al. | |
| 2014/0025112 A1 | 1/2014 | Bonutti | |
| 2014/0025168 A1* | 1/2014 | Klimek | A61F 2/4455 623/17.16 |
| 2014/0081406 A1 | 3/2014 | Kellar et al. | |
| 2014/0100663 A1 | 4/2014 | Messerli et al. | |
| 2014/0121777 A1* | 5/2014 | Rosen | A61F 2/4455 623/17.16 |
| 2014/0180422 A1* | 6/2014 | Klimek | A61F 2/30744 623/17.16 |
| 2014/0214166 A1* | 7/2014 | Theofilos | A61F 2/4455 623/17.16 |
| 2014/0228963 A1 | 8/2014 | Bonutti | |
| 2014/0243985 A1 | 8/2014 | Lechmann et al. | |
| 2014/0257380 A1 | 9/2014 | Bonutti | |
| 2014/0257487 A1 | 9/2014 | Lawson et al. | |
| 2014/0277456 A1* | 9/2014 | Kirschman | A61F 2/4455 623/17.11 |
| 2014/0309560 A1 | 10/2014 | Bonutti | |
| 2014/0336770 A1 | 11/2014 | Petersheim et al. | |
| 2014/0343573 A1 | 11/2014 | Bonutti | |
| 2014/0371859 A1 | 12/2014 | Petersheim et al. | |
| 2015/0257893 A1* | 9/2015 | Mazzuca | A61F 2/4455 623/17.16 |
| 2015/0320571 A1 | 11/2015 | Lechmann et al. | |
| 2016/0113774 A1* | 4/2016 | Schmura | A61F 2/447 623/17.16 |
| 2018/0000607 A1* | 1/2018 | Schmura | A61F 2/4637 |
| 2018/0271672 A1* | 9/2018 | Schmura | A61F 2/4455 |
| 2019/0060082 A1* | 2/2019 | Schmura | A61F 2/4637 |
| 2020/0281740 A1* | 9/2020 | Schmura | H05K 999/99 |

FOREIGN PATENT DOCUMENTS

| | | |
|---|---|---|
| CA | 2317791 A1 | 8/1999 |
| CN | 1383790 A | 12/2002 |
| CN | 1620271 A | 5/2005 |
| CN | 1701772 A | 11/2005 |
| CN | 1901853 A | 1/2007 |
| DE | 2821678 A | 11/1979 |
| DE | 3042003 A1 | 7/1982 |
| DE | 3933459 A1 | 4/1991 |
| DE | 4242889 A1 | 6/1994 |
| DE | 4409392 A1 | 9/1995 |
| DE | 4423257 A1 | 1/1996 |
| DE | 19504867 C1 | 2/1996 |
| DE | 29913200 U1 | 9/1999 |
| DE | 202004020209 U1 | 5/2006 |
| EP | 0179695 A1 | 4/1986 |
| EP | 0298233 A1 | 1/1989 |
| EP | 0302719 A1 | 2/1989 |
| EP | 0505634 A1 | 9/1992 |
| EP | 0577178 A1 | 1/1994 |
| EP | 0639351 A2 | 2/1995 |
| EP | 0425542 B1 | 3/1995 |
| EP | 0504346 B1 | 5/1995 |
| EP | 0517030 B1 | 9/1996 |
| EP | 0897697 A1 | 2/1999 |
| EP | 0605799 B1 | 4/1999 |
| EP | 0641547 B1 | 5/1999 |
| EP | 0966930 A1 | 12/1999 |
| EP | 0968692 A1 | 1/2000 |
| EP | 0974319 A2 | 1/2000 |
| EP | 1124512 A1 | 8/2001 |
| EP | 1194087 A1 | 4/2002 |
| EP | 1393689 A2 | 3/2004 |
| EP | 1402836 A2 | 3/2004 |
| EP | 1033941 B1 | 8/2004 |
| EP | 0906065 B1 | 9/2004 |
| EP | 1051133 B1 | 10/2004 |
| EP | 1103236 B1 | 8/2006 |
| EP | 1459711 B1 | 7/2007 |
| EP | 1847240 A1 | 10/2007 |
| FR | 2552659 A3 | 4/1985 |
| FR | 2697996 A1 | 5/1994 |
| FR | 2700947 A1 | 8/1994 |
| FR | 2703580 A1 | 10/1994 |
| FR | 2727003 A1 | 5/1996 |
| FR | 2747034 A1 | 10/1997 |
| FR | 2753368 A1 | 3/1998 |
| GB | 0157668 A | 1/1921 |
| GB | 0265592 A | 8/1927 |
| GB | 2148122 A | 5/1985 |
| GB | 2207607 A | 2/1989 |
| GB | 2239482 A | 7/1991 |
| GB | 2266246 A | 10/1993 |
| JP | 03-505416 A | 11/1991 |
| JP | 09-280219 A | 10/1997 |
| JP | 2006-513752 A | 4/2006 |
| MX | 9601079 A | 7/1997 |
| RU | 2229271 C1 | 5/2004 |
| RU | 2244527 C2 | 1/2005 |
| RU | 2307625 C1 | 10/2007 |
| SU | 1465040 A1 | 3/1989 |
| WO | 88/03417 A1 | 5/1988 |
| WO | 88/10100 A1 | 12/1988 |
| WO | 89/09035 A1 | 10/1989 |
| WO | 90/00037 A1 | 1/1990 |
| WO | 92/01428 A1 | 2/1992 |
| WO | 92/06005 A1 | 4/1992 |
| WO | 93/01771 A1 | 2/1993 |
| WO | 95/08964 A2 | 4/1995 |
| WO | 95/15133 A1 | 6/1995 |
| WO | 95/20370 A1 | 8/1995 |
| WO | 95/21053 A1 | 8/1995 |
| WO | 95/26164 A1 | 10/1995 |
| WO | 96/39988 A2 | 12/1996 |
| WO | 96/40015 A1 | 12/1996 |
| WO | 97/20526 A1 | 6/1997 |
| WO | 97/23175 A1 | 7/1997 |
| WO | 97/25941 A1 | 7/1997 |
| WO | 97/25945 A1 | 7/1997 |
| WO | 97/37620 A1 | 10/1997 |
| WO | 97/39693 A1 | 10/1997 |
| WO | 98/17208 A2 | 4/1998 |
| WO | 98/17209 A2 | 4/1998 |
| WO | 98/55052 A1 | 12/1998 |
| WO | 98/56319 A1 | 12/1998 |
| WO | 98/56433 A1 | 12/1998 |
| WO | 99/09896 A1 | 3/1999 |
| WO | 99/09903 A1 | 3/1999 |
| WO | 99/27864 A2 | 6/1999 |
| WO | 99/29271 A1 | 6/1999 |
| WO | 99/32055 A1 | 7/1999 |
| WO | 99/38461 A2 | 8/1999 |
| WO | 99/38463 A2 | 8/1999 |
| WO | 99/56675 A1 | 11/1999 |
| WO | 99/63914 A1 | 12/1999 |
| WO | 00/07527 A1 | 2/2000 |
| WO | 00/07528 A1 | 2/2000 |
| WO | 00/25706 | 5/2000 |
| WO | 00/30568 A1 | 6/2000 |
| WO | 00/40177 A1 | 7/2000 |
| WO | 00/41654 A2 | 7/2000 |
| WO | 00/59412 A1 | 10/2000 |
| WO | 00/66044 A1 | 11/2000 |

(56) References Cited

FOREIGN PATENT DOCUMENTS

| WO | 00/66045 A1 | 11/2000 |
|---|---|---|
| WO | 00/74607 A1 | 12/2000 |
| WO | 01/03615 A1 | 1/2001 |
| WO | 01/08611 A1 | 2/2001 |
| WO | 01/56497 A2 | 8/2001 |
| WO | 01/62190 A1 | 8/2001 |
| WO | 01/80785 A1 | 11/2001 |
| WO | 01/93742 A2 | 12/2001 |
| WO | 01/95837 A1 | 12/2001 |
| WO | 2004/000177 A1 | 12/2003 |
| WO | 2004/069106 A1 | 8/2004 |
| WO | 2005/007040 A1 | 1/2005 |
| WO | 2005/020861 A1 | 3/2005 |
| WO | 2006/138500 A2 | 12/2006 |
| WO | 07/98288 A2 | 8/2007 |
| WO | 2008/014258 A2 | 1/2008 |
| WO | 2008/082473 A1 | 7/2008 |
| WO | 2008/102174 A2 | 8/2008 |
| WO | 2008/124355 A1 | 10/2008 |
| WO | 2008/154326 A1 | 12/2008 |
| WO | 2009/064644 A1 | 5/2009 |
| WO | 2009/158319 A1 | 12/2009 |
| WO | 2010/054181 A1 | 5/2010 |
| WO | 2010/054208 A1 | 5/2010 |
| WO | 2012/088238 A2 | 6/2012 |

OTHER PUBLICATIONS

U.S. Appl. No. 11/199,599: Final Rejection, dated Dec. 24, 2009, 21 pages.
U.S. Appl. No. 11/199,599: Non-Final Rejection, dated Apr. 1, 2009, 20 pages.
U.S. Provisional Application Filed on Dec. 19, 1997 by Urbahns et al., entitled "Insertion Instruments and Method for Delivering a Vertebral Body Spacer", U.S. Appl. No. 60/068,205.
U.S. Provisional Application Filed on Jan. 15, 1998 by David J. Urbahns et al., entitled "Insertion Instruments and Method for Delivering a Vertebral Body Spacer", U.S. Appl. No. 60/071,527.
U.S.Provisional Application filed on Nov. 16, 2007 by Thomas Kueenzi et al., entitled "Low profile intervertebral inplant", U.S. Appl. No. 60/988,661.
U.S. Appl. No. 11/199,599: Amendment dated Sep. 29, 2009, 30 pages.
U.S. Appl. No. 11/199,599: Appeal Brief dated Apr. 15, 2010, 51 pages.
U.S. Appl. No. 11/199,599: Interview Summary including Draft Claim Amendments dated Sep. 24, 2009, 16 pages.
U.S. Appl. No. 11/199,599: Preliminary Amendment dated Jan. 9, 2008,11 pages.
Verbiest H., La Chirurgie Anterieure et Laterale du Rachis Cervical,16(S2) Neurochirurgie 1-212; 1970 (w/Translation).
Wang, Determination of Cortical Bone Porosity and Pore Size Distribution using a Low Field Pulsed NMR Approach, J. Orthop Res., Mar.; 21(2):312—Mar. 9, 2003.
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discetomy without Bone Graft, 47(4) J. Neurosurg. 551-555, Oct. 1977.
Written Opinion, dated Mar. 20, 2009, for PCT International Application No. PCT/US08/82473, filed Nov. 5, 2008.
Younger, Morbidity at Bone Graft Donor Sites, 3(3) J. Orth. Trauma, 192-195, 1989.
"Expert Report of John F. Hall, M.D.", United States District Court for the District of Delaware, Civil Action No. 1:11-cv-00652-LPS, Dec. 14, 2012, 27 pages.
"Expert Report of Paul Ducheyne, Ph.D. Concerning Patent Validity", United States District Court District of Delaware, Civil Action No. 1:11-cv-00652-LPS, Dec. 13, 2012, 155 pages.
"Expert Report of Richard J. Gering, Ph.D., CLP" In the United States District Court for the District of Delaware, Civil Action No. 1:11-cv-00652-LPS, Dec. 14, 2012, 39 pages.
"Reply Report of Dr. Domagoj Coric Regarding the Invalidity of U.S. Pat. Nos. 7,846,207, 7,862,616 and 7,875,076", In the United States District Court for the District of Delaware, Civil Action No. 1:11-cv-00652-LPS, Jan. 4, 2013, 81 pages.
AcroMed Carbon Fiber Interbody Fusion Devices; Jan. 1998, 8 pages.
Al-Sanabani, Application of Calcium Phosphate Materials in Dentistry, vol. 2013, Int. J. Biomaterials, 1-12, 2013.
Appendix 1 to Joint Claim Construction Brief,A- Synthes' Exhibits A-9, In the United States District Court for the District of Delaware Civil Action No. 1 :11-cv-00652-LPS, Jun. 8, 2012,192 pages.
Appendix 2 to Joint Claim Construction Brief, Globus' Exhibits A-F, In the United States District Court for the District of Delaware Civil Action No. 1 :11-cv-00652-LPS, Jun. 8, 2012, 146 pages.
Appendix 3 to Joint Claim Construction Brief, Exhibits A-C, In the United States District Court for the District of Delaware Civil Action No. 1:11-cv-00652-LPS, Jun. 8, 2012, 38 pages.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20 (9) Spine 1055-1060, May 1995.
Benezech, L'arthrodese Cervicale ParVoie Anterieurea L'Aide de Plaque-Cage P.C.B., 3(1) Rach is 1,47,1997 (w/ Translation).
Brantigan 1/F Cage for PLIF Surgical Technique Guide; Apr. 1991, 22 pages.
Brantigan, A Carbon Fiber Implant to Aid Interbody Lumbar Fusion, 16(6S) Spine S277-S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion,Chapter 27, posterior Lumbar Interbody Fusion Using the Lumber Interbody Fusion p. 437-466, 2006.
Brantigan, Pseudarthrosis Rate After Allograft Posterior Lumbar Interbody Fusion with Pedicle Screw and Plate Fixation, 19(11) Spine 1270-1280, Jun. 1994.
Bray, "InterPlate Spine Fusion Device: Subsidence Control Without Stress Shielding", Orthopaedic Product News, Sep./Oct. 2006, pp. 22-25.
Bray, InterPlate Vertebral Body Replacement; website accessed May 4, 2017; http://rsbspine.com/Products.aspx, 2 pages.
Carbon Fiber Composite Ramps for Lumbar Interbody Fusion; Apr. 1997, 2 pages.
Chadwick et al., "Radiolucent Structural Materials For Medical Application", www.mddionline.com/print/238,, Jun. 2001, accessed Jul. 31, 2012, 9 pages.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 302-617, 1958.
Dabrowski, Highly Porous Titanium Scaffolds for Orthopaedic Applications, J. Biomed Mater. Res. B. Appl. Biomat. Oct.;95(1):53-61, 2010.
Delecrin, Morbidite du Prelevement de Greffons osseuz au Niveau des Creh'.iS lliaques dans la Chirurgie Du Rachis; justification du recours aux substituts osseuz, 13(3) Rachis 167-174,2001 (w/Translation).
DePuy Motech Surgical Titanium Mesh Brochure; 1998, 13 pages.
Dereymaeker, Nouvelle Cure neuro-Chirurgicale de discopathies Cervicales, 2 vleurochimrgie 226-234; 1956 (w/Translation).

(56) References Cited

OTHER PUBLICATIONS

Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Expert Report of Dr. Domagoj Carie Regarding the Invalidity of U.S. Pat. Nos. 7,846,207, 7,862,616 and 7,875,076, In the United States District Court for the District of Delaware, Civil Action No. 1:11-cv-00652-LPS, Nov. 5, 2012, 149 pages.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. 1. Ortho. 895-904, Dec. 1995.
Fuentes, Les Complications de la Chirurgie Par Voie Anlerieure du Rachis Cervical, 8(1) Rachis 3-14, 1996 (w/translation).
Germay, Resultats Cliniques de Ceramiques D'hydroxyapatite dans les arthrodeses Inter-somatiques du Rachis Dervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
International Patent Application No. PCT/CH2003/00089, International Search Report, dated Dec. 3, 2003, 3 pages.
International Patent Application No. PCT/US2011/066421; International Search Report and Written Opinion dated Jun. 14, 2012, 31 pages.
International Patent Application No. PCT/CH2003/00089, International Search Report dated Dec. 2, 2003, 3 Pages.
International Search Report, completed Aug. 16, 2007 for International Application No. PCT/US2007/005098, filed Feb. 27, 2007, 5 pgs.
International Search Report, dated Mar. 20, 2009, for PCT International Application No. PCT/US08/82473, filed Nov. 5, 2008.
Japanese Patent Application No. 2011-534926: Office Action dated Oct. 30, 2013, 7 pages.
Japanese Patent Application No. 2011-534928: Office Action dated Sep. 30, 2013, 11 pages.
Joint Claim Construction Brief, In the United States District Court for the District of Delaware, Civil Action No. 1:11-;,v-00652-LPS, Jun. 14, 2012, 97 pages.
Jonbergen et al., "Anterior CervicalInterbody fusion with a titanium box cage: Early radiological assessment of fusion and subsidence", The Spine Journal 5, Jul. 2005, 645-649.
Jost, Compressive Strength of Interbody Cages in the Lumbar Spine: the Effect of Cage Shape, Posterior Instrumentation and Bone Density, 7 Eur. Spine J. 132-141, 1998.
Jury Trial Demanded, In the United States District Court for the District of Delaware, Case No. 1:11-cv-00652-LPS, filed Jul. 22, 2011,8 pages.
Jury Verdict Form, United States District Court District of Delaware, Civil Action No. 1:11-cv-00652-LPS, Jun. 14, 2013, 20 pages.
Kastner, Advanced X-Ray Tomographic Methods for Quantitative Charecterisation of Barbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No. 300, Clin. Orth. Rel. Res., 45-51, 1994.
Kroppenstedt, Radiological Comparison of Instrumented Posterior Lumbar Interbody Fusion with One or Two Closed-Sox Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci., 4033-4065, 2009.
Malca, Cervical Interbody Xenografl with Plate Fixation, 21 (6) Spine, 685-690, Mar. 1996.
Marcolongo et al., "Trends in Materials for Spine Surgery", Comprehensive Biomaterials, Biomaterials and Clinical Use, 6.610, Oct. 2011, 21 pages.
McAfee, Minimally Invasive Anterior Retroperitoneal Approach to the Lumbar Spine, 21(13) Spine, 1476-1484, 1998.
Memorandum Opinion, United States District Court District of Delaware, Civil Action No. 1:11-cv-00652-LPS, May 7, 2013, 33 pages.
Nasca, Newer Lumbar Interbody Fusion Techniques, 22(2) J. Surg. Ortho. Advances, 113-117, 2013.
Order, United States District Court District of Delaware, Civil Action No. 1:11-cv-00652-LPS, May 15, 2013, 4 pages.
Order, United States District Court District of Delaware, Civil Action No. 1:11-cv-00652-LPS, May 7, 2013, 7 pages.
Pavlov et al., Anterior Lumbar Interbody Fusion with Threaded Fusion Cages and Autologous Grafts, Eur. Spine J., 2000, 9, 224-229.
PCB EVOLUTION Surgical Technique Guide 2010.
PCT International Application No. PCT/US2009/063529: International Search Report and Written Opinion dated Apr. 14, 2010, 19 pages.
Plaintiffs' Responses and Objections to Defendant Globus Medical, Inc.'s First Set of Interrogatories (Nos. 1-11), United States District Court for the District of Delaware, Civil Action No. 1:11-cv-00652-LPS, Nov. 14, 2011, 18 pages.
Plaintiffs' Supplemental Responses and Objections to Defendant Globus Medical Inc.'s Interrogatories Nos. 6-10 and Second Supplemental Responses and Objections to Interrogatory No. 5, United States District Court for the District of Delaware, Civil Action No. 11-cv-652-LPS, Sep. 1, 2012, 12 pages.
Polysciences Inc. Info Sheet 2012.
Porex Website, http://www.porex.com/technologies/materials/porous-plastics, Porous Elastic Materials, accessed Aug. 21, 2015, 2 pages.
Redacted version of "Defendant Globus Medical, Inc.'s Answering Brief in Opposition to Plaintiffs Motion for Summary Judgment of No. Anticipation by the Kozak and Michelson References", Mar. 12, 2013, 233 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Plaintiffs Reply Brief in Support of Plainiirrs Motion for Summary Judgment of No Anticipation by the Kozak and Michelson References", Mar. 21, 2013, 11pages.
Reply Report of Dr. Domagoj Carie Regarding the Invalidity of U.S. Patent Nos. 7,846,207,7,862,616 and 7,875,076, In the United States District Court for the District of Delaware,Civil Action No. 1:11-cv-00652-LPS, Jan. 4, 2013, 81 pages.
Russian Patent Application No. 2011-1122797: Decision to Grant dated Oct. 9, 2013, 20 pages.
Samandouras, A New Anterior Cervical Instrumentation System Combinin an Intradiscal Cage with an Integrated plate, 26(10) Spine, 1188-1192, 2001.
Schleicher et al., "Biomechanical Comparison of Two Different Concepts for Stand alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Second Expert Report of Wilson C. Hayes, Ph.D., United States District Court for the District of Delaware, Civil Action No. 1:11-cv-00652-LPS, Dec. 14, 2012, 22 pages.
Sonntag, Controversy in Spine Care, Is Fusion Necessary Arter Anterior Cervical Discectomy 21(9) Spine, 1111-1113, May 1996.

(56) References Cited

OTHER PUBLICATIONS

Spruit et al., "The in Vitro Stabilizing Effect of Polyetheretherketone Cages Versus a Titanium Cage of similar design for anterior lumbar interbody fusion", Eur. Spine J., Aug. 2005, 14 752-758.
Synthes History and Evolution of LBIF Brochure; Nov. 2015, 30 pages.
Synthes Spine Cervical Stand-Alone Devices Presentation Brochure; 2010, 40 pages.
Synthes Spine, "CorticoCancellous ACF Spacer. An allograft space or anterior fusion of the cervical spine," brochure, Musculoskeletal Transplant Foundationm, 2003, 6 pages.
Synthes Spine, "SynFix-LR System. Instruments and Implants for Stand-Alone Anterior Lumbar Interbody Fusion ALIF)", Technique Guide dated 2008, pp. 2010, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Synthes SynFix-LR System Technique Guide dated 2008.
Synthes Zero-P Instruments and Implants Technique Guide dated 2008.
Takahama, A New Improved Biodegradable Tracheal Prosthesis Using Hydroxy Apatite and Barbon Fiber 35(3) ASAIO Trans, 291-293, Jul.-Sep. 1989.
Tamariz, Biodegradation of Medical Purpose Polymeric Materials and Their Impacton Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.
Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 30 pages.

* cited by examiner

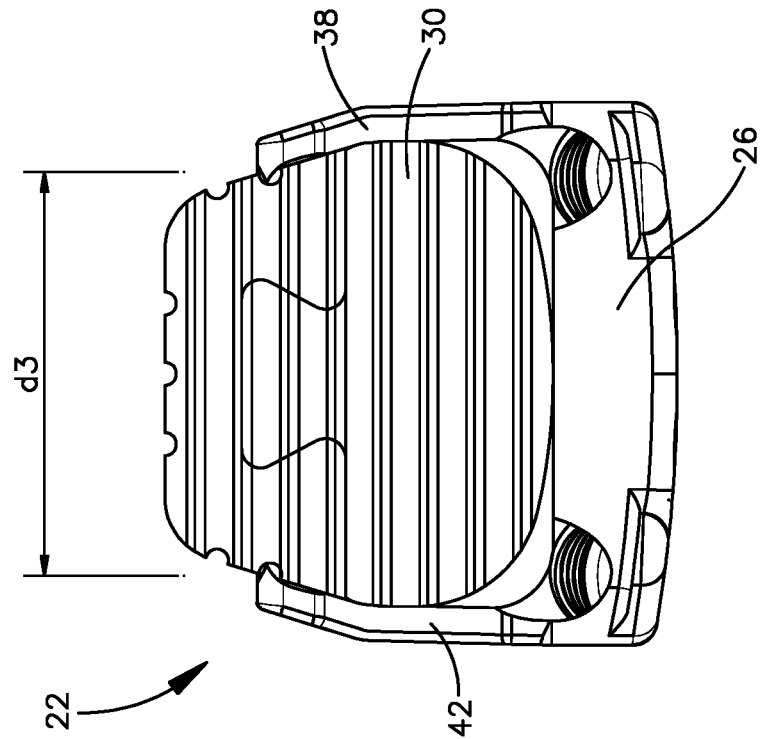
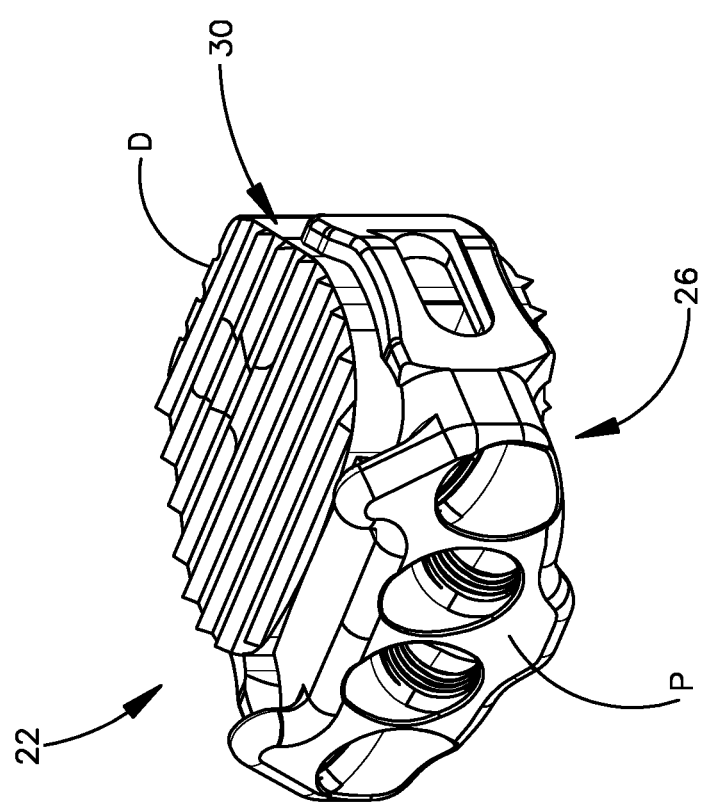

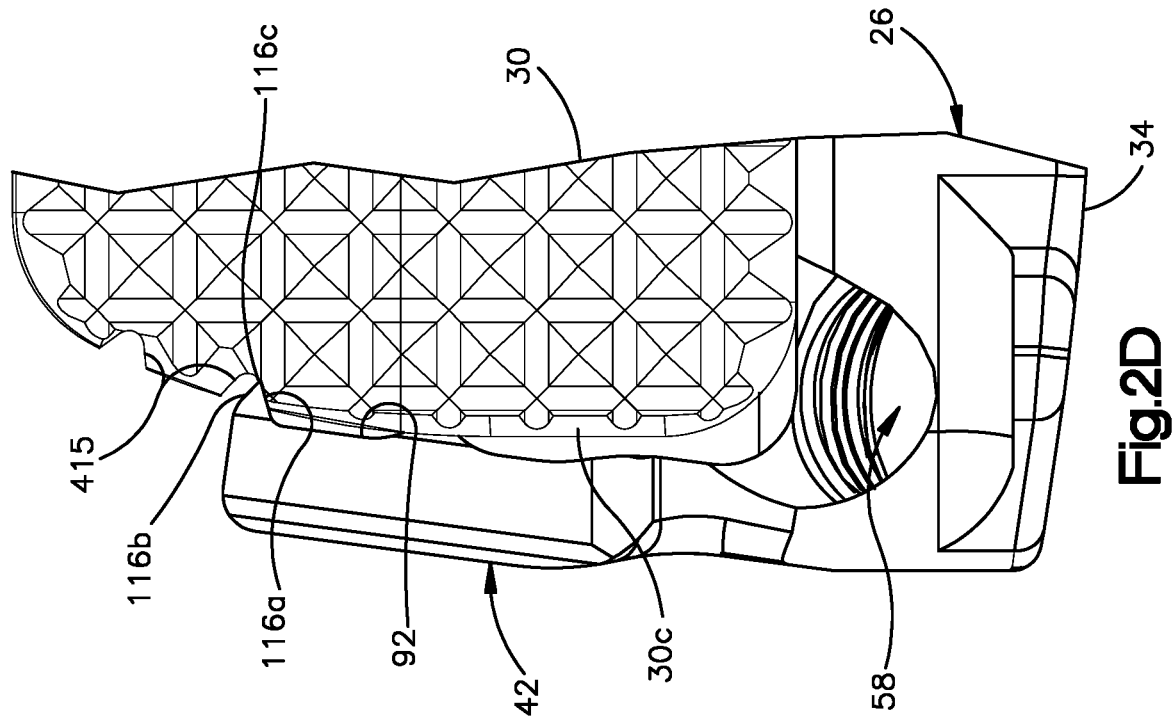
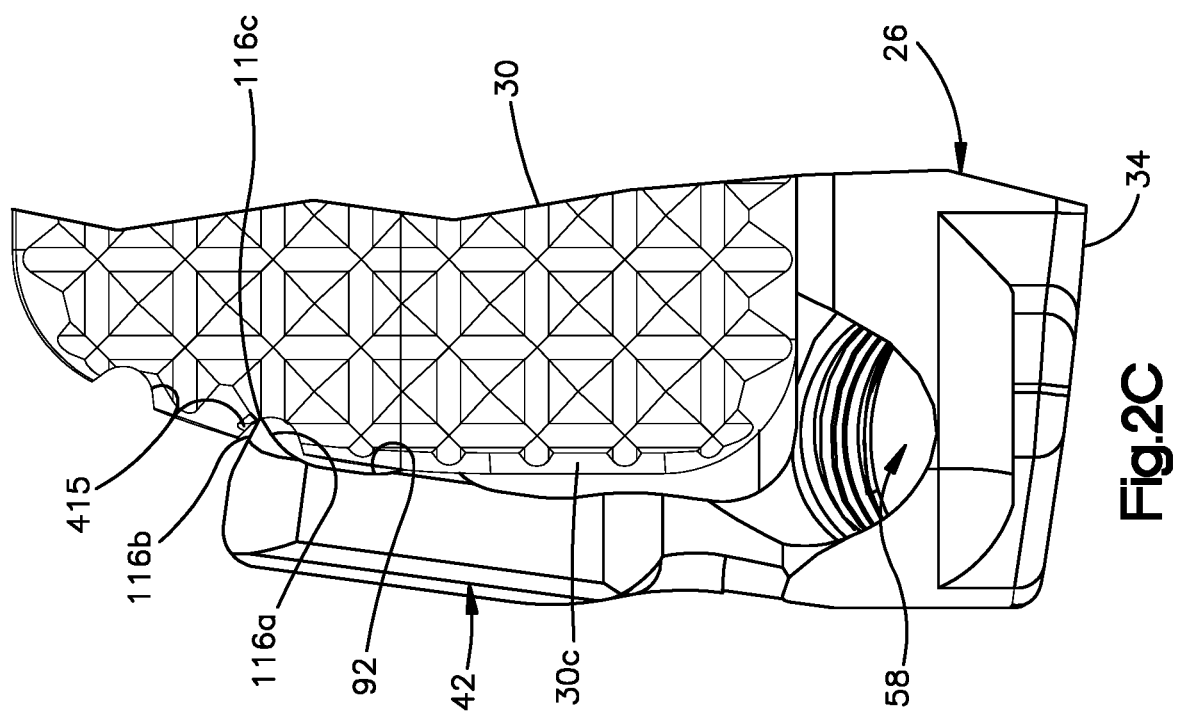

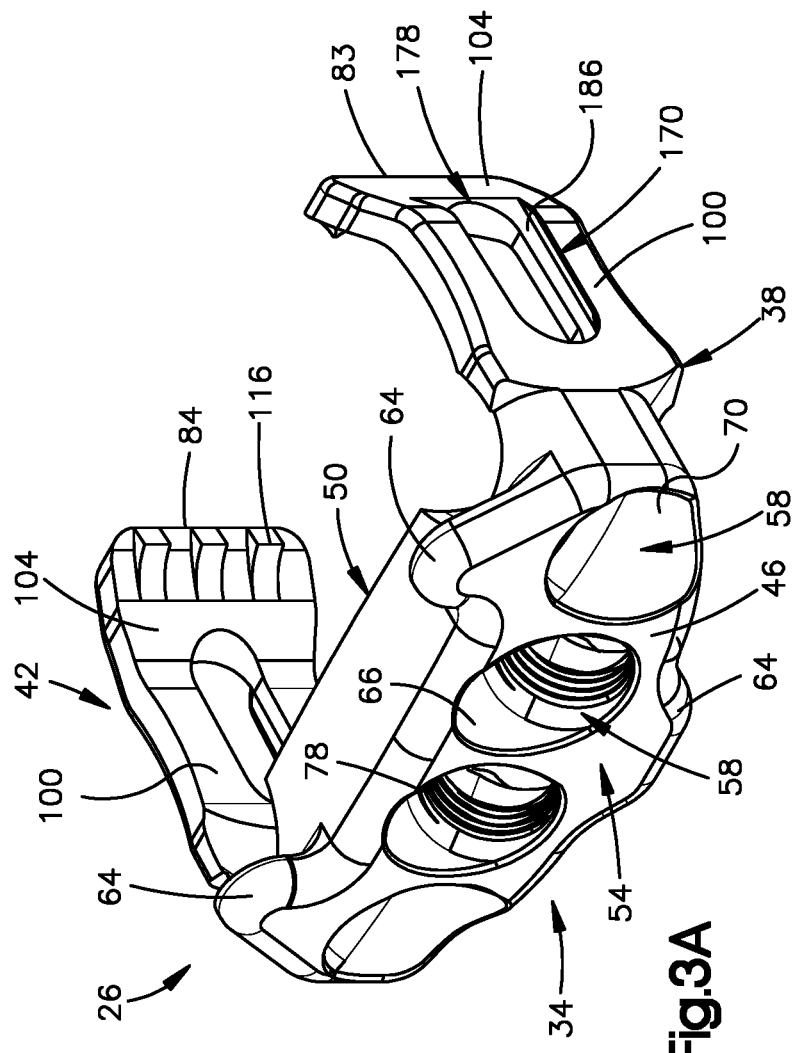

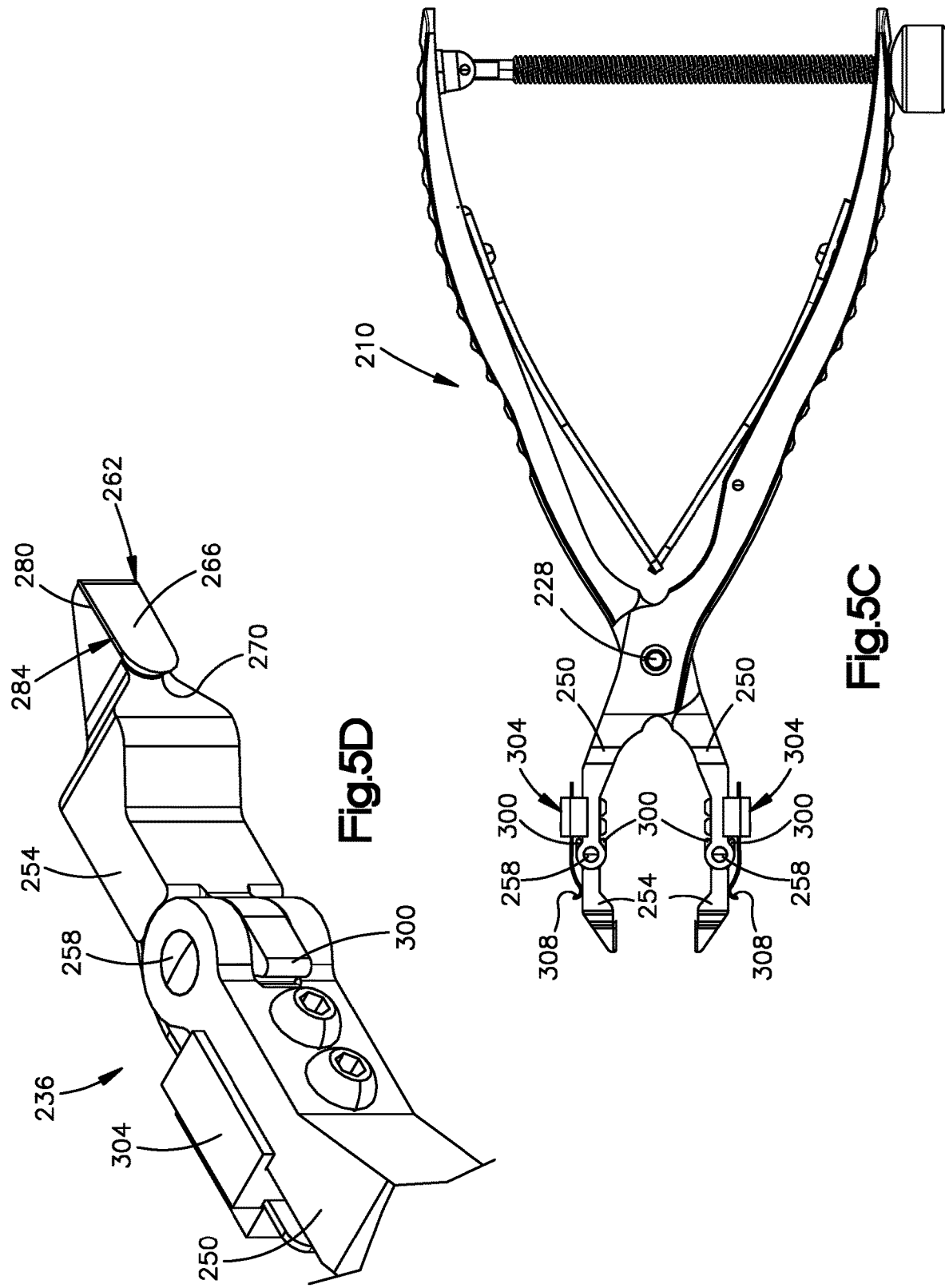

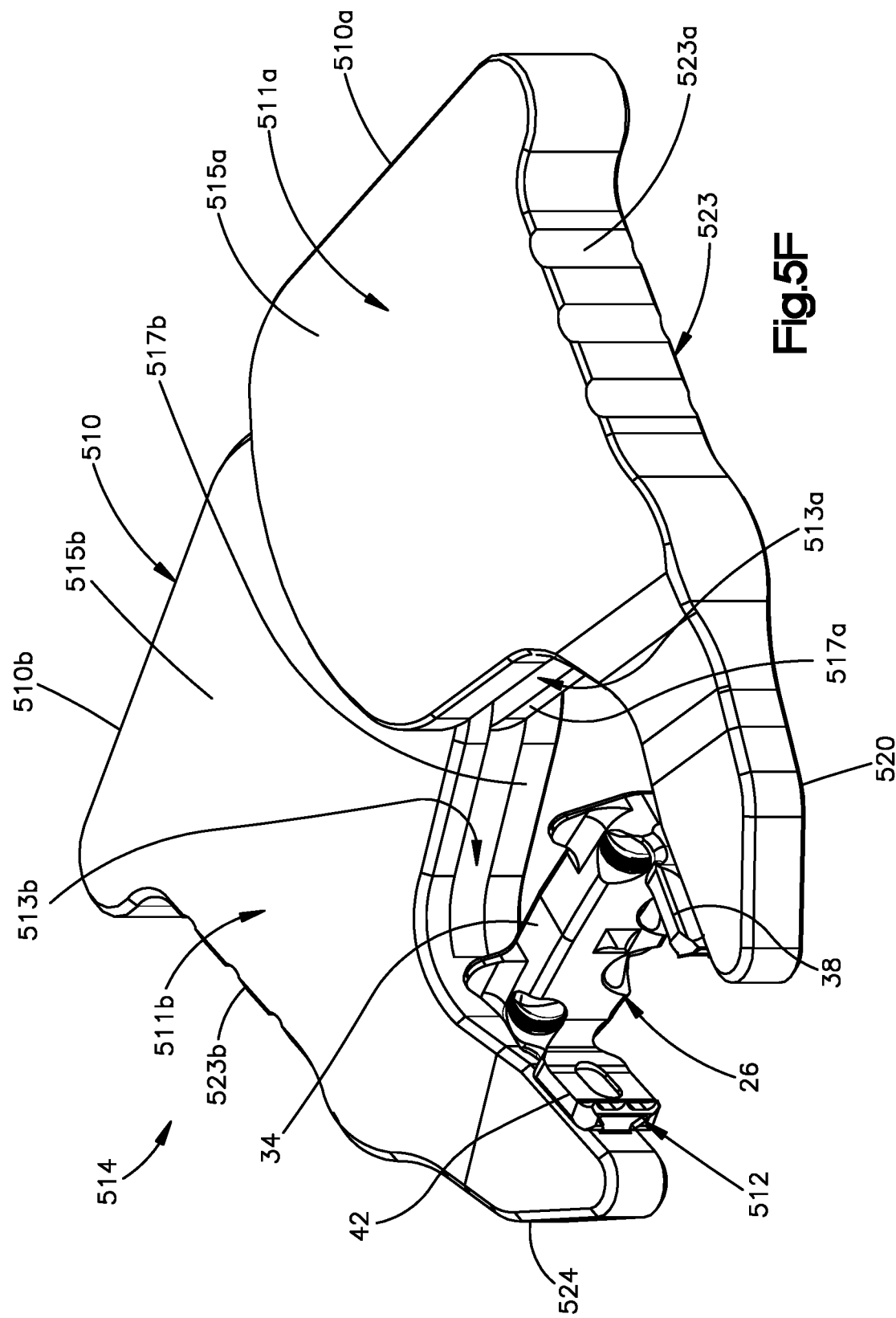

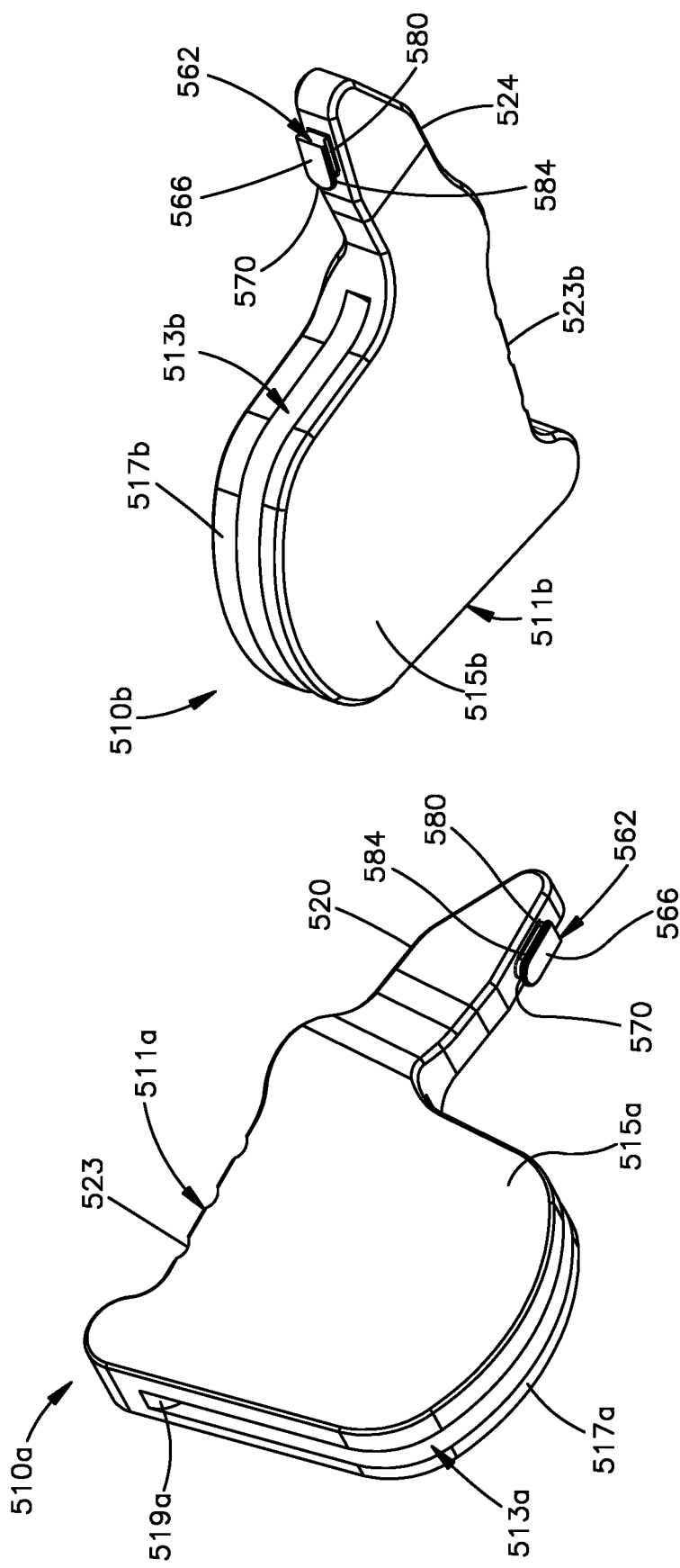

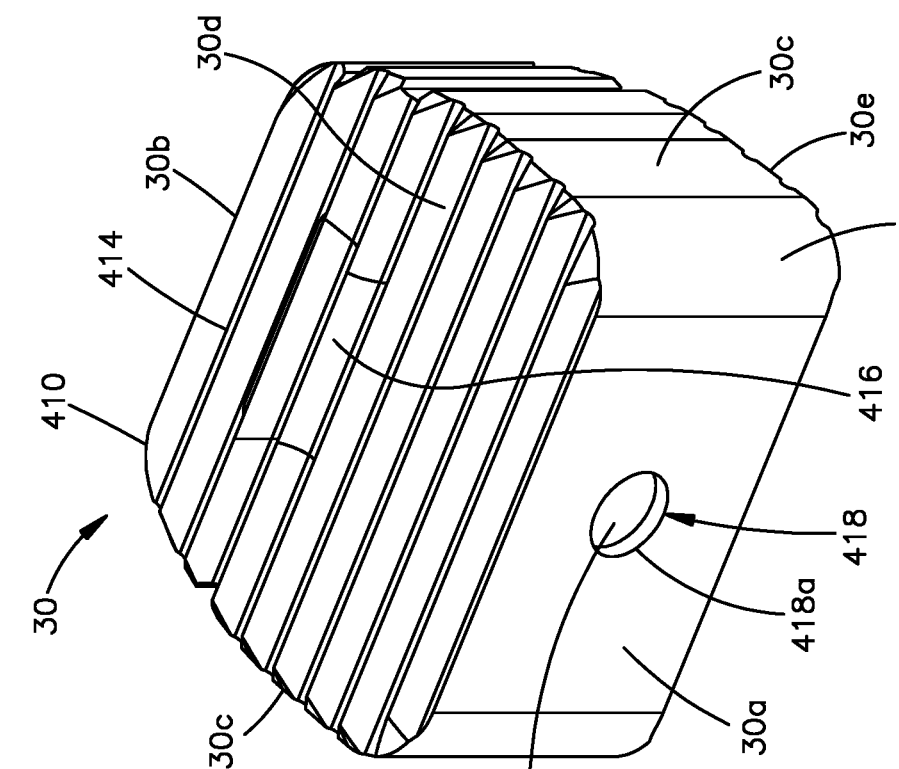
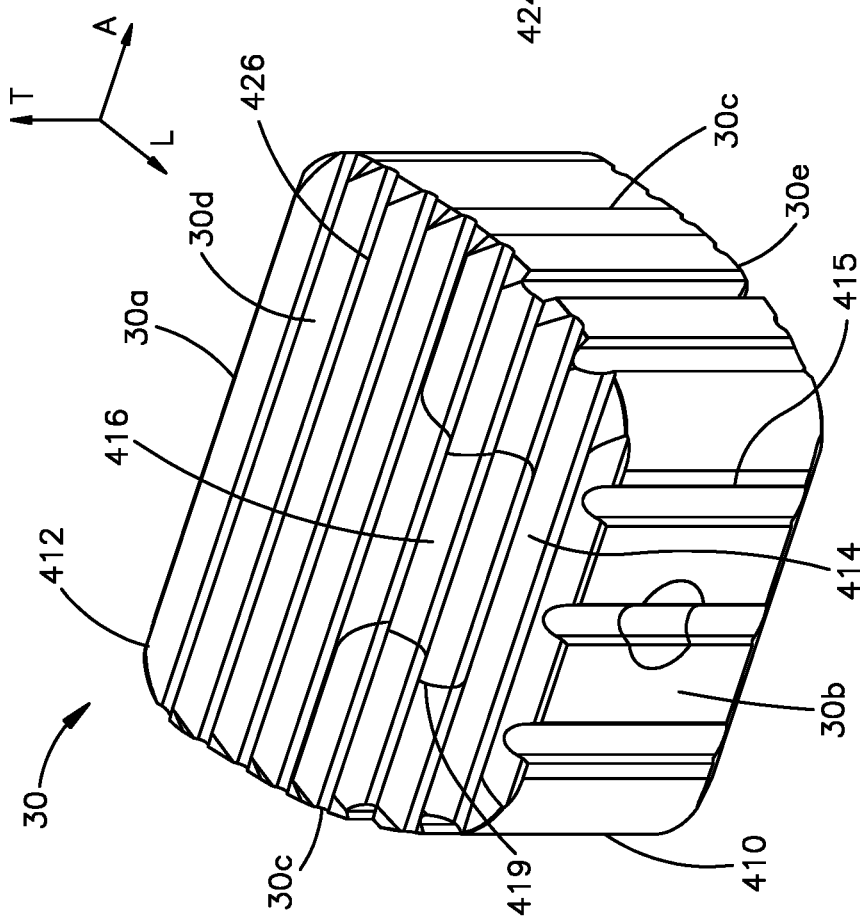

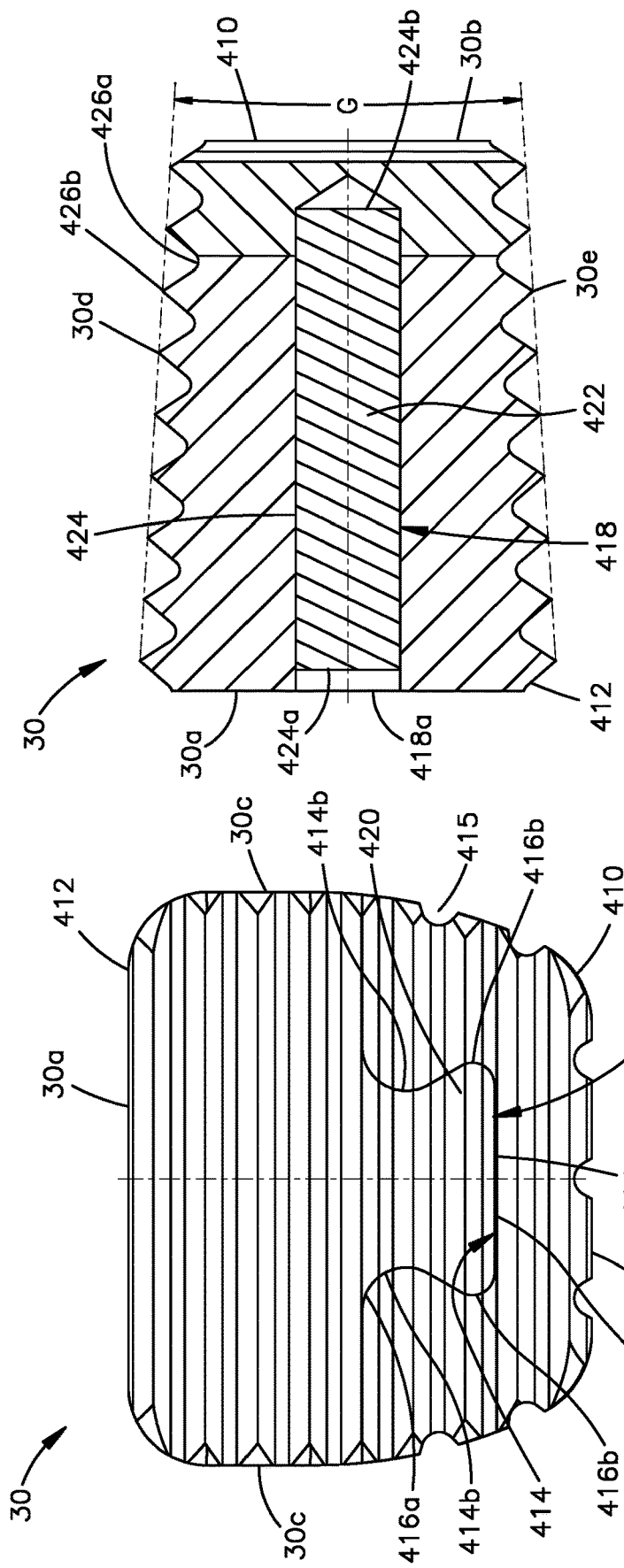

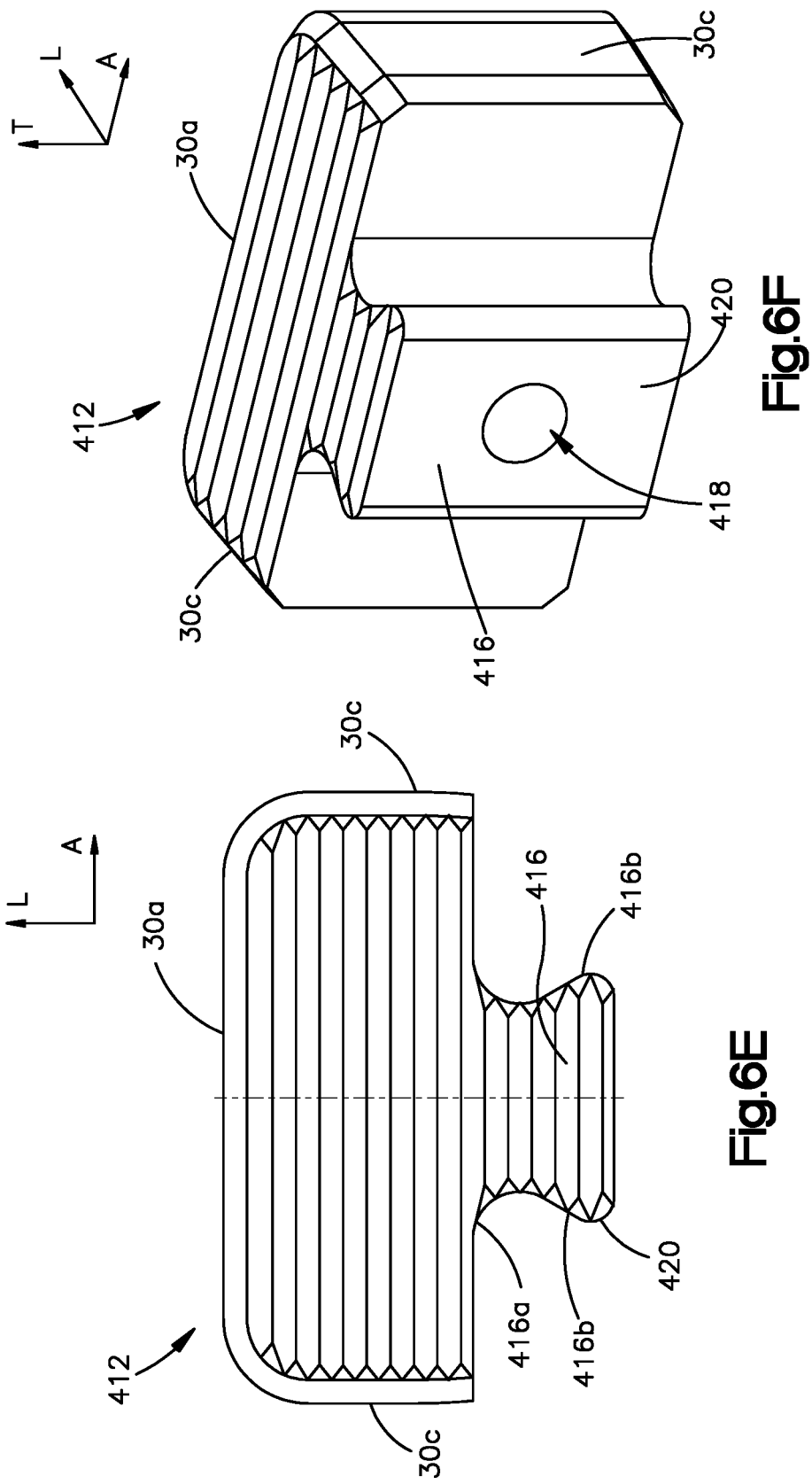

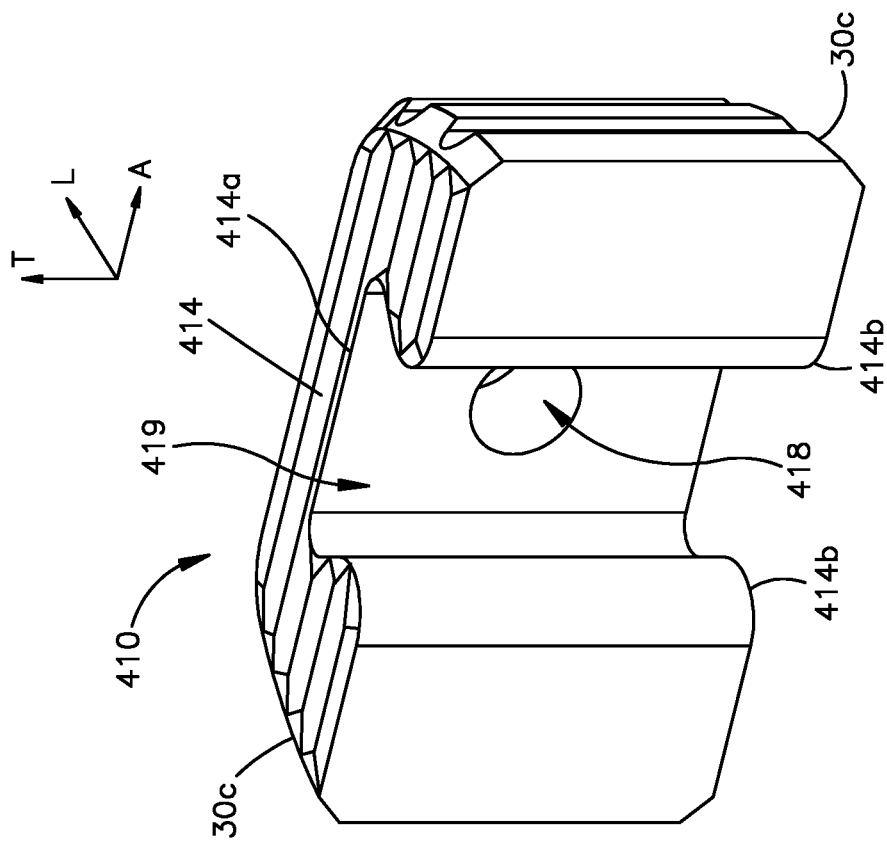
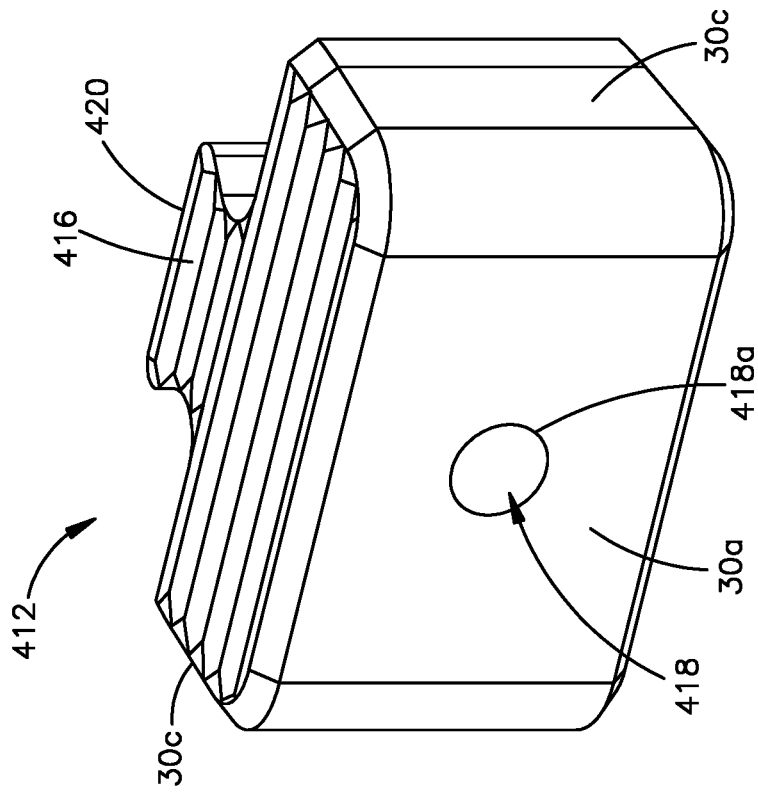

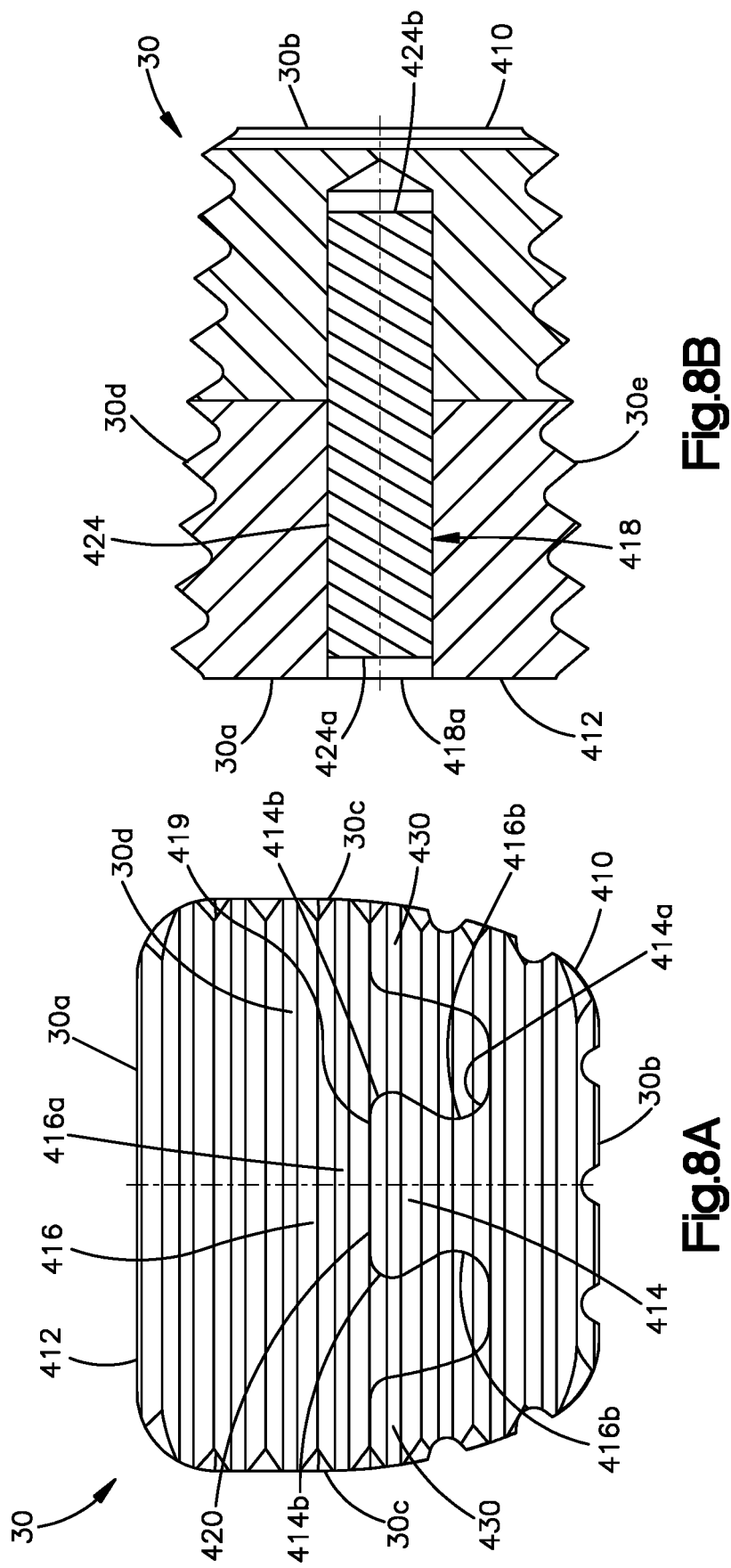

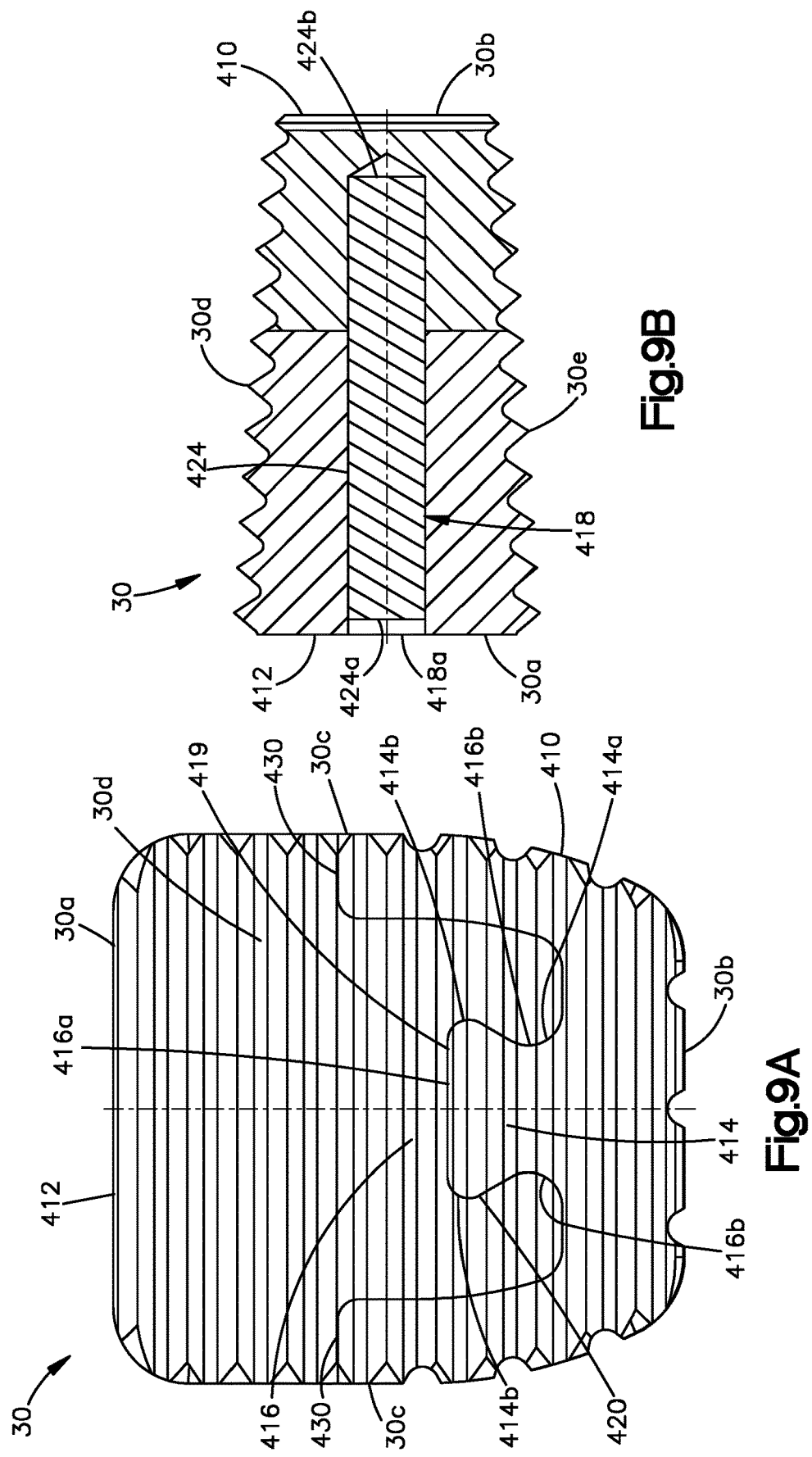

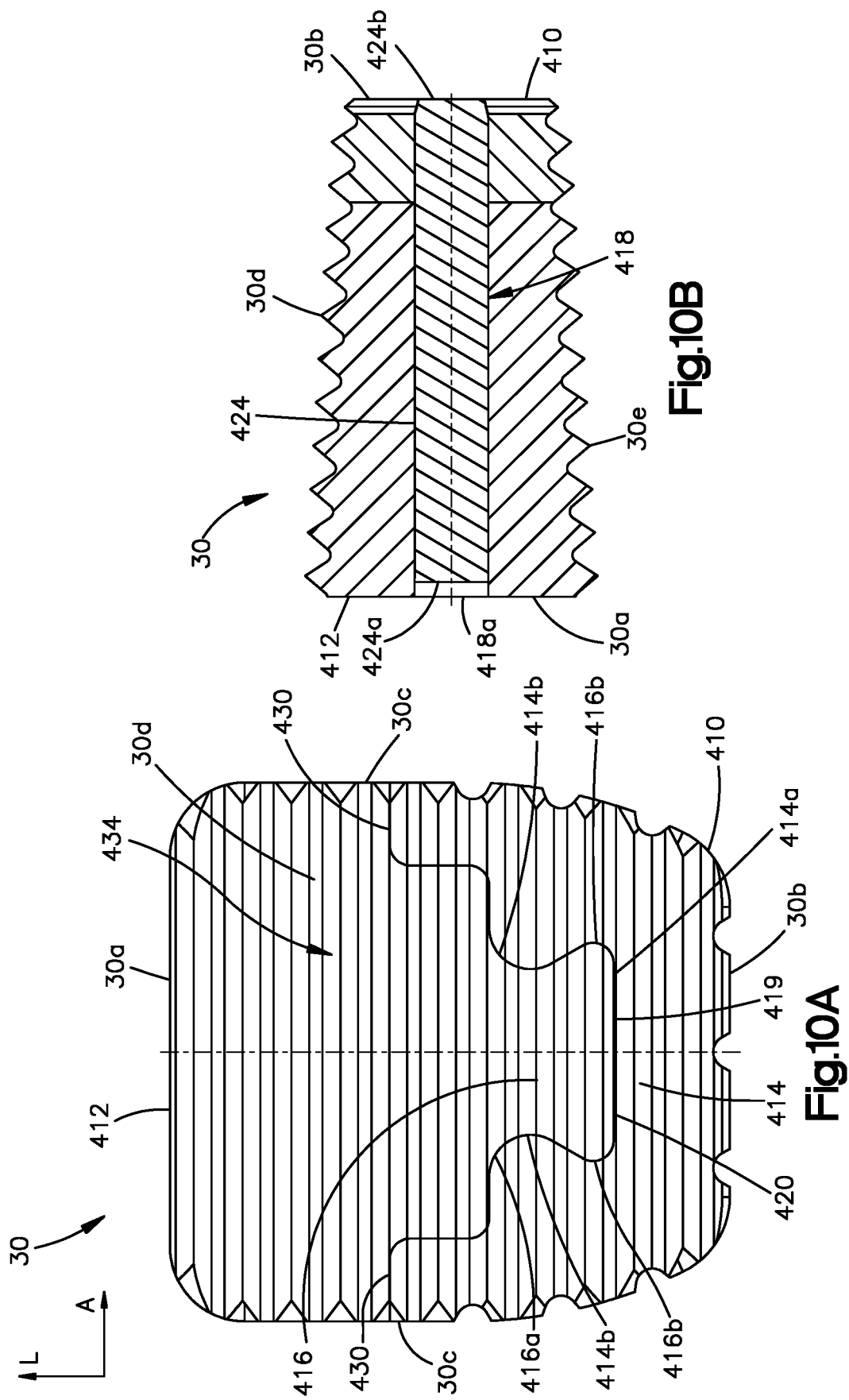

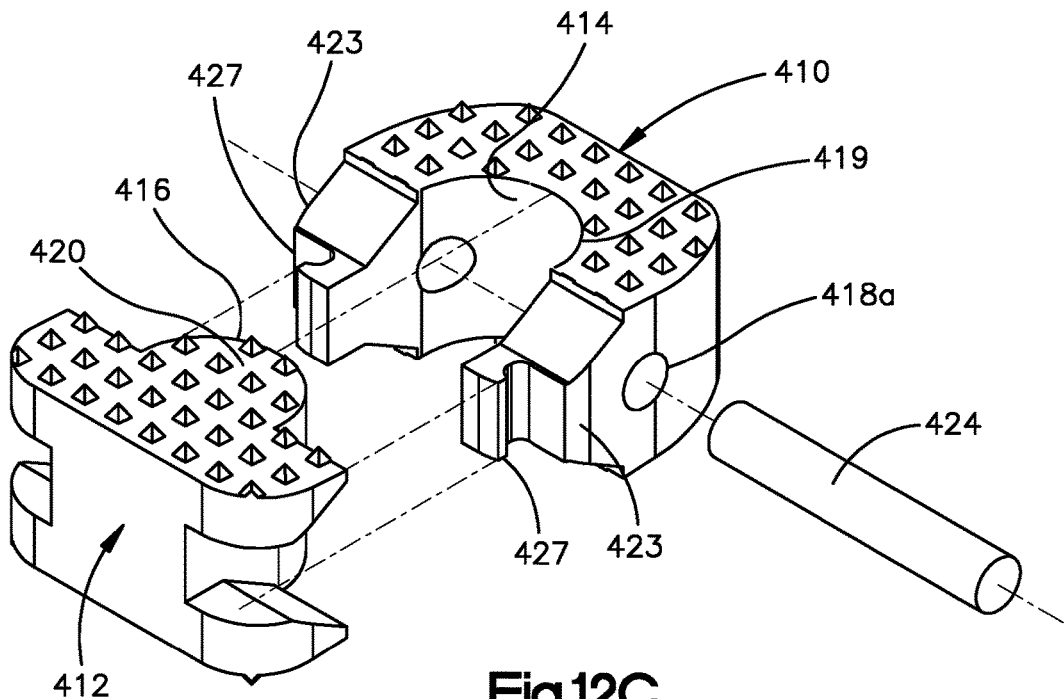
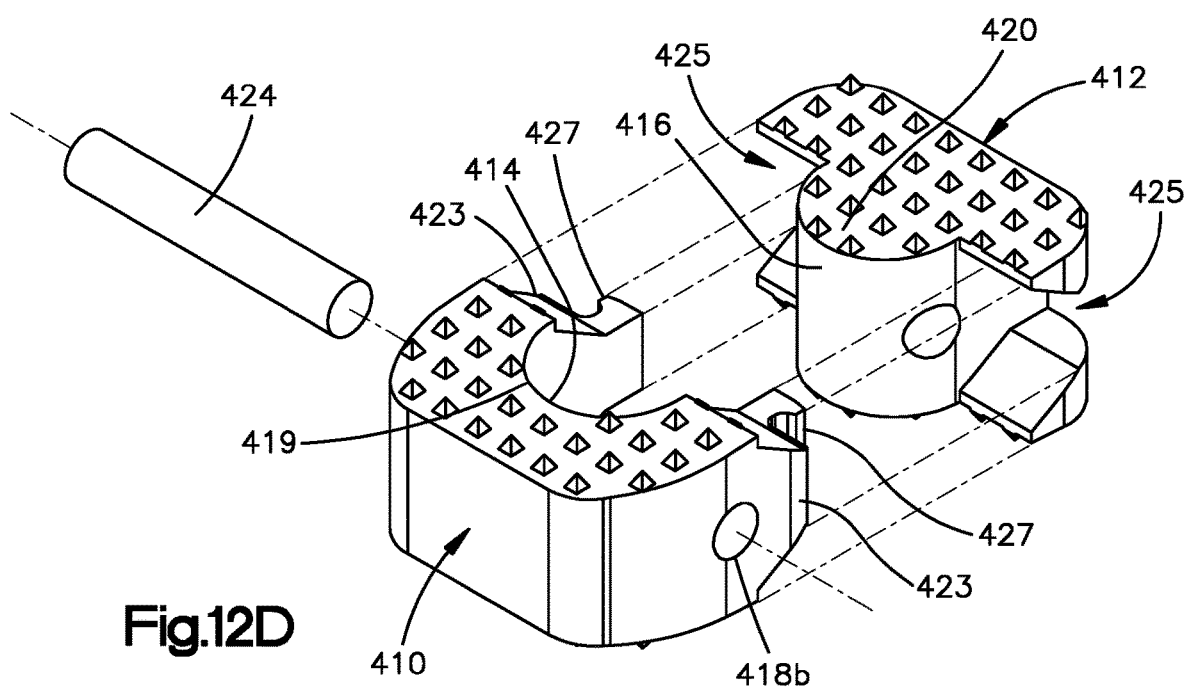

INTERVERTEBRAL IMPLANTS, SYSTEMS, AND METHODS OF USE

CROSS-REFERENCE TO RELATED APPLICATIONS

This is a continuation application of U.S. patent application Ser. No. 16/174,173 filed Oct. 29, 2018, which is a continuation application of U.S. patent application Ser. No. 15/992,464 filed May 30, 2018, which is a continuation application of U.S. patent application Ser. No. 15/704,308 filed Sep. 14, 2017, now U.S. Pat. No. 10,010,432 issued Jul. 3, 2018, which is a continuation application of U.S. patent application Ser. No. 14/520,690 filed on Oct. 22, 2014, now U.S. Pat. No. 9,867,718 issued Jan. 16, 2018, the disclosures of which are hereby incorporated by reference as set forth in their entireties herein.

BACKGROUND

Implants for spinal fusion typically include a spacer to allow for growth of bone between adjacent vertebral bodies while restoring and maintaining intervertebral space height that is defined between the vertebral bodies. In some cases, a plate is used to provide stability during healing so as to allow the patient to quickly resume an active lifestyle. The profile of the plate, which is placed on the anterior aspect of the vertebral bodies, however, can lead to dysphasia or patient discomfort which has precipitated the development of what's known as "zero-profile" devices. One example of a conventional minimal-profile intervertebral implant is insertable substantially entirely into the intervertebral space so as to not substantially extend beyond the footprint of the vertebral bodies that define the intervertebral space.

Other intervertebral implants have been utilized that include a frame shaped in a manner so as to interface with a spacer made from PEEK. Such spacer bodies typically are customized to have complimentary features to the frame so that the spacer bodies may be affixed to the frame. Such frames may not be desirable for spacer bodies made from allograft, however, because allograft spacer bodies may vary in shape, may not include the complimentary features needed to be affixed to the frame, and may degrade or resorb overtime.

SUMMARY

In accordance with one embodiment, an intervertebral implant is configured to be inserted into an intervertebral space. The intervertebral implant can include a spacer and a frame. The spacer, in turn, can include a cortical spacer body comprising a cortical bone graft material, and a cancellous spacer body comprising a cancellous bone graft material. The cancellous spacer body can be disposed proximal with respect to at least a portion of the cortical spacer body. The frame can include a support member disposed proximal with respect to the cancellous spacer body and configured to extend along a portion of the cancellous spacer body, such that the cancellous spacer body is disposed between the support member and the at least a portion of the cortical spacer body. The frame can further include first and second opposed arms that extend from the support member and are configured to engage the cortical spacer body.

BRIEF DESCRIPTION OF THE DRAWINGS

The foregoing summary, as well as the following detailed description of embodiments of the application, will be better understood when read in conjunction with the appended drawings. For the purposes of illustrating the methods, implants and systems of the present application, there is shown in the drawings preferred embodiments. It should be understood, however, that the application is not limited to the precise methods, implants, and systems shown. In the drawings:

FIG. 2A is a perspective view of the intervertebral implant illustrated in FIGS. 1A and 1B, the intervertebral implant having an intervertebral implant frame and a spacer retained by the intervertebral implant frame;

FIG. 2B is a top plan view of the intervertebral implant shown in FIG. 2A;

FIG. 2C is a top plan view of an intervertebral implant similar to FIG. 2B, but showing the frame secured to the spacer in accordance with one embodiment;

FIG. 2D is a top plan view of an intervertebral implant similar to FIG. 2C, but showing the frame secured to the spacer in accordance with another embodiment;

FIG. 3A is a perspective view of the intervertebral implant frame shown in FIG. 2, the intervertebral implant frame having a support member, a first arm extending from the support member, and a second arm extending from the support member, the first and second arms configured to elastically flex away from each other;

FIG. 5C is a top plan view of the expansion instrument shown in FIG. 5B;

FIG. 5D is a detailed view of one of the gripping portions of the expansion instrument shown in FIG. 5B;

FIG. 5F is a perspective view of an expansion instrument in accordance with another embodiment, shown coupled to the intervertebral implant frame;

FIG. 5G is a perspective view of a first member of the expansion instrument illustrated in FIG. 5F FIG. 5H is a perspective view of a second member of the expansion instrument illustrated in FIG. 5F FIG. 5I is a sectional end elevation view of the expansion instrument illustrated in FIG. 5F, shown coupled to the intervertebral implant frame;

FIG. 6A is a perspective view of a spacer of the type illustrated in FIG. 2A, including a cortical spacer body and a cancellous spacer body, and a force transfer member that extends through the cancellous spacer body and at least into the cortical spacer body;

FIG. 6B is another perspective view of the spacer illustrated in FIG. 6A;

FIG. 6C is a top plan view of the spacer illustrated in FIG. 6A;

FIG. 6D is a sectional side elevation view of the spacer illustrated in FIG. 6A;

FIG. 6E is a top plan view of the cancellous spacer body illustrated in FIG. 6A;

FIG. 6F is a perspective view of the cancellous spacer body illustrated in FIG. 6E;

FIG. 6G is another perspective view of the cancellous spacer body illustrated in FIG. 6E;

FIG. 6H is a perspective view of the cortical spacer body illustrated in FIG. 6A;

FIG. 8A is a top plan view of the spacer as illustrated in FIG. 6A, but including engagement members constructed in accordance with an alternative embodiment;

FIG. 8B is a sectional side elevation view of the spacer illustrated in FIG. 8A;

FIG. 9A is a top plan view of the spacer as illustrated in FIG. 6A, but including engagement members constructed in accordance with an another alternative embodiment;

FIG. 9B is a sectional side elevation view of the spacer illustrated in FIG. 9A;

FIG. 10A is a top plan view of the spacer as illustrated in FIG. 6A, but constructed in accordance with yet another alternative embodiment;

FIG. 10B is a sectional side elevation view of the spacer illustrated in FIG. 10A;

FIG. 12C is an exploded perspective view of the intervertebral spacer illustrated in FIG. 12B;

FIG. 12D is another exploded perspective view of the intervertebral spacer illustrated in FIG. 12B;

DETAILED DESCRIPTION

Figure 1A:
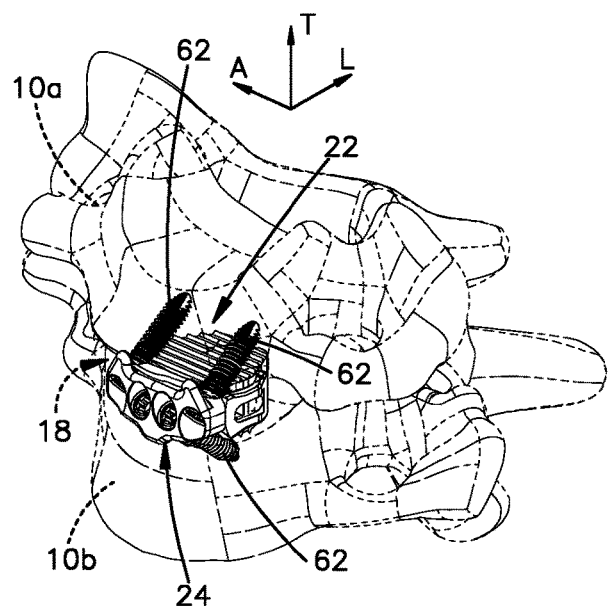
FIG. 1A is a perspective view of an intervertebral implant assembly that is implanted in an intervertebral space defined by a superior vertebral body and an inferior vertebral body, the intervertebral implant assembly including an intervertebral implant and at least a pair of fixation elements that attach the intervertebral implant to the superior vertebral body and the inferior vertebral body, respectively.
Figure 1B:
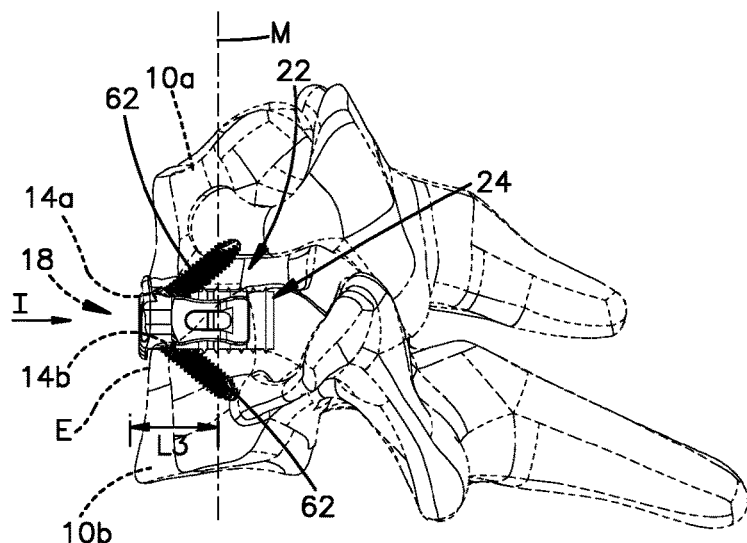
FIG. 1B is a side elevation view of the intervertebral implant assembly as shown in FIG. 1A, the intervertebral space defining an anterior-posterior midline.

Referring to FIGS. 1A and 1B, a superior vertebral body 10a defines a first or superior vertebral surface 14a of an intervertebral space 18, and an adjacent second or inferior vertebral body 10b defines an inferior vertebral surface 14b of the intervertebral space 18. Thus, the intervertebral space 18 is disposed between or otherwise defined by the vertebral bodies 10a and 10b. The vertebral bodies 10a and 10b can be anatomically adjacent vertebral bodies, or can remain after a portion of bone has been removed. The intervertebral space 18 can be disposed anywhere along the spine as desired, including at the lumbar, thoracic, and cervical regions of the spine. As illustrated, the intervertebral space 18 is illustrated after a discectomy, whereby the disc material has been removed or at least partially removed to prepare the intervertebral space 18 to receive an intervertebral implant 22. As shown, the intervertebral implant 22 can be affixed to the superior and inferior vertebral bodies 10a and 10b with respective fixation elements 62. The intervertebral implant 22 and the fixation elements 62 together define an intervertebral implant assembly 24.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

The intervertebral implant 22 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the intervertebral implant 22 is implanted into the intervertebral space 18 along an insertion direction I, the transverse direction T extends vertically generally along the superior-inferior (or caudal-cranial) direction, while the horizontal plane defined by the longitudinal direction L and lateral direction A lies generally in the anatomical plane defined by the anterior-posterior direction, and the medial-lateral direction, respectively. Thus, the lateral direction A can define the medial-lateral direction when the implant 22 is implanted in the intervertebral space. The longitudinal direction L can define the anterior-posterior direction when the implant 22 is implanted in the intervertebral space. Accordingly, the directional terms "vertical" and "horizontal" are used to describe the intervertebral implant 22 and its components as illustrated merely for the purposes of clarity and illustration.

Figure 1C:
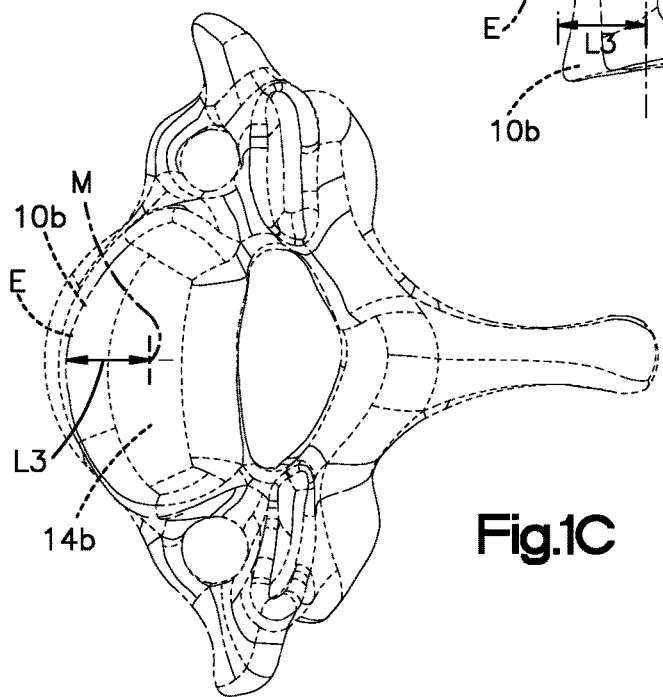
FIG. 1C is a top plan view of the inferior vertebral body shown in FIG. 1B.

As shown in FIGS. 1B and 1C, the vertebral surfaces 14a and 14b of the vertebral bodies 10a and 10b can define a geometrical centroid M that is generally located at an anterior-posterior midpoint between an anterior end and a posterior end of the surfaces 14a and 14b. As shown in FIG. 1B, the intervertebral implant 22 is configured to be disposed or otherwise implanted in the intervertebral space 18 such that a portion of the intervertebral implant 22 is located on a posterior side of a medial lateral plane that intersects the centroid M, and a portion of the intervertebral implant 22 is located on an anterior side of the medial lateral plane that intersects the centroid M.

In reference to FIGS. 1A, 1B, 2A and 2B, the intervertebral implant 22 includes an intervertebral implant frame 26 and an intervertebral spacer 30 that is retained by the frame 26. In one example, the spacer 30 is configured to be received by the frame 26. Thus, it can be said that the frame 26 is configured to receive the spacer 30. The intervertebral implant 22, defines a proximal end P and a distal end D. The distal end D is spaced from the proximal end P in a distal direction, which is along the longitudinal direction L. When the intervertebral implant 22 is implanted in an intervertebral space, the proximal end P can define an anterior end, and the distal end D can define a posterior end spaced from the anterior end in an anterior-posterior direction. The intervertebral implant 22 is configured to be inserted into the intervertebral space in an insertion direction. In one example, the insertion direction can be in the distal direction, such that the distal direction can be referred to as an insertion direction into the intervertebral space. It should be appreciated, of course, the intervertebral implant 22 can be inserted into the intervertebral space along any suitable direction as desired, for instance in the lateral direction A. Alternatively, the intervertebral implant 22 can be inserted in an oblique direction that includes both the distal direction and the lateral direction A. Thus, the insertion direction can be in at least the distal direction, which can include the distal direction and the oblique direction. Further, it should be appreciated that the intervertebral implant 22 is configured to be inserted into the thoracic region, and the lumbar region of the spine. Further, it should be appreciated that the intervertebral implant 22 is configured to be inserted into the thoracic region, and the lumbar region of the spine. Conversely, the proximal end P is spaced from the distal end D in a proximal direction that is opposite the distal direction, and also is along the longitudinal direction L. The frame 26 may be made from any biocompatible material, such as TAN alloy, or PEEK. The spacer 30 can be composed of a bone graft such as allograft bone, autograft bone or xenograft bone. It should be appreciated that the spacer 30 can further include ceramics, polymers, metals, and biomaterials. In particular, the spacer 30 can include a cortical spacer body 410 made of cortical bone graft material, and a cancellous spacer body 412 made of cancellous bone graft material. By using a spacer 30 composed of bone graft, surface area for fusion can be maximized with respect to synthetic spacers. Additionally, the bone graft promotes bony in-growth of the respective vertebral bodies into the spacer 30, and increased probability and speed of sound fusion between the spacer and the respective vertebral bodies. The frame 26 is configured to be attached to various bone graft spacer footprint geometries, which may or may not conform to the internal footprint of the frame 26. It should be further appreciated that the insertion direction can be in the distal direction, and that the distal direction can be oriented in a lateral approach into the intervertebral space, an anterior-posterior approach into the intervertebral space, or an oblique approach into the intervertebral space. The oblique approach can be oblique to both the anterior-posterior approach and the lateral approach.

As shown in FIGS. 3A-3E the frame 26 includes a support member 34, a first arm 38 that extends from the support member 34, and a second arm 42 that extends from the support member 34. In the illustrated embodiment, the first and second arms 38 and 42 are flexible arms that extend from opposed ends of the support member 34 such that the support member 34, the first arm 38, and the second arm 42 together create a three wall structure that retains and secures the spacer 30 to the frame 26.

Figure 3B:
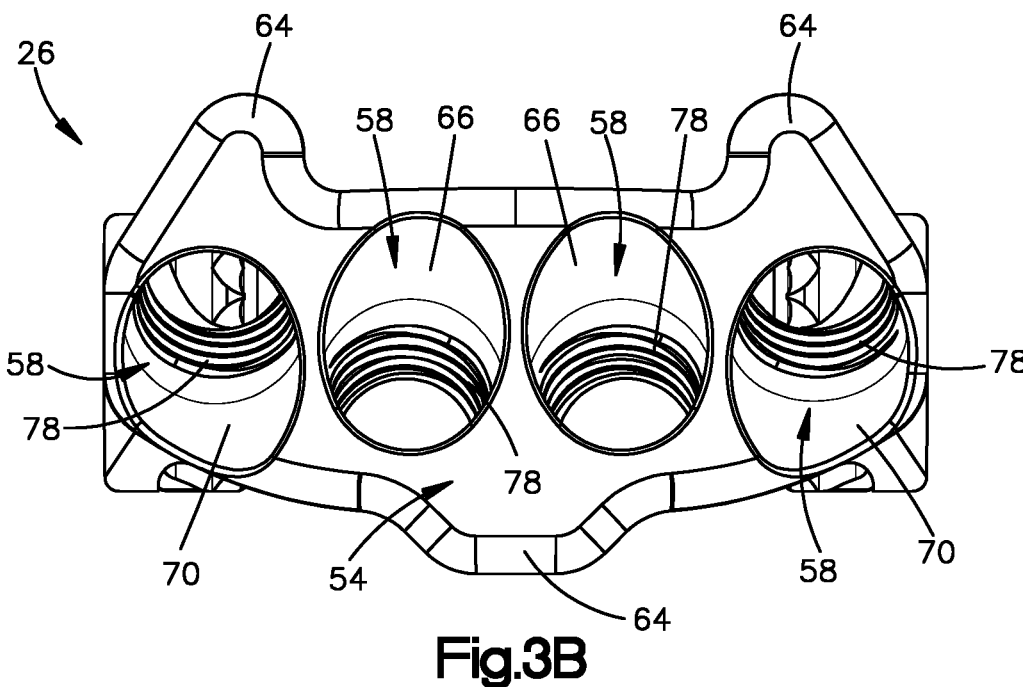
FIG. 3B is a front elevation view of the intervertebral implant frame shown in FIG. 3A.
Figure 3C:
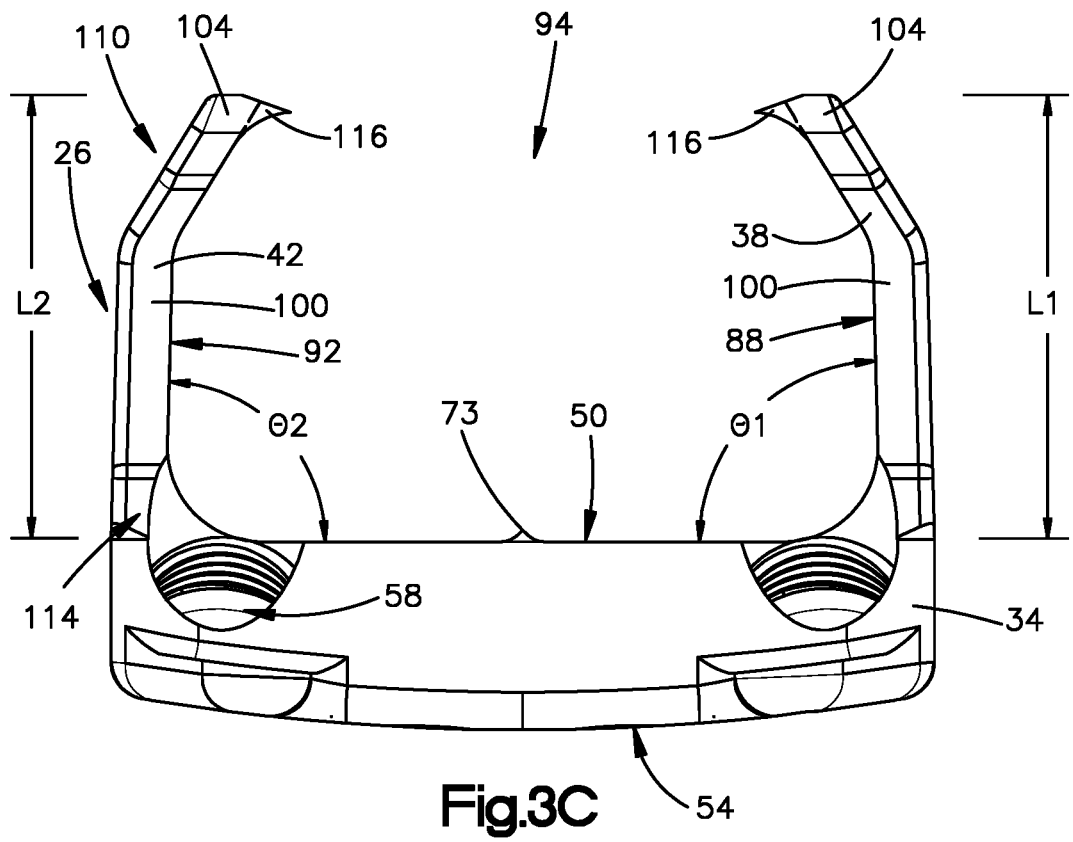
FIG. 3C is a top plan view of the intervertebral implant frame shown in FIG. 3A.

As shown in FIGS. 3A-3C, the support member 34 includes a body 46 that defines an inner surface 50, an outer surface 54, and at least one, such as two or such as four, fixation element receiving apertures 58 that extend through the body 46 from the outer surface 54 to the inner surface 50. Each fixation element receiving aperture 58 is configured to receive a respective fixation element, such as fixation element 62 shown in FIGS. 4A and 4B. While the fixation elements 62 are illustrated as screws, it should be appreciated that the fixation elements 62 may also be nails or any other fixation element configured to attach the intervertebral implant 22 to the first and second vertebral bodies 10a and 10b. As shown, the support member 34 can further include at least one tab 64 such as a plurality of tabs 64 that extend from the body 46 generally along the transverse direction T. For instance, the support member 34 can include three tabs 64. The tabs 64 may be disposed at an anterior side of the vertebral bodies and prevent over-insertion of the frame 26 into the intervertebral space 18. In the illustrated embodiment, the support member 34 includes a pair of superior tabs 64 that extend in an upward or superior direction from the body 35, and an inferior tab 64 that extends in a downward or inferior direction from the body 35. Each of the tabs 64 can be configured to sit flush or slightly proud of an anterior surface of the vertebral bodies depending on the patient's spinal anatomy and/or site preparation. It should be appreciated, however, that the support member 34 can include other configurations for the tabs 64. For example, the support member 34 can include a single superior tab 64 and a pair of inferior tabs 64. Alternatively still, as described in more detail below with respect to FIG. 3F, the support member can include a pair of superior tabs and a pair of inferior tabs.

As shown in FIG. 3B, two of the fixation element receiving apertures 58 are inner apertures 66 that extend through the body 46 at a downward angle relative to the insertion direction I, and two of the fixation element receiving apertures 58 are outer apertures 70 that extend through the body 46 at an upward angle relative to the insertion direction I. The inner apertures 66 are configured to receive respective fixation elements, such as fixation element 62 shown in FIGS. 4A and 4B, to thereby attach the intervertebral implant 22 to the inferior vertebral body 10b. Similarly, the outer apertures 70 are configured to receive respective fixation elements 62 to thereby attach the intervertebral implant 22 to the superior vertebral body 10a. It should be appreciated, however, that the inner apertures 66 can extend through the body 46 at an upwards angle and the outer apertures 70 can extend through the body 46 at a downwards angle, as desired. Moreover, it should be appreciated that the support member 34 can define any number of fixation element receiving apertures 58 as desired. It should be appreciated that the fixation element receiving apertures 58 can be configured as boreholes sized to accommodate the fixation elements 62, or can be configured as recesses or a partial boreholes in order to accommodate the fixation elements 62.

As shown in FIG. 3B, the apertures 58 each define internal threads 78. The internal threads 78 are configured to engage external threads 80 defined by a head 82 of the respective fixation element 62 (see FIGS. 4A-4B) that is received within the apertures 58, such that the internal threads 78 mate with the external threads 80. It should be appreciated, however, that the apertures 58 can be void of threads as desired. The orientation of the apertures 58 may be configured such that the fixation elements that are received by the apertures 58 may have an insertion variance of +/−5 degrees and do not allow toggling or settling. Once fully received, the fixation elements may lock to the frame 26 to thereby increase the surgeon's reassurance of good screw trajectories and can act as a safety by preventing possibilities of over-insertion during implantation.

Figure 6J:
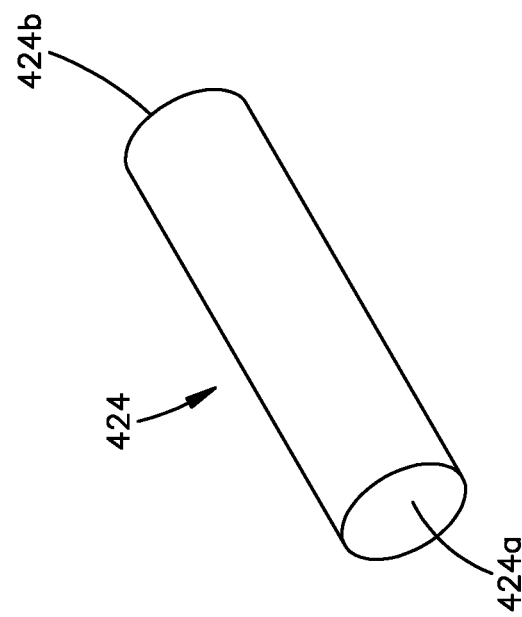
FIG. 6J is a perspective view of the force transfer member illustrated in FIG. 6A.
Figure 6I:
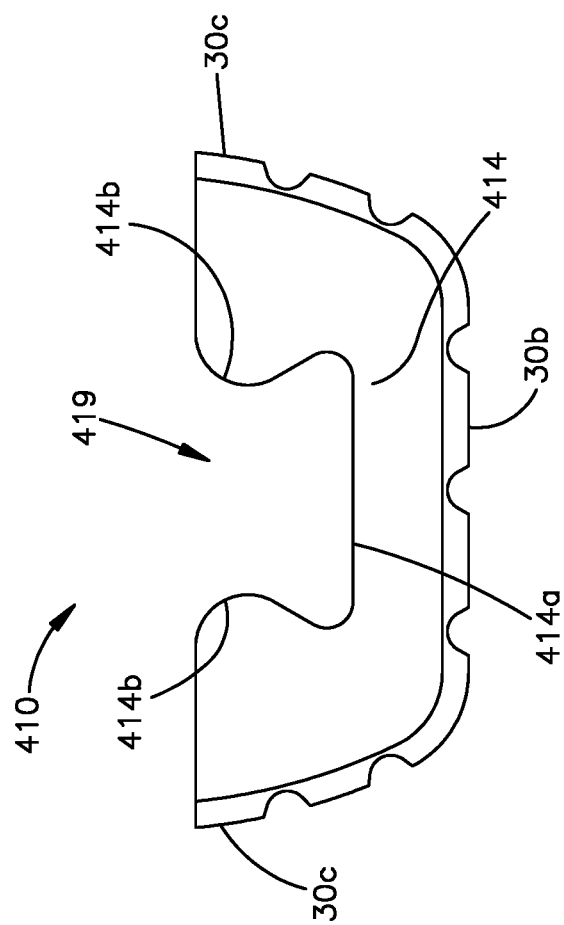
FIG. 6I is a top plan view of the cortical spacer body illustrated in FIG. 6H.

As shown in FIG. 3C, support member 34 can include an abutment member 73 that extends from the inner surface 50 along the distal direction. It will be appreciated that the abutment member 73 can be configured to abut a force transfer member 424 (see FIG. 6D) of the spacer 30 that receives forces from the frame 26, and transfers the received forces to the cortical spacer body 41, as will be described in more detail below. In certain embodiments, the abutment member 73 can further be sized to be inserted into a force transfer channel 418 (see FIG. 6B) in the cancellous spacer body 412 so as to abut the force transfer member 424. The abutment member 73 is illustrated as a spike though it should be appreciated, that the abutment member 73 can have other shapes as desired. For instance, the abutment member 73 can have a pointed or a rounded abutment surface that abuts the force transfer member 424 as desired.

As shown in FIGS. 2A, and 3A-3E, the first arm 38 and the second arm 42 each extend from the support member 34 and define a first distal terminal end 83 and a second distal terminal end 84, respectively. The first and second arms 38 and 42 each define gripping portions and support portions. The gripping portions are configured to retain the spacer 30 while the support portions are configured to support the vertebral bodies 10a and 10b relative to each other. The gripping portions and the support portions can be a single structure or the support portions can be separate structures that extend from the gripping portions. The arms 38 and 42 can be radiolucent so as to increase fluoroscopy visibility. The first arm 38 includes a first inner spacer contacting surface 88 and the second arm 42 includes a second inner spacer contacting surface 92 that is spaced from the first inner spacer contacting surface 88 along a first direction, such as the lateral direction A. The inner surface of the support member 34, the first inner spacer contacting surface 88, and the second inner spacer contacting surface 92 together define a void 94 that is configured to receive and grip the spacer 30. The terminal ends 83 and 84 are spaced apart from the support member along a second direction, such as the longitudinal direction L that is substantially perpendicular to the first direction so as to define first and second lengths $L_1$ and $L_2$, respectively of the first and second arms 38 and 42. The first and second arms 38 and 42 are sized such that the first and second lengths $L_1$ and $L_2$ are each greater than a length $L_3$ defined between an anterior end E of the inferior vertebral body 10b and the centroid M of the surface 14b of the inferior vertebral body 10b, as shown in FIG. 1C. It should be appreciated, that the first and second arms 38 and 42 can also be sized such that the first and second lengths $L_1$ and $L_2$ are greater than a length defined between an anterior end of the superior vertebral body 10a and a centroid of the surface 14a of the superior vertebral body 10a. The first and second lengths $L_1$ and $L_2$ may be between about 3.5 mm and about 12 mm, between about 6.0 mm and about 10 mm, and preferably about 9.5 mm. In some embodiments, the support member 34, the first arm 38, and the second arm 42 extend around at least 51% of the spacer 30, and preferably around at least 80% of the spacer 30.

The flexible arms 38 and 42 can have a transverse height and a lateral width that at least partially define a cross-sectional area of the arms 38 and 42. The arms 38 and 42 can have a cross-sectional area that may vary so long as the arms 38 and 42 are capable of elastically deforming or flexing to thereby allow the frame 26 to receive the spacer and subsequently apply a retention force to the spacer 30 after the frame 26 has received the spacer 30. In that regard, the arms 38 and 42 are configured to elastically flex laterally outwardly away from each other, or otherwise elastically deform from a first position to a second flexed position to allow the frame 26 to receive the spacer 30. It should be appreciated that the first position can be a relaxed position of the arms 38 and 42 or a flexed position of the arms 38 and 42 that is outwardly flexed with respect to a relaxed position. At least respective portions of the arms 38 and 42, such as contact locations 320 and 324 (see FIG. 6E), are further spaced from each other in the second position than when in the first position. Once the spacer 30 is disposed between the arms 38 and 42, the arms 38 and 42 may flex inwardly toward each other to a third or engaged position whereby the arms 38 and 42 engage the spacer 30 so as to secure the frame 26 to the spacer 30 as shown in FIG. 2. It should be appreciated that the third position can be outwardly flexed with respect to the first position, and can be substantially equal to the first position. Thus, the respective portions of the arms 38 and 42 can be further spaced from each other when in the third position with respect to the first position, or the respective portions of the arms 38 and 42 can be spaced from each other when in the third position a distance substantially equal to the distance that the respective portions of the arms 38 and 42 are spaced when in the first position. Thus, it can be said that when the arms 38 and 42 are in the third position, at least respective portions of the arms 38 and 42 are spaced apart a distance equal to or greater than (or no less than) the distance that the arms 38 and 42 are spaced when in the first position. It will be further appreciated from the description below in accordance with certain embodiments (see, for instance FIG. 14C) that at least respective portions of the arms 38 and 42 can be spaced apart a distance when in the engaged position that is less than the distance that the respective portions of the arms 38 and 42 are spaced apart when in the first position.

As shown in FIG. 3C, the first and second arms 38 and 42 extend from the support member 34 such that the first and second arms 38 and 42 are angled toward each other so as to push the spacer 30 toward the other of the first and second arms 38 and 42 and toward the support member 34. For example, the inner surface of the support member 34 and the first inner spacer contacting surface 88 form an angle $Ø_1$ that is less than 90 degrees, and the inner surface 50 of the support member 34 and the second inner spacer contacting surface 92 form an angle $Ø_2$ that is less than 90 degrees. In the illustrated embodiment, $Ø_1$ and $Ø_2$ are each about 88 degrees, though it should be appreciated that $Ø_1$ and $Ø_2$ may be any angle as desired, and may be different angles with respect to each other.

Figure 3D:
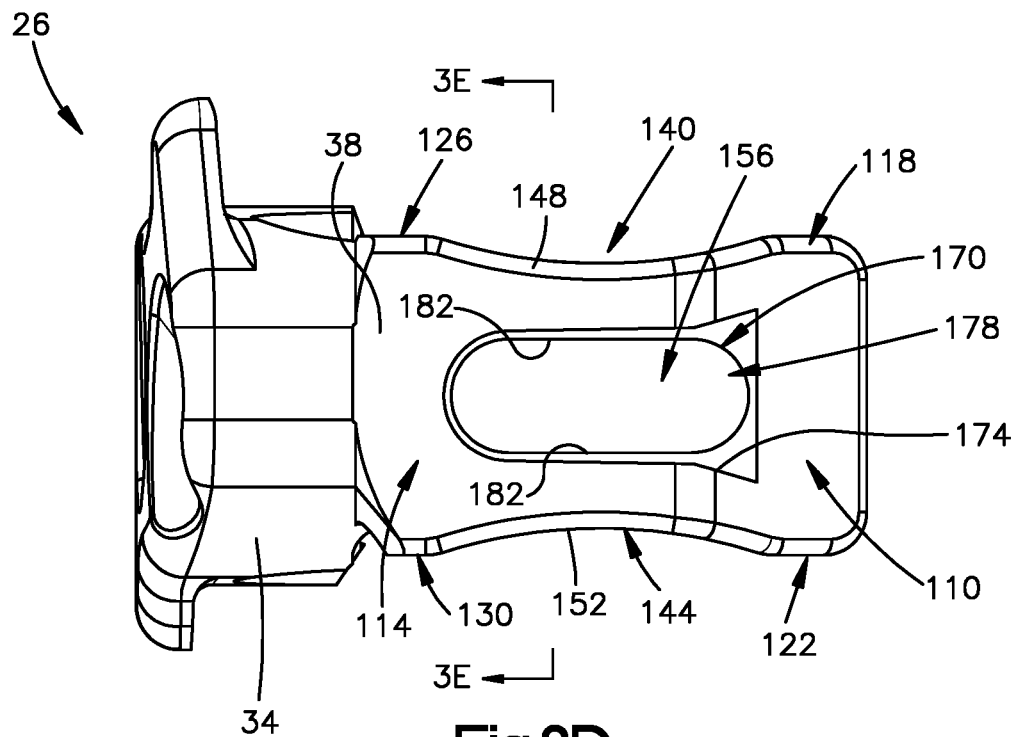
FIG. 3D is a side elevation view of the intervertebral implant frame shown in FIG. 3A.

As shown in FIGS. 3C and 3D, each arm 38 and 42 includes a substantially straight portion 100 that extends from the support member 34, and a distal bent or angled portion 104 that extends from a distal end of the straight portion 100 toward the other of the bent portions 104 such that the bent portions 104 are configured to contact a distal surface of the spacer 30. As shown, the bent portions 104 at least partially wrap around the spacer 30 to thereby prevent the spacer 30 from separating from the frame 26 after the spacer 30 has been retained by the frame 26. As shown in FIG. 3A, each arm 38 and 42 can include at least one retention member 116, such as a plurality of retention members 116 that extend out from the first and second inner spacer contacting surfaces 88 and 92. The retention members 116 can be arranged in a respective first column supported by the first arm 38, and a second column supported by the second arm 42. In the illustrated embodiment, the retention members 116 define teeth that extend out of the bent portions 104 so as to form a column of teeth on each bent portion 104. The retention members 116 are configured to engage the spacer 30 when the frame 22 is retaining the spacer 30 to thereby ensure that the spacer 30 remains retained by the frame 22. It should be appreciated, however, that the retention member 116 can have any configuration as desired, so long as the retention member 116 is capable of engaging the spacer 30. For example, the retention members 116 can be configured as spikes that extend from the inner surfaces 88 and 92 at an angle, elongate blades, punches that can be punched into the spacer 30 by an individual after the spacer 30 is disposed in the frame 26, or any suitable roughened surface, grit-blasted surface, or knurled surface that is configured to engage the spacer 30 and thereby retain the spacer 30.

Referring to FIG. 6A, the spacer 30 defines a proximal end surface 30a and a distal end surface 30b that is spaced from the proximal end surface 30a in the distal direction along the longitudinal direction L. The spacer 30 further defines a pair of opposed side surfaces 30c spaced from each other along the lateral direction A. The spacer 30 further defines a top surface 30d and a bottom surface 30e spaced from the top surface 30d in the transverse direction T. The spacer 30 can define a plurality of grooves 415 that can extend into the side surfaces 30c at the cortical spacer body 410, and the distal end surface 30b. The grooves can extend at least into the spacer 30 along the transverse direction T, and can extend through the spacer 30 along the transverse direction T. The retention members 116 supported by the first arm 38 are configured to be inserted into the grooves 415 at a first one of the side surfaces 30c. The retention members 116 supported by the second arm 42 are configured to be inserted into the grooves 415 at the second one of the side surfaces 30c.

Figure 2F:
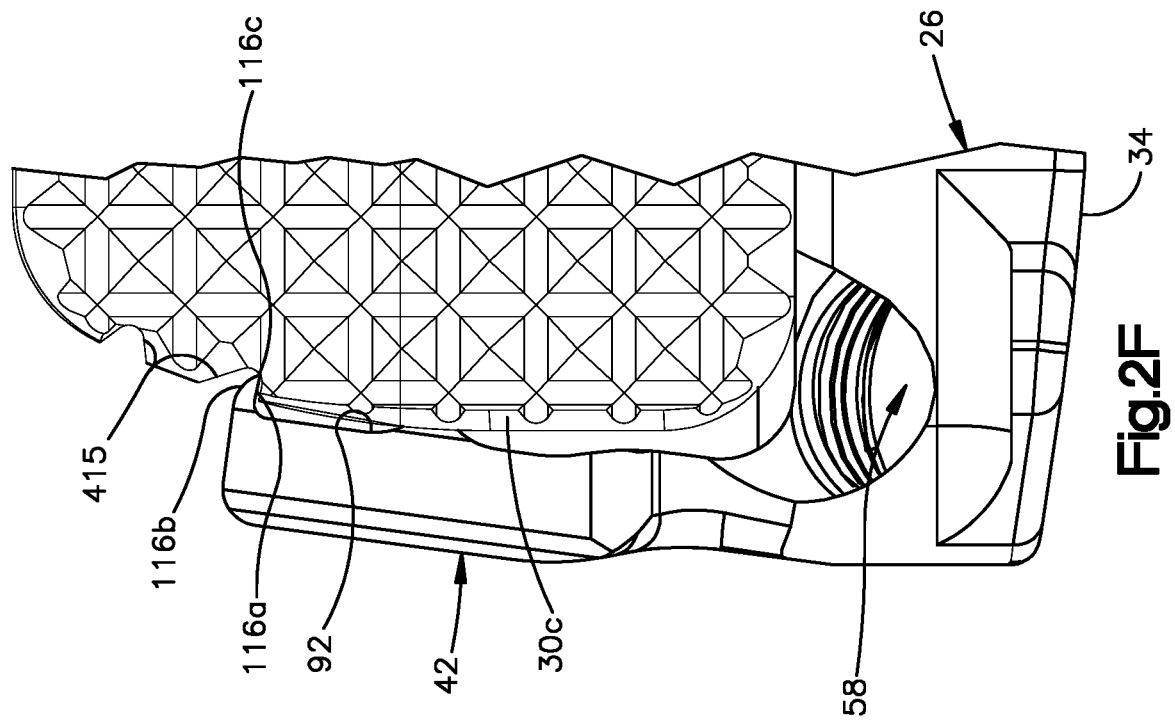
FIG. 2F is a top plan view of an intervertebral implant similar to FIG. 2B, but showing the frame secured to the spacer in accordance with still another embodiment.
Figure 2E:
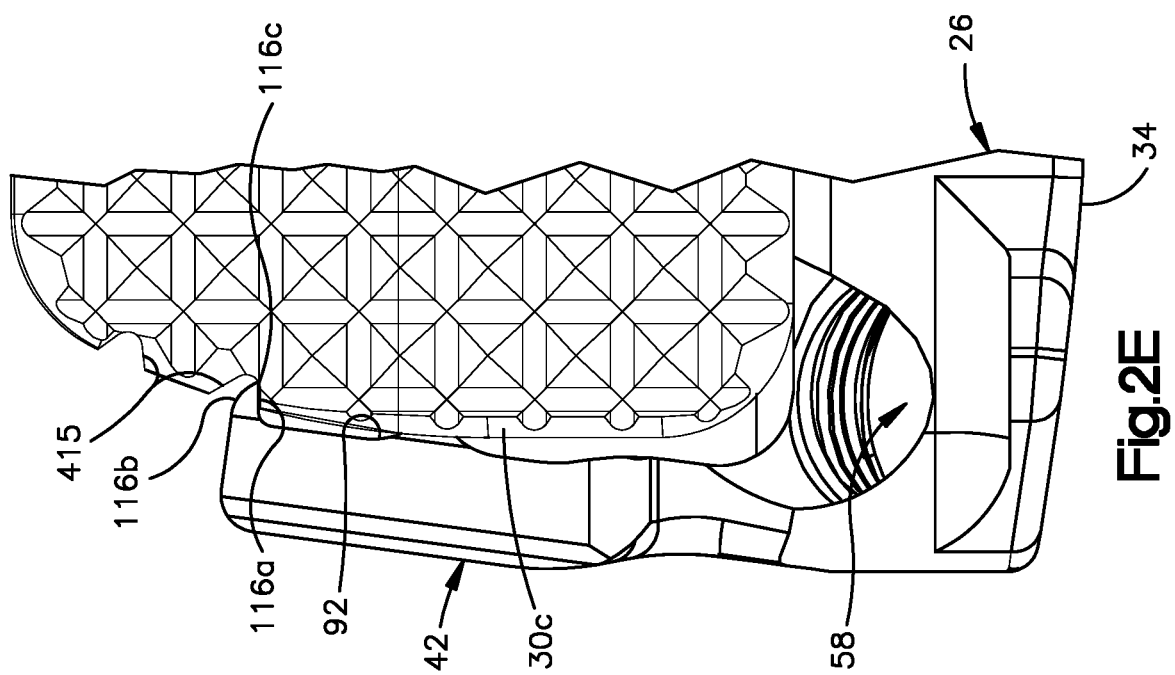
FIG. 2E is a top plan view of an intervertebral implant similar to FIG. 2D, but showing the frame secured to the spacer in accordance with yet another embodiment.

Referring now to FIGS. 3C-3D and 2C, the retention members 116 can define a proximal surface 116a and a distal surface 116b that each extend from the respective inner surfaces 88 and 92 of the corresponding first and second arms 38 and 42. The proximal surface and distal surfaces 116a and 116b can converge toward each other and can adjoin each other at a tip 116c. The proximal surface can define a concavity as illustrated in FIG. 2C. The distal surface 116b be substantially linear. For instance, the distal surface 116b can be oriented along the lateral direction A. The tip 116c can be offset in the distal direction with respect to a location of the inner surface from which the proximal surface 116a extends. As illustrated in FIG. 2D, the proximal surface 116a can be substantially linear. For instance, the proximal surface 116a can be angled with respect to the lateral direction A. In one example, the proximal surface 116a can be oriented so as to extend in both the distal direction and the lateral direction A as it extends from the respective inner surface toward the tip 116c. The distal surface 116b can be convex as it extends from the respective inner surface toward the tip 116c. Referring to FIG. 2E, the proximal surface 116a be substantially linear. For instance, the proximal surface 116a can be oriented along the lateral direction A. The distal surface 116*b* can be convex as it extends from the respective inner surface toward the tip 116*c*. As illustrated in FIG. 2F, the proximal surface 116*a* can be concave as it extends out from the respective inner surface toward the tip 116*c*. The distal surface 116*b* can be convex as it extends out from the respective inner surface toward the tip 116*c*. The tip 116*c* can be offset in the proximal direction with respect to a location of the inner surface from which the proximal surface 116*a* extends. Each of the retention members 116 can overlap the spacer within the groove 415 by any distance as desired. For instance, each of the retention members 116 can overlap the spacer within the groove 415 by a distance between and including approximately 0.5 mm and approximately 4.0 mm. As a function of the length of the spacer 30 along the longitudinal direction L, the overlap can be within the range of 25% and 100% of the length of the spacer 30 in the longitudinal direction L. For instance, the overlap can be within the range of 40% and 80% of the length of the spacer 30 in the longitudinal direction L.

As shown in FIG. 3D, the arms 38 and 42 may be configured to assist in bearing compressive loads by the vertebral bodies 10*a* and 10*b* to thereby mitigate subsidence and settling. As shown, each arm 38 and 42 defines a respective distal portion 110 and a respective proximal portion 114. The distal portions 110 are spaced apart from the proximal portions 114 along the longitudinal direction L such that when the frame 26 is disposed in the intervertebral space 18, the distal portions 110 are on the posterior or distal side of the centroid M of the surface 14*b* of the inferior vertebral body 10*b*, and the proximal portions 114 are on the anterior or proximal side of the centroid M of the surface 14*b* of the inferior vertebral body 10*b*. Each distal portion 110 can define a superior vertebral body contacting surface 118 and an inferior vertebral body contacting surface 122. Similarly, each proximal portion 114 can define a superior vertebral body contacting surface 126 and an inferior vertebral body contacting surface 130. Because of the length of the arms 38 and 42 and because of the transverse height of the arms 38 and 42 at their distal and proximal portions, the frame 26 can bear compressive loads from the vertebral bodies if the spacer 30 were to compress.

As shown in FIG. 3D, the arms 38 and 42 may be configured to conform to the lordotic curve of the spine and in particular of the intervertebral space 18 in which the frame 26 is to be disposed. For example, a line drawn between the superior vertebral body contacting surfaces 118 and 126 of the first arm 38 forms an angle that is between about 0 degrees and about −5 degrees with respect to the insertion direction I, and a line drawn between the inferior vertebral body contacting surfaces 122 and 130 of the first arm forms a line that is between about 0 degrees and about 5 degrees with respect to the insertion direction I. Similarly, a line drawn between the superior vertebral body contacting surfaces 118 and 126 of the second arm 42 forms an angle that is between about 0 degrees and about −5 degrees with respect to the insertion direction, and a line drawn between the inferior vertebral body contacting surfaces 122 and 130 of the second arm 42 forms an angle that is between about 0 degrees and about 5 degrees with respect to the insertion direction I. It should be appreciated, however, that the lines drawn between the superior vertebral body contacting surfaces 118 and 126, and between the inferior vertebral body contacting surfaces 122 and 130 can be any angle as desired. For example, the lines may be parallel to each other. Therefore, it can be said that a first plane is defined by the superior vertebral body contacting surfaces, and a second plane is defined by the inferior vertebral body contacting surfaces. The first plane and the second plane can be parallel to each other or converge toward each other.

As shown in FIG. 3D, each arm 38 and 42 can further include a superior cut-out 140 and an inferior cut-out 144 to thereby provide visual access to the superior vertebral body 10*a* and to the inferior vertebral body 10*b* respectively when the frame 26 is disposed in the intervertebral space 18. The cut-outs 140 and 144 are each disposed between the proximal portions 114 and distal portions 110 of the first and second arms 38 and 42. As shown, the superior cut-outs 140 extend laterally through an upper portion of the arms 38 and 42 so as to define upper curved recesses 148 in the straight portions 100 of the arms 38 and 42. Similarly, the inferior cut-outs 144 extend laterally through a lower portion of the arms 38 and 42 so as to define lower curved recesses 152 in the arms 38 and 42. It should be appreciated that the superior and inferior cut-outs 140 and 144 can have other configurations as desired. For example, the cut-outs 140 and 144 can define rectangular channels that extend through the arms 38 and 42.

Figure 3E:
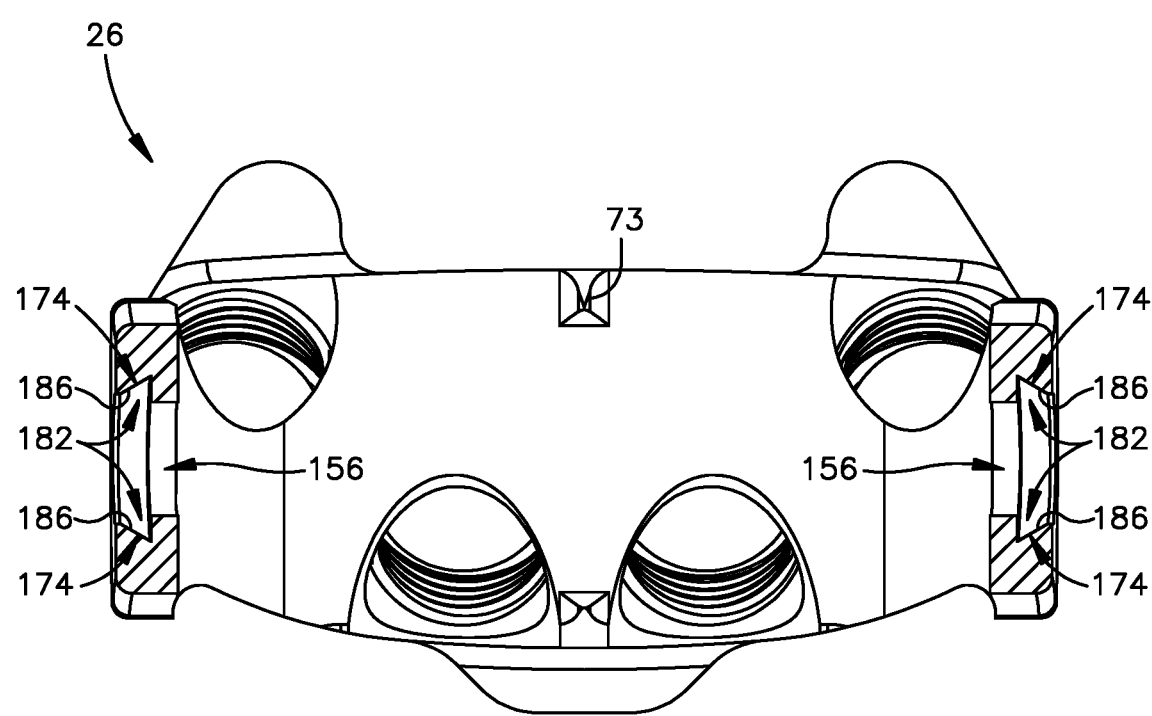
FIG. 3E is a cross-sectional view of the intervertebral implant frame shown in FIG. 3D through the line 3E-3E.

As shown in FIGS. 3D and 3E, each arm 38 and 42 can further include a window 156 that extends laterally through the straight portions 100 of the arms 38 and 42 between the superior and inferior cut-outs 140 and 144. The windows 156 are configured to provide visual access to the spacer 30 through the first and second arms 38 and 42 when the frame 26 is retaining the spacer 30. As shown, the windows 156 are oval shaped and elongate along the longitudinal direction L. It should be appreciated, however, that the windows 156 can have any shape as desired. For example, the windows 156 can also be rectangular shaped.

As shown in FIGS. 3A, 3D, and 3E, each arm 38 and 42 can include an engagement member 170 that is configured to receive a first and a second external expansion force, respectively, from an expansion instrument prior to insertion of the spacer 30 into the void 94 such that at least one of the first and second arms 38 and 42 elastically expands or elastically flexes with respect to the other of the first and second arms 38 and 42 in response to the expansion forces. As shown in FIG. 3A, the engagement members 170 each define a dove-tailed slot 174 that defines an opening 178 at its distal end such that the expansion instrument can engage the dove-tailed slot 174 in a direction that is opposite to the insertion direction I of the frame 26, thereby securing the expansion instrument to the dove-tailed slot 174. As shown in FIG. 3D, the dove-tailed slots 174 are wider at the openings 178 and taper as they extend proximally. The wider openings 178 provide a guide for the expansion instrument to engage the engagement members 170. As shown in FIG. 3A, the dove-tailed slots 174 each include a pair of opposed recesses 182 that define angled engagement surfaces 186. It should be appreciated, however, that the engagement members 170 can have any configuration as desired so long as they can receive respective expansion forces.

Figure 3F:
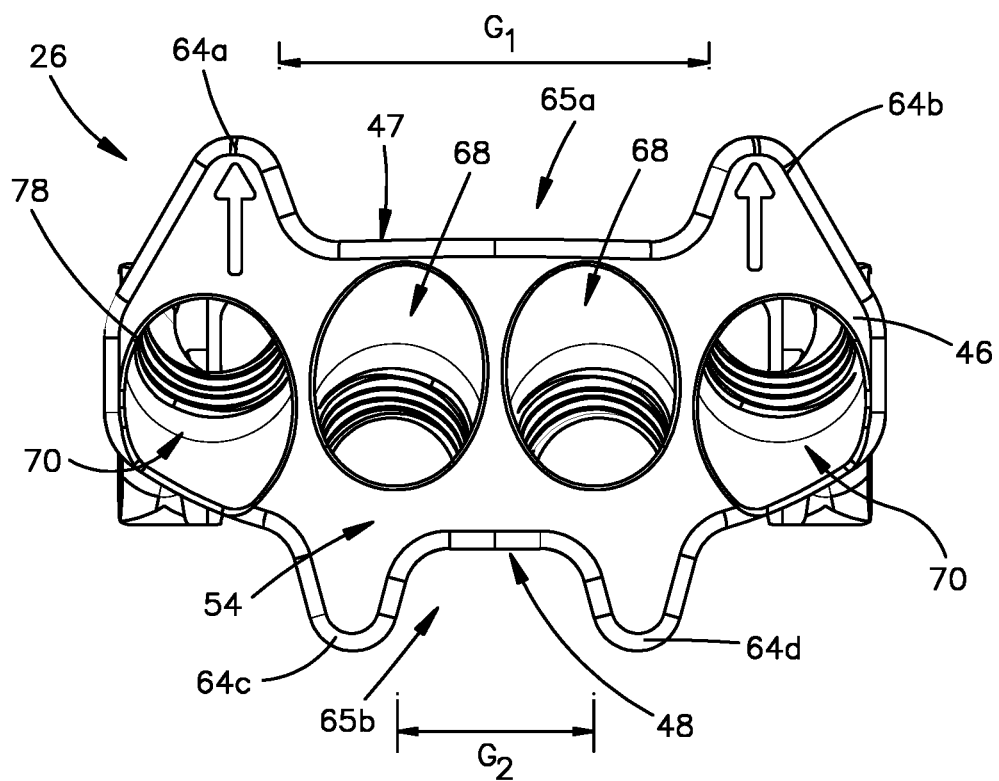
FIG. 3F is another perspective view of the intervertebral implant frame shown in FIG. 3A.
Figure 4A:
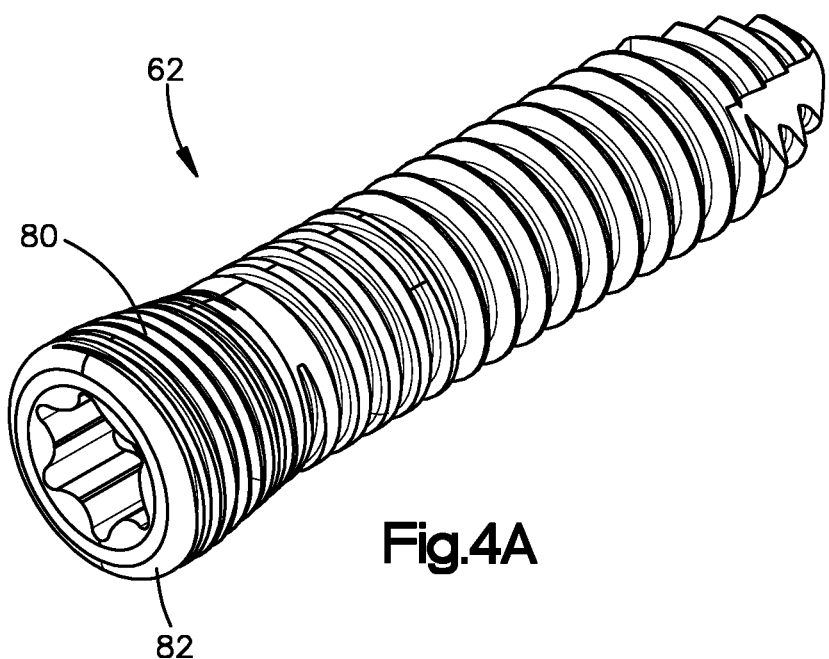
FIG. 4A is a perspective view of one embodiment of the fixation elements that is configured to affix the intervertebral implant shown in FIG. 2 to a vertebral body as illustrated in FIGS. 1A and 1B.
Figure 4B:
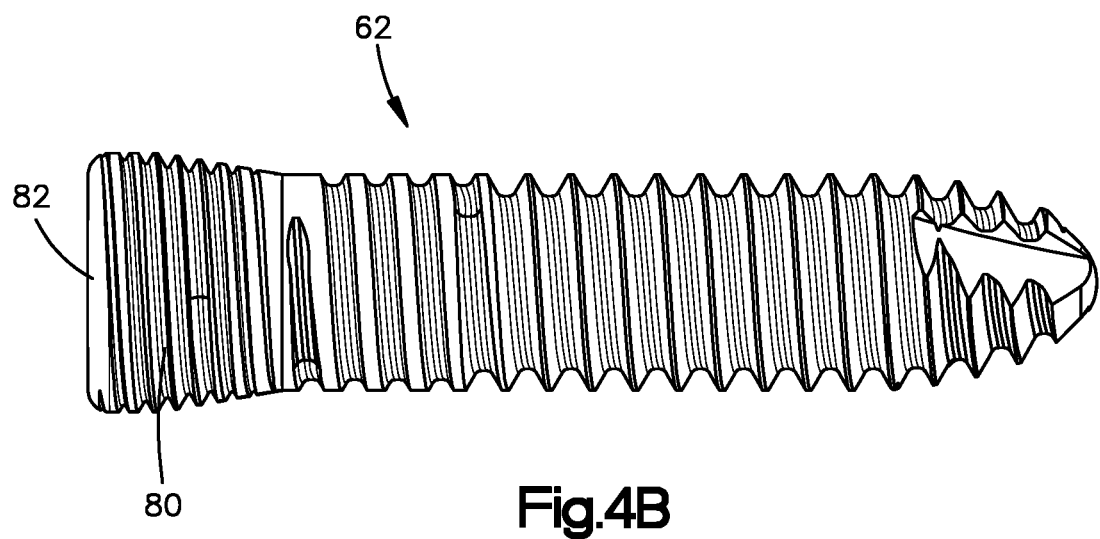
FIG. 4B is a side elevation view of the of the fixation element shown in FIG. 4A.

Referring now to FIG. 3F, and as descried above, the support member 34 can include at least one tab 64, for instance a plurality of tabs 64, that extend from the body 46. In one example, the tabs 64 can include at least a first tab 64*a* and a second tab 64*b* that each extends from the body 35 in the upward or superior direction. Thus, the first and second tabs 64*a* and 64*b* can be referred to as a first pair of tabs. The first tab 64*a* and the second tab 64*b* can be spaced from each other along the lateral direction A, such that the support member 34 defines a first gap 65*a* between the first and second tabs 64*a* and 64*b* along the lateral direction. The first gap 65*a* can be sized or otherwise configured to receive a portion of the first vertebral body when the first and second arms 38 and 42 are inserted into the intervertebral space. In particular, the first tab is spaced from second tab 64*b* by a first distance G1 along the lateral direction A. The first distance G1 can be any distance so long as a portion of the first vertebral body can extend into the gap 65*a*.

With continued reference to FIG. 3F, the tabs 64 can include at least a third tab 64*c* and a fourth tab 64*d* that each extends from the body 35 in the downward or inferior direction. Thus, the third and fourth tabs 64*c* and 64*d* can be referred to as a second pair of tabs. The third tab 64*c* and the fourth tab 64*d* can be spaced from each other along the lateral direction A, such that the support member 34 defines a second gap 65*b* between the third and fourth tabs 64*c* and 64*d* along the lateral direction. The second gap 65*b* can be sized or otherwise configured to receive a portion of the second vertebral body when the first and second arms 38 and 42 are inserted into the intervertebral space. In particular, the third tab 64*c* is spaced from fourth tab 64*d* by a second distance G2 along the lateral direction A. As shown, the second distance G2 can be less than the first distance G1. It should be appreciated, however, that the first and second distances G1 and G2 can substantially the same or the second distance G2 can be greater than the first distance G1, as desired. The first and second tabs 64*a* and 64*b* can be equidistant from a centerline of the frame 26, and the third and fourth tabs 64*c* and 64*d* can be equidistant from the centerline of the frame 26. The centerline of the frame can extend in the transverse direction T and bifurcate the frame 26 in the lateral direction A. It should be appreciated, however, that the tabs 64 can be alternatively positioned as desired. Each of the third and fourth tabs 64*c* and 64*d* can be spaced from the centerline a distance that is less than the distance that each of the first and second tabs 64*a* and 64*b* is spaced from the centerline.

Each of the tabs 64*a*-64*d* defines a front surface and an opposed bone contacting surface. The front surfaces of each tab 64*a*-64*d* can be flush with or otherwise coincident with the outer surface 54 as illustrated. It should be appreciated, however, that the front surfaces can be offset with respect to the outer surface 54 as desired. The bone contacting surfaces of the first and second tabs 64*a* and 64*b* are configured to abut the first vertebral body and the bone contacting surfaces of the third and fourth tabs 64*c* and 64*d* are configured to abut the second vertebral body when the first and second arms 38 and 42 are inserted into the intervertebral space. When the frame 26 is implanted into the intervertebral space, anterior surfaces of the first and second vertebral bodies can extend into the first and second gaps 65*a* and 65*b*. Further, the first and second vertebral bodies can be flush with or extend beyond the front faces of the tabs 64*a*-64*d*. Accordingly, it can be said that the frame 26 provides a zero profile at a centerline of the vertebral bodies when the arms 38 and 42 are inserted into the intervertebral space. The frame 26, and alternative embodiments thereof, are described in U.S. patent application Ser. No. 13/767,097 filed Feb. 14, 2013, the disclosure of which is hereby incorporated by reference as if set forth in its entirety herein.

As shown in FIGS. 5A-5E, the spacer 30 can be coupled to the frame 26 using an actuation instrument 210 that is configured as an expansion instrument. The instrument 210, the frame 26, and in some cases the spacer 30 can together define an intervertebral implant system 214. The expansion instrument 210 includes a grip 212 and a handle 213. The grip 212 is configured as an expansion grip and is configured to apply the first and second expansion forces to the engagement members 170 of the first and second arms 38 and 42.

The first and second expansion forces will elastically expand the first and second arms 38 and 42 of the frame 26 to thereby allow the spacer 30 to be received by the void 94 of the frame 26.

As shown, the instrument 210 includes a first arm 220 that is configured to releasably couple to the first arm 38 of the frame 26, and a second arm 224 that is rotatably coupled to the first arm 220 at a first pivot 228 and is configured to releasably couple to the second arm 42 of the frame 26. The first and second arms 220 and 224 are configured as expansions arms. The first and second expansion arms 220 and 224 are pivotally coupled to each other at the first pivot 228 such that rotation of the first and second expansion arms 220 and 224 about the first pivot 228 causes the first and second arms 38 and 42 of the frame 26 to elastically flex away from each other when the instrument 210 is coupled to the frame 26. Therefore, the instrument 210 is configured to have a first position or configuration whereby the instrument 210 can be coupled to the frame 26, and a second position or configuration whereby the instrument 210 is applying expansion forces to the arms 38 and 42 of the frame 26 so that the frame can receive the spacer 30.

Figure 5A:
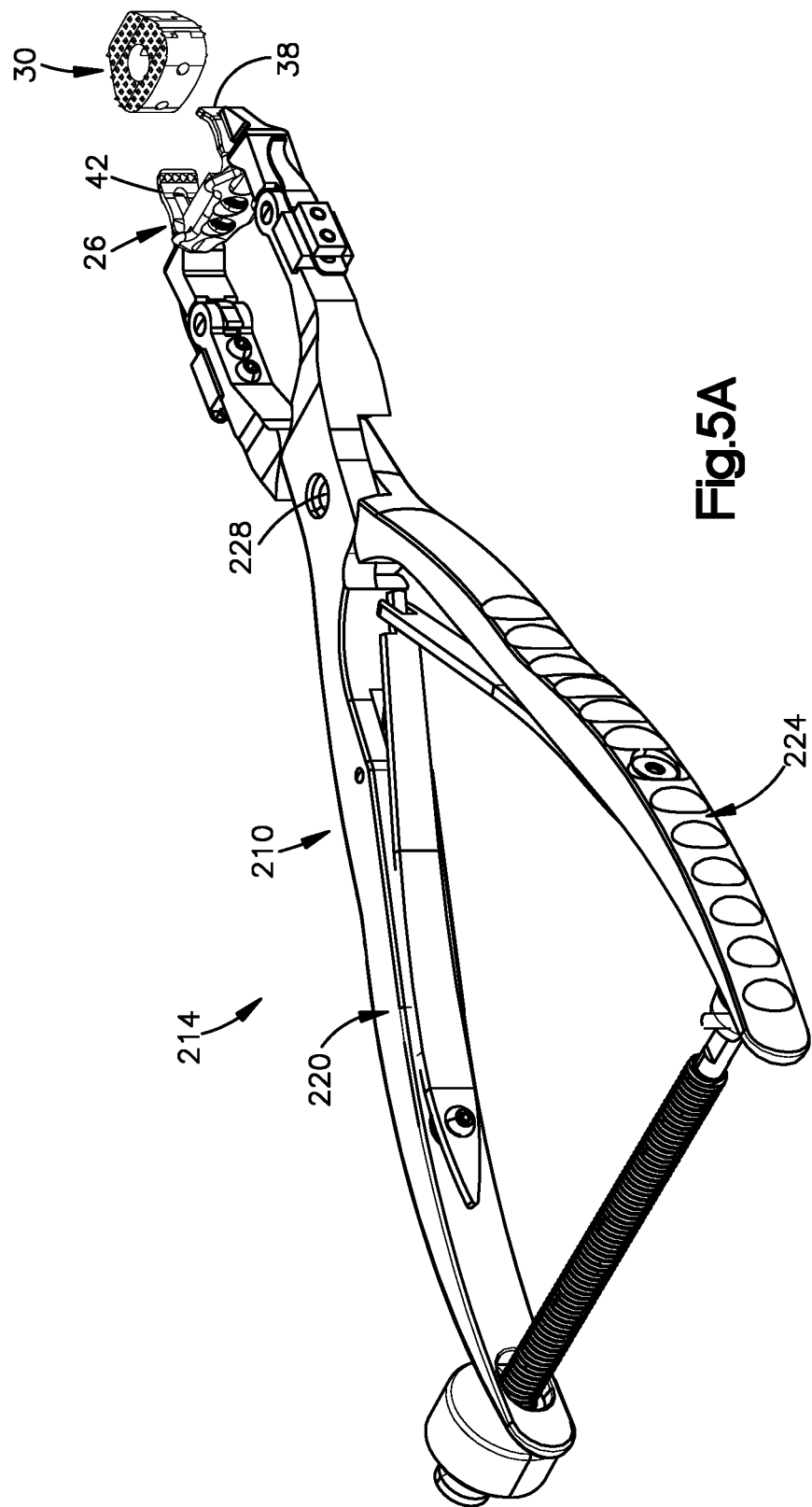
FIG. 5A is a perspective view of an intervertebral implant system constructed in accordance with an embodiment, the system including an actuation instrument configured as an expansion instrument that includes an actuation grip illustrated as an expansion grip that is configured to actuate the frame shown in FIG. 3A from a first configuration to a second configuration whereby the frame is configured to receive a spacer, for example of the type shown in FIG. 2A.
Figure 5B:
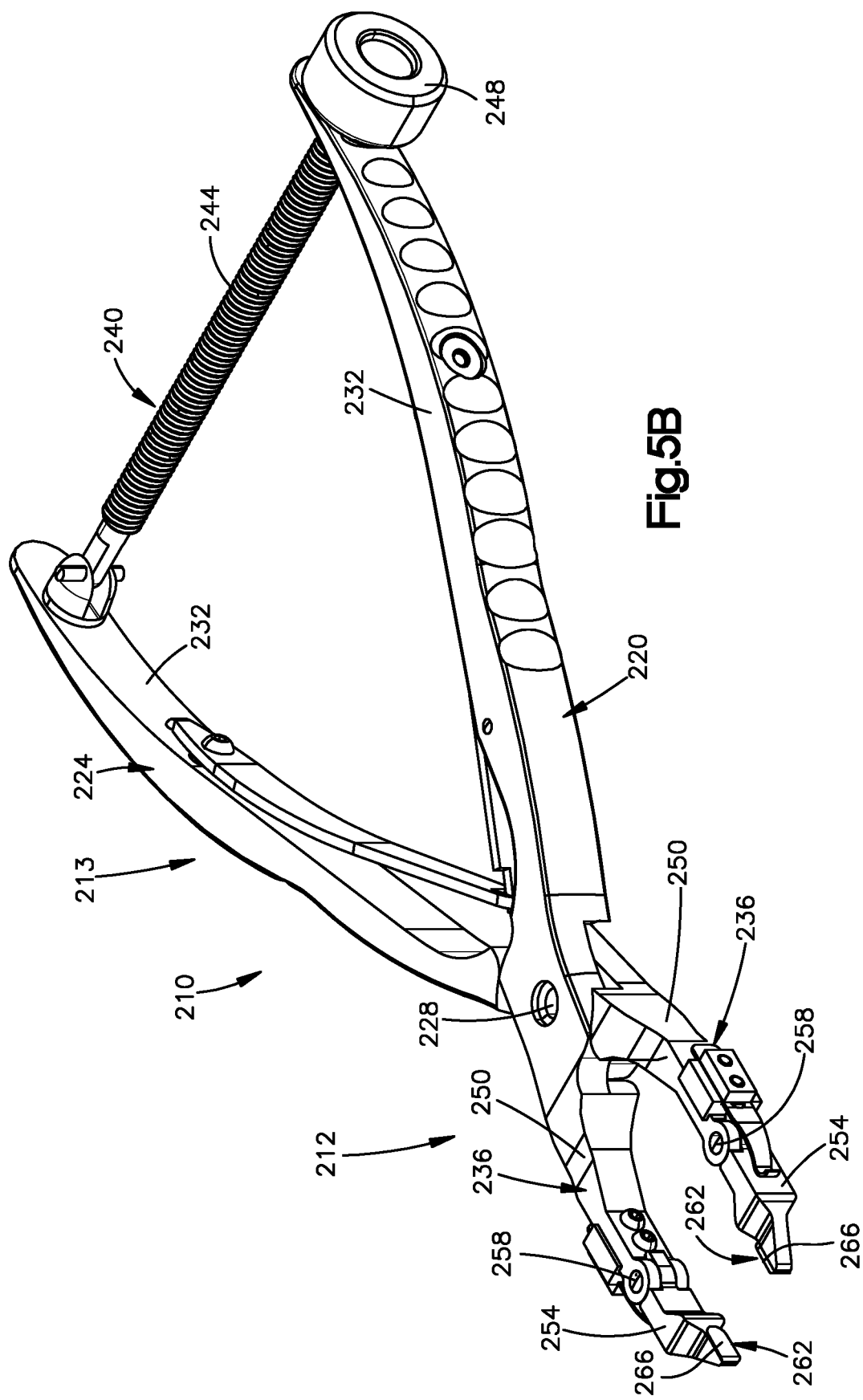
FIG. 5B is a perspective view of the expansion instrument shown in FIG. 5A, the expansion instrument including a first expansion arm and a second expansion arm coupled to the first expansion arm at a first pivot, each expansion arm having a handle portion and a gripping portion that combine to define a handle of the expansion instrument and the expansion grip illustrated in FIG. 5A.

As shown in FIGS. 5B and 5C, each expansion arm 220 and 224 includes a handle portion 232 that extends proximally from the first pivot 228 and a gripping portion 236 that extends distally from the first pivot 228. The handle portions 232 define the handle 213, and the gripping portions 236 define the grip 212. The handle portions 232 are configured to be gripped by an individual such that the handle portions 232 can be squeezed or otherwise moved toward each other. The expansion instrument 210 can further include a handle locking mechanism 240 that is configured to lock the handle portions 232 relative to each other after the handle portions 232 have been moved toward each other. In the illustrated embodiment, the locking mechanism 240 includes a threaded shaft 244 and a nut 248. As at least one of the handle portions 232 is moved along the shaft 244, the nut 248 can be threaded along the shaft 244 to thereby lock the handle portions 232 relative to each other. It should be appreciated, however, that the locking mechanism 240 can include other configurations, as desired. For example, the locking mechanism 240 can have a ratchet configuration.

As shown in FIGS. 5C and 5D, the gripping portions 236 are configured to expand the frame arms as the handle portions 232 are moved toward each other. Each gripping portion 236 includes an extension member 250 that extends distally from the first pivot 228, and a gripping member 254 that is pivotally coupled to a distal end of the extension member 250 at a second pivot 258. Each gripping member 254 includes an engagement member 262 that is configured to engage respective engagement members 170 of the first and second arms 38 and 42 of the frame 26. As shown in FIG. 5D, the engagement members 262 are dove-tailed members 266 that are opposed to each other and are configured to mate with the dove-tailed slots of the first and second arms 38 and 42 to thereby couple the expansion instrument 210 to the frame 26. As shown, each dove-tailed member 266 includes a pair of transversely opposed protrusions 280 that each defines an angled engagement surface 284 that is configured to abut or otherwise contact a respective angled engagement surface 186 of the slots 174 when the engagement members 262 are mated with the engagement members 170. It should be appreciated that the engagement members 262 can have other configurations as desired. For example, the engagement members 262 and the engagement members 170 can be reversed.

As shown in FIG. 5D, a proximal end of each engagement member 262 defines a tapered lead-in portion 270 that allows the engagement members 262 to easily be guided into the openings 178 of the engagement members 170. Therefore, the expansion instrument 210 can easily be coupled to the frame 26 along a direction that is opposite the insertion direction I. That is, if the frame 26 is stationary, the expansion instrument 210 can be coupled to the frame 26 by translating the instrument 210 along a direction that is opposite the insertion direction I.

As shown in FIG. 5C, each gripping member 254 includes a pair of stops 300 that extend proximally toward the extension member 250 and are spaced apart from the extension member 250. As the gripping member 254 rotates about the second pivot 258 the stops 300 will limit the rotation by contacting the extension member 250. Therefore, the angular range in which the gripping members 254 can rotate about the second pivots 258 will depend on the distance in which the stops 300 are spaced apart from the extension members 250.

As shown in FIG. 5C, each gripping portion 236 further includes a biasing member 304 that is configured to bias the gripping members 254 toward each other. In the illustrated embodiment, the biasing members 304 are leaf springs 308 that are coupled to the extension members 250 and urge against an outer surface of the gripping members 304. By biasing the gripping members 254 toward each other, the expansion instrument 210 can more easily and more predictably be coupled to the frame 26. It should be appreciated, however, that the biasing members 304 can have other configurations as desired. For example, the biasing members can be elastically flexible wires and can be disposed within the gripping members 254 as desired.

Figure 5E:
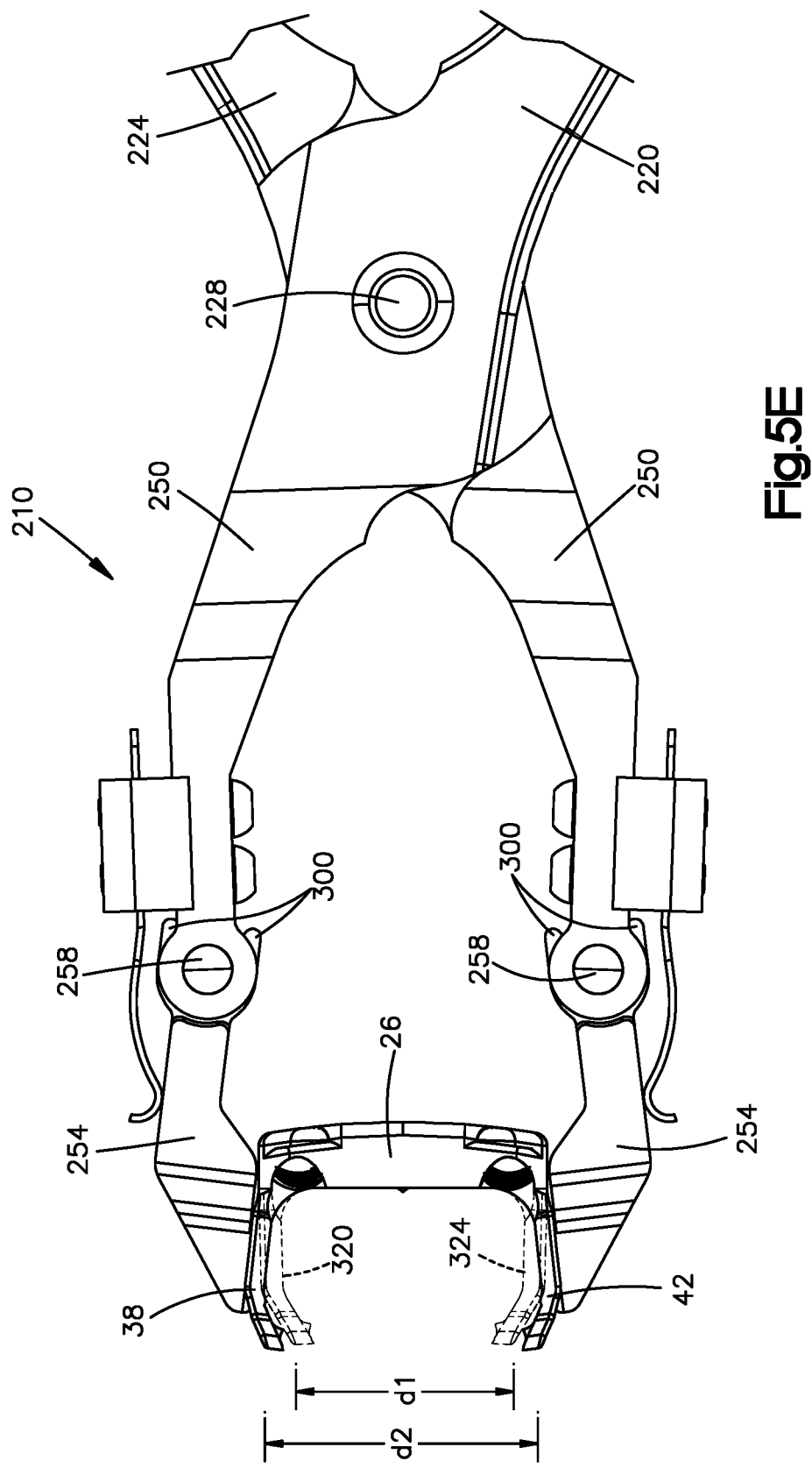
FIG. 5E is an enlarged top plan view of the expansion grip shown in FIG. 5B, coupled to the first and second arms of the frame shown in FIG. 3A, showing the expansion instrument actuated from a first position to a second position, whereby the expansion grip applies an expansion force to the first and second arms of the frame when the expansion instrument is in the second position, the expansion force biasing the first and second arms of the frame to flex away from each other.
Figure 51:
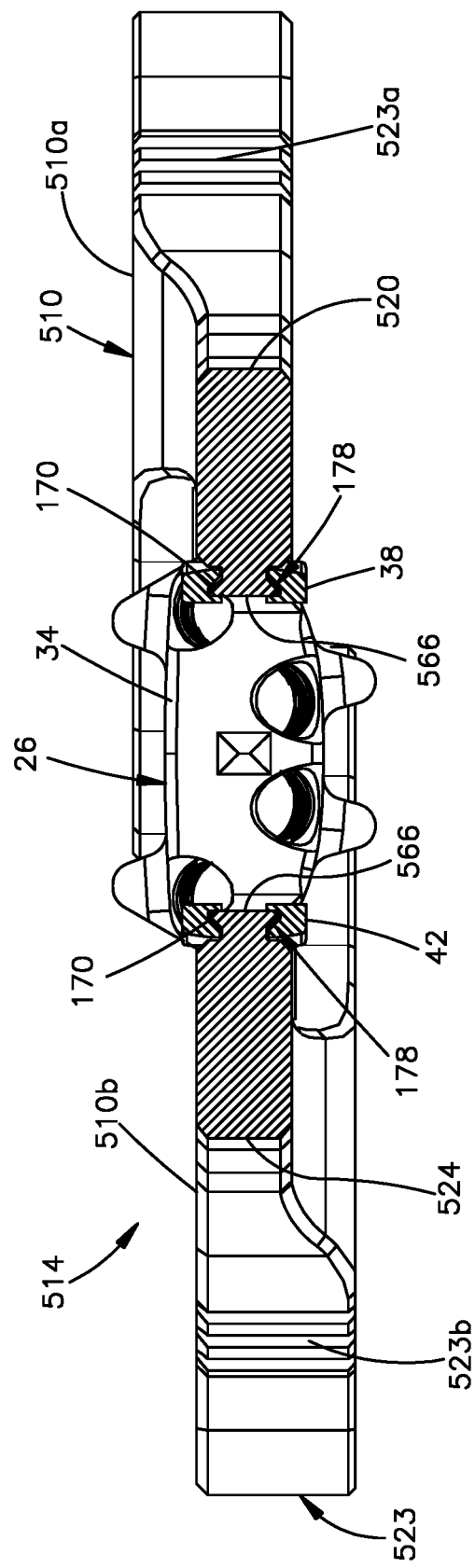
Figure 5J:
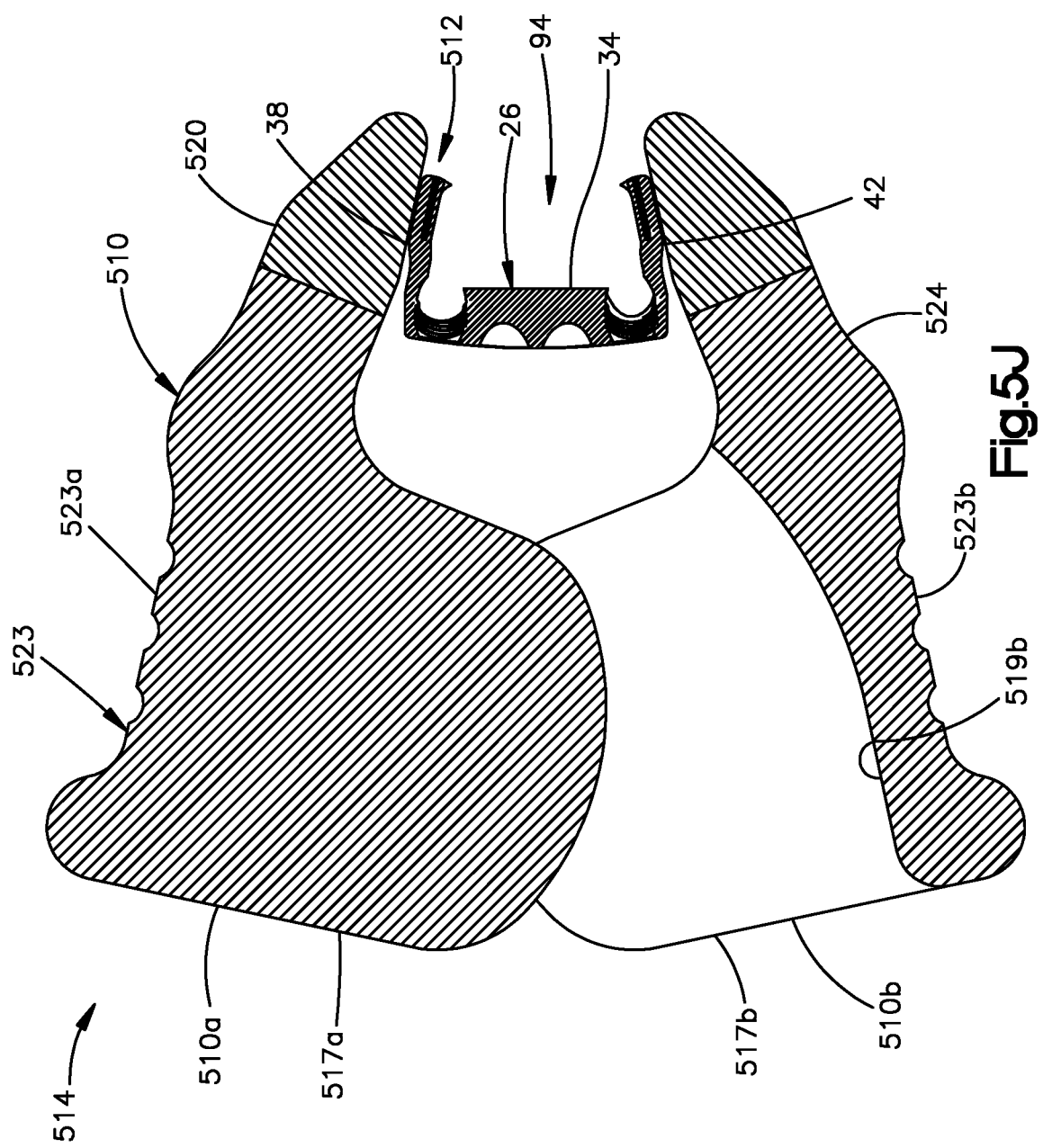
FIG. 5J is a sectional plan view of the expansion instrument illustrated in FIG. 5F, shown coupled to the intervertebral implant frame.

In operation and in reference to FIG. 5E, the expansion instrument 210 is coupled to the frame 26 by placing the engagement members 262 of the instrument 210 distal to the engagement members 170 of the frame 26. By translating or otherwise moving the frame 26 or the instrument 210 toward the other, the engagement members 262 will engage the engagement members 170 to thereby couple the frame 26 to the instrument 210 such that the second pivots 258 of the instrument 210 abut an outer surface of the flexible arms 38 and 42 proximate to the support member 34. By squeezing the handle portions 232 toward each other, the extension member 250 of the first expansion arm 220 will rotate counterclockwise about the first pivot 228 and the gripping member 254 of the first expansion arm 220 will rotate clockwise about the second pivot 258. Conversely, the extension member 250 of the second expansion arm 224 will rotate clockwise about the first pivot 228 and the gripping member 254 of the second expansion arm 224 will rotate counterclockwise about the second pivot 258.

This rotation will cause at least one of the first and second arms 38 and 42 to elastically flex away from the other. For example, the first and second inner spacer contacting surfaces 88 and 92 of the first and second arms 38 and 42 can define respective first and second respective contact locations 320 and 324, and at least one of the first and second arms 38 and 42 is flexible so as to be movable between a first position, whereby the frame 26 defines a first distance $d_1$ that extends along the lateral direction A between the first and second contact locations 320 and 324, and a second position, whereby the frame 26 defines a second distance $d_2$ that extends along the lateral direction A between the first and second contact locations 320 and 324. It should be appreciated that the first and second contact locations 320 and 324 can be located anywhere along the arms 320 and 324 so long as they remain the same when the first and second distances are measured.

As shown in FIG. 5E, the second distance $d_2$ is greater than the first distance $d_1$ such that when in the second position, the void 94 defines a cross-sectional dimension that is greater than that of the spacer 30 such that the void 94 is sized to receive the spacer 30. While the arms 38 and 42 are elastically flexed, at least one of the arms 38 and 42 is biased toward the first position. Therefore, when the handle portions 232 of the instrument 210 are released, the arms 38 and 42 will flex back to a third position, and when in the third position, the frame 26 defines a third distance $d_3$ that extends along the lateral direction A between the first and second contact locations 320 and 324 and is less than the second distance $d_2$ (See FIG. 2B). When in the third position at least one of the first and second inner contacting surfaces 88 and 92 of the arms 38 and 42 will apply a retention force against the spacer 30 along a direction toward the other of the first and second inner spacer contacting surfaces 88 and 92.

Referring now to FIGS. 5F-5J, the spacer 30 can be coupled to the frame 26 using an actuation instrument 510 that is configured as an expansion instrument in accordance with an alternative embodiment. Thus, the instrument 510, the frame 26, and in some cases the spacer 30 can together define an intervertebral implant system 514. The expansion instrument 510 includes first and second members 510a and 510b that are configured to engage each other so as to define a grip 512 and a handle 523. The grip 512 is configured as an expansion grip and is configured to apply the first and second expansion forces to the engagement members 170 of the first and second arms 38 and 42. The first and second expansion forces will elastically expand the first and second arms 38 and 42 of the frame 26 to thereby allow the spacer 30 to be received by the void 94 of the frame 26.

As shown, the first member 510a includes a first arm 520 that is configured to releasably couple to the first arm 38 of the frame 26. The second member 510b includes a second arm 524 that is configured to releasably couple to the second arm 42 of the frame 26. The first and second arms 520 and 524 are configured as expansions arms. The first and second expansion arms 520 and 524 are pivotally coupled to each other such that rotation of the first and second expansion arms 520 and 524 with respect to each other about respective pivot locations causes the first and second arms 38 and 42 of the frame 26 to elastically flex away from each other when the instrument 510 is coupled to the frame 26. Therefore, the instrument 510 is configured to have a first position or configuration whereby the instrument 510 can be coupled to the frame 26, and a second position or configuration whereby the instrument 510 is applying expansion forces to the arms 38 and 42 of the frame 26 so that the frame can receive the spacer 30.

The first member 510a defines a first base 511a, such that the first arm 520 generally extends from the first base 511a in a distal direction. The first arm 520 can be monolithic with the first base 511a. For instance, the first base 511a and the first arm 520 can be made from the same material. The material can be metal. Alternatively, the material can be plastic. Alternatively, the first arm 520 can be attached to the first base 511a in any manner desired. In this regard, the first base 511a and the first arm 520 can be made from different materials. For example, the first base 511a can be plastic, and the first arm 520 can be a metal. Alternatively, the first base 511a can a metal, and the first arm 520 can be a plastic. The first member 510a can define a first gap 513a that extends into the first base so as to define corresponding first and second portions 515a and 517a that are separated from each other by the first gap 513a. The first member portion 515a can be an upper portion, and the second portion 517a can be a lower portion that is spaced from the upper portion 515a in a downward direction. At least a portion of the first gap 513a can extend into the first base 511a but not through the first base 511a, so as to terminate at a first stop wall 519a.

Similarly, the second member 510b defines a second base 511b, such that the second arm 524 generally extends from the second base 511b in the distal direction. The second arm 524 can be monolithic with the second base 511b. For instance, the second base 511b and the second arm 524 can be made from the same material. The material can be metal. Alternatively, the material can be plastic. Alternatively, the second arm 524 can be attached to the second base 511b in any manner desired. In this regard, the second base 511b and the second arm 524 can be made from different materials. For example, the second base 511b can be plastic, and the second arm 524 can be a metal. Alternatively, the second base 511b can a metal, and the second arm 524 can be a plastic. The second member 510b can define a second gap 513b that extends into the second base so as to define corresponding first and second portions 515b and 517b that are separated from each other by the second gap 513b. The first member portion 515b can be an upper portion, and the second portion 517b can be a lower portion that is spaced from the upper portion 515b in the downward direction. At least a portion of the second gap 513b can extend into the second base 511b but not through the second base 511b, so as to terminate at a second stop wall 519b.

The first gap 513a can be sized to receive the first portion 515b of the second member 510b. Alternatively or additionally, the first gap 513 can be sized to receive the second portion 517b of the second member 510b. Similarly, the second gap 513b can be sized to simultaneously receive the first portion 515a of the first member 510a. Alternatively or additionally, the second gap 513b can be sized to simultaneously receive the second portion 517a of the first member 510a. In accordance with one embodiment, the first gap 513a is sized to receive the first portion 515b of the second member 510b, and the second gap 513b is sized to simultaneously receive the second portion 517a of the first member 510a. The first and second bases 511a and 511b slide relative to each other so as to cause the respective first and second arms 520 and 524 to move away from each other. Otherwise stated, the first and second bases 511a and 511b can pivot with respect to each other about a pivot location that translates as the first and second bases 511a and 511b translate with respect to each other.

The first arm 520 is configured to releasably couple to the first arm 38 of the frame 26 such that the first member 510a abuts a first side of the frame 26 at a first abutment. The second arm 524 is configured to releasably couple to the second arm 42 of the frame 26 such that the second member 510b abuts a second side of the frame 26 at a second abutment. The second side of the frame 26 is opposite the first side of the frame 26 with respect to the lateral direction. In accordance with one embodiment, the first arm 520 is configured to releasably couple to the first arm 38 of the frame 26 such that the first member 510a abuts a first side of the support member 34 at the first abutment. The second arm 524 is configured to releasably couple to the second arm 42 of the frame 26 such that the second member 510b abuts a second side of the support member 34 at the second abutment. The first and second members 510a and 510b of the instrument 510 can be identical to each other in one embodiment. Alternatively, the first and second abutments can be defined by proximal ends of the first and second arms 38 and 42, respectively.

The first and second members 510a and 510b can define first and second handle portions 523a and 523b, respectively, that define the handle 523 of the instrument 510. During operation, the handle portions 523a and 523b can be moved toward each other, thereby causing the first gap 513a to further receive the respective portion of the second member 510b, and the second gap 513b to further receive the respective portion of the first member 510a. The handle portions 523a and 523b can define grips that are engaged and receive a force that biases each of the handle portions 523a and 523b toward the other of the handle portions 523a and 523b. As the first and second members 510a and 510b are moved toward each other, the first member 510a pivots about the first abutment, and the second member 510b pivots about the second abutment, thereby causing the first and second arms 520 and 524 to move away from each other. When the first and second arms 520 and 524 are coupled to the first and second arms 38 and 42, respectively, of the frame 26, movement of the first and second arms 520a and 524 away from each other causes the first and second arms 38 and 42 to move from the first position to the second position described above.

The instrument 510 can include a force limiter that limits the amount of force applied to the first and second arms 38 and 42 of the frame 26 that expands the first and second arms 38 and 42 from the first position to the second position. In particular, the portion of the second member 510b that is received in the first gap 513a is configured to abut the first stop wall 519a, thereby preventing additional movement of the handle portions 523a and 523b toward each other. Alternatively or additionally, the portion of the first member 510a that is received in the second gap 513b is configured to abut the second stop wall 519b, thereby preventing additional movement of the handle portions 523a and 523b toward each other. Thus, during operation, the handle portions 523a and 523b can be moved toward each other until one or both of the first and second members 510a and 510b abuts the second and first stop walls 519b and 519a, respectively.

As described above, the first and second arms 520 and 524 of the instrument 510 is configured to releasably couple to the first and second arms 38 and 42, respectively, of the frame 26 such that movement of the first and second arms 520 and 524 away from each other applies a first to the first and second arms 38 and 42 that causes the first and second arms 38 and 42 to move from the first position to the second position. In particular, the instrument 510 defines a grip 512 that is configured to releasably couple to the engagement members 170 of the first and second arms 38 and 42, respectively, of the frame 26. The grip 512 can include gripping portions supported by the first and second arms 520 and 524, respectively, that are configured to releasably couple to the engagement members 170 of the first and second arms 38 and 42, respectively, of the frame 26. The gripping portions 536 are configured to expand the frame arms 38 and 42 as the handle portions 523a and 523b are moved toward each other.

Each gripping portion 536, and thus each of the first and second arms 520 and 524, can include an engagement member 562 that is configured to engage the respective engagement members 170 of the first and second arms 38 and 42 of the frame 26, thereby attaching the arms 520 and 524 to the first and second arms 38 and 42, respectively. The engagement members 562 can be dove-tailed members 566 that are opposed to each other and are configured to mate with the dove-tailed slots of the first and second arms 38 and 42 to thereby releasably couple the expansion instrument 510 to the frame 26. As shown, each of the dove-tailed members 566 includes a protrusion 580 such that the protrusions 580 are opposite each other. Each of the protrusions 580 defines an angled engagement surface 584 that is configured to abut or otherwise contact a respective angled engagement surface 186 of the slots 174 when the engagement members 562 are mated with the engagement members 170. It should be appreciated that the engagement members 562 can have other configurations as desired. For example, the geometry of the engagement members 562 and the engagement members 170 can be reversed. A proximal end of each engagement member 562 can define a tapered lead-in portion 570 that allows the engagement members 562 to easily be guided into the openings 178 of the engagement members 170. Therefore, the expansion instrument 510 can be inserted into the openings 178 in a first direction so as to releasably couple the instrument 510 to the frame 26. Similarly, the expansion instrument 510 can be removed from the openings 178 in a second direction opposite the first direction so as to decouple the instrument 510 from the frame 26. It should be appreciated that the expansion instrument 510 can be assembled with the frame 26, and that the frame 26 can retain the spacer 30 or not retain the spacer 30 when the expansion instrument is assembled with the frame 26.

Referring to FIGS. 6A-6D, and the spacer 30 defines a proximal end surface 30a and a distal end surface 30b that is spaced from the proximal end surface 30a along the longitudinal direction L. For instance, the distal end surface 30b is spaced from the proximal end surface 30a in the distal direction. Thus, the distal end surface 30b can be spaced from the proximal end 30a in the insertion direction of the spacer 30 into the intervertebral space. Accordingly, the distal end surface 30b can be spaced from the proximal end 30a in the insertion direction of the intervertebral implant 22 into the intervertebral space. It should be appreciated that, when the implant 22, and thus the spacer 30, is implanted in the intervertebral space, the distal end surface 30b is spaced posteriorly from the proximal end surface 30a.

The spacer 30 further defines a pair of opposed side surfaces 30c spaced from each other along the lateral direction A. Each of the side surfaces 30c further extends from the proximal end surface 30a to the distal end surface 30b. When the frame 26 is attached to the spacer 30 (see FIGS. 2A-B and 11B-C), the support member 34 can extend along the proximal end surface 30a, and the arms 38 and 42 can extend along at least a portion up to an entirety of the length along the longitudinal direction L of respective different ones of the sides 30c. It should be appreciated that the surfaces 30a-30e can be sized and shaped as desired. For instance at least one or more up to all of the surfaces 30a-30e can be planar, curved, bent, or otherwise non-planar as desired.

The spacer 30 further defines a top surface 30d and a bottom surface 30e spaced from the top surface 30d along the transverse direction T. For instance, the top surface 30d is spaced upward with respect to the bottom surface 30e. Thus, the top surface 30d is configured to face the superior vertebral surface 14a of the superior vertebral body 10a, and contact the superior vertebral surface 14a of the superior vertebral body 10a. The bottom surface 30e is configured to face the inferior vertebral surface 14b of the inferior vertebral body 10b, and contact the inferior vertebral surface 14b of the inferior vertebral body 10b. The spacer 30 can define a height from the top surface 30c to the bottom surface 30d in the transverse direction T. The spacer can further define a length from the proximal end surface 30a to the distal end surface 30b in the longitudinal direction. The distal end surface 30b can define a first width along the lateral direction A that is less than a second width along the lateral direction A of the proximal end surface 30a. Each of the first and second widths can extend along the lateral direction A from one of the side surfaces 30c to the other of the side surfaces 30c. At least one or both of the first and second widths can be greater than the height and less than the length.

As described above, the spacer 30 can be made from a bone graft material such as allograft bone, autograft bone, or xenograft bone, for example. For instance, the spacer 30 can include a cortical spacer body 410 and a cancellous spacer body 412. The cortical spacer body 410 can define at least a portion up to an entirety of the distal end surface 30b. The cancellous spacer body 412 can define at least a portion up to an entirety of the proximal end surface 30a. It will be appreciated that the a fixation member, such as a screw, that is inserted through the fixation element receiving aperture 58 (see FIGS. 3A-3C) toward the spacer 30 travels from the support member 34 and through the cancellous spacer body 412, and thus through the cancellous bone graft material, without passing through cortical spacer body 410, and thus without passing through any of the cortical bone graft material. Thus, a straight line passing centrally through the fixation element receiving apertures 58 is aligned with the cancellous spacer body 412 without first passing through the cortical spacer body 410. The cortical spacer body 410 can further define a first portion of one or both of the side surfaces 30c, and the cancellous spacer body 412 can define a second portion of one or both of the side surfaces 30c. The first portion of the side surfaces 30c can be distal with respect to the second portion of the side surfaces 30c. Similarly, the cortical spacer body 410 can further define a first portion of either or both of the top and bottom surfaces 30d and 30e. The cancellous spacer body 412 can define a second portion of either or both of the top and bottom surfaces 30d and 30e. The first portion of the top and bottom surfaces 30d and 30e can be distal with respect to the second portion of the top and bottom surfaces 30d and 30e.

The cortical spacer body 410 and the cancellous spacer body 412 are configured to abut each other so as to define the spacer 30. For instance, the cortical spacer body 410 can include an engagement member 414, and the cancellous spacer body 412 can include an engagement member 416 that is configured to engage with the engagement member 414 of the cortical spacer body 410 so as to join the cortical spacer body 410 to the cancellous spacer body 412. In this regard, the engagement member 414 of the cortical spacer body 410 can be referred to as a first engagement member, and the engagement member 416 of the cancellous spacer body 412 can be referred to as a second engagement member. The first engagement member 414 can be disposed distal with respect to the second engagement member 416. Further, the first and second engagement members 414 and 416 can overlap along the longitudinal direction L such that a straight line that extends in the distal direction from the proximal end surface 30a can pass through both the first engagement member 414 and the second engagement member 416.

In accordance with one embodiment, the first engagement member 414 can define a recess 419, and the second engagement member 416 be configured as a projection 420 that is sized to be received in the recess 419. Otherwise stated, the recess 419 is sized to receive the projection 420.

Thus, the recess 419 defined by the first engagement member 414 is sized to receive the second engagement member 416. The first engagement member 414 can be defined by a base 414a and a pair of necked portions 414b that extend out from the base 414a in the distal direction and project inward in opposite directions toward each other along the lateral direction A. The base 414a and the necked portions 414b can define the recess 419. The recess 419 can extend through the cortical spacer body 410 along the transverse direction T. The second engagement member 416 can include a base 416a and at least one wing 416b, such as a pair of wings 416b, that extend from the base 416a in the proximal direction, and project out with respect to the stem 416a in opposite directions away from each other along the lateral direction A. The wings 416b can thus be disposed between the necked portions 414b and the base 414a. Similarly, the necked portions 414b can be disposed between the wings 416b and the base 416a. Accordingly, the second engagement member 416 is surrounded by the first engagement member 414 along the lateral direction A and in the distal direction. Otherwise stated, the first engagement member 414 surrounds the second engagement member 416 along the lateral direction A and in the distal direction. It can thus be said that the cortical spacer body 410 can partially surround the cancellous body portion 412.

Thus, when the first and second engagement members 414 and 416 engage each other so as to join the cortical spacer body 410 to the cancellous spacer body 412, the engagement members 414 and 416 interfere with each other along both the longitudinal direction L and the lateral direction A. The interference thus prevents removal of the cortical spacer body 410 and the cancellous spacer body 412 along the longitudinal and lateral directions. Rather, in order to remove the cortical spacer body 410 and the cancellous spacer body 412 from each other, the cortical spacer body 410 and the cancellous spacer body 412 are moved with respect to each other along the transverse direction T until the engagement members 414 and 416 are removed from interference with each other.

It is recognized that the cortical spacer body 410 provides structural rigidity to the spacer 30, and the cancellous spacer body 412 promotes bony ingrowth of the first and second vertebral bodies into the cancellous spacer body 412. Accordingly, it is desirable to provide a sufficiently high surface area of cancellous spacer body 412 at the top surface 30d and the bottom surface 30e to promote adequate boney ingrowth while providing a sufficient volume of cortical spacer body 412 to provide adequate structural rigidity for the spacer 30. The spacer 30, constructed in accordance with various embodiments described herein in with reference to FIGS. 6A-12E, can have a surface area of cancellous bone within a first range between and including approximately 40% and approximately 85% at either or both of the top and bottom surfaces 30d and 30e. For instance, the first range can be between and include approximately 40% and 75%, including approximately 55% and 70%. Thus, it can be said that either or both of the top and bottom surfaces 30d and 30e can have a surface area, and a majority of the surface area can be defined by the cancellous spacer body 412. A minority of the surface area can be defined by the cortical spacer body 410.

As illustrated in FIG. 6A, the cortical spacer body 410 can define a surface area at each of the top and bottom surfaces 30d and 30e as desired, for instance between 35 mm$^2$ and 60 mm$^2$, including between 40 mm$^2$ and 50 mm$^2$, for instance approximately 46 mm$^2$. The cancellous spacer body 412 can define a surface area at each of the top and bottom surfaces 30d and 30e as desired, for instance between 50 mm$^2$ and 100 mm$^2$, including between 70 mm$^2$ and 90 mm$^2$, for instance approximately 816 mm$^2$. The spacer 30, constructed in accordance with various embodiments described herein in with reference to FIGS. 6A-12E, can have any height from the top surface 30c to the bottom surface 30d as desired. It should be appreciated that the spacers 30, and thus the intervertebral implants 22, described herein can be sized as desired to be inserted into an intervertebral spacer at any location along the spine, including the cervical region, the thoracic region, and the lumbar region.

The spacer 30 further defines a force transfer channel 418 that extends through the cancellous spacer body 412. The force transfer channel 418 can terminate at the cortical spacer body 410. Alternatively, the channel 418 can extend at least into the cortical spacer body 410. For instance, the channel 418 can terminate in the cortical spacer body 410. Alternatively, the channel 418 can extend through the cortical spacer body 410. The channel 418 can have a first opening 418a defined by the proximal end surface 30a. Accordingly, the channel 418 can have a first end defined by the first opening 418a. The first opening 418a can be an enclosed opening. That is, the first opening 418a can be enclosed by the proximal end surface 30a along a plane defined by the lateral direction A and the transverse direction T. The first opening 418a can be sized to receive the abutment member 73 of the frame 26 when the frame 26 is attached to the spacer 30. Thus, the abutment member 73 can extend from the first opening 418a into the channel 418 in the distal direction.

Figure 6K:
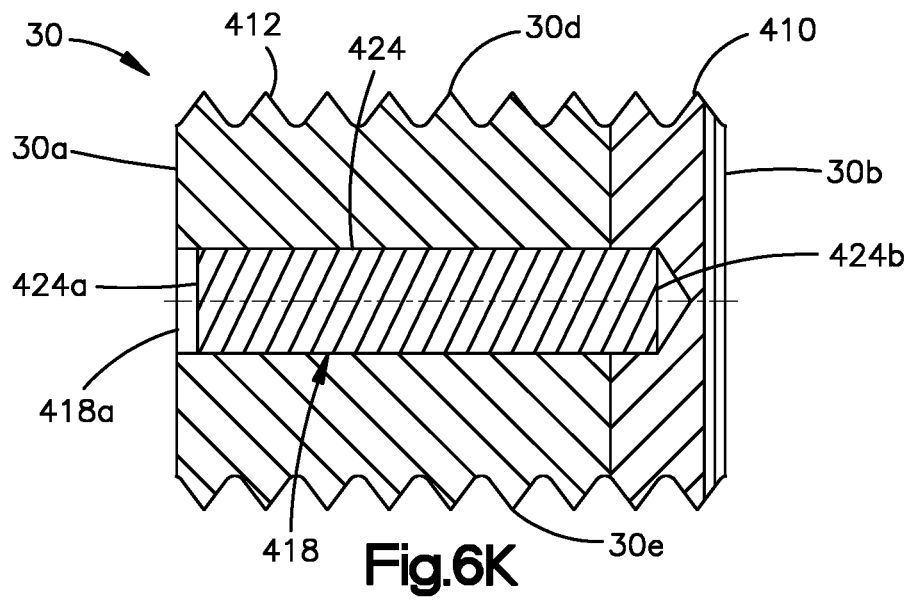
FIG. 6K is a sectional side elevation view of the spacer as illustrated in FIG. 6A, but including parallel top and bottom surfaces.
Figure 6L:
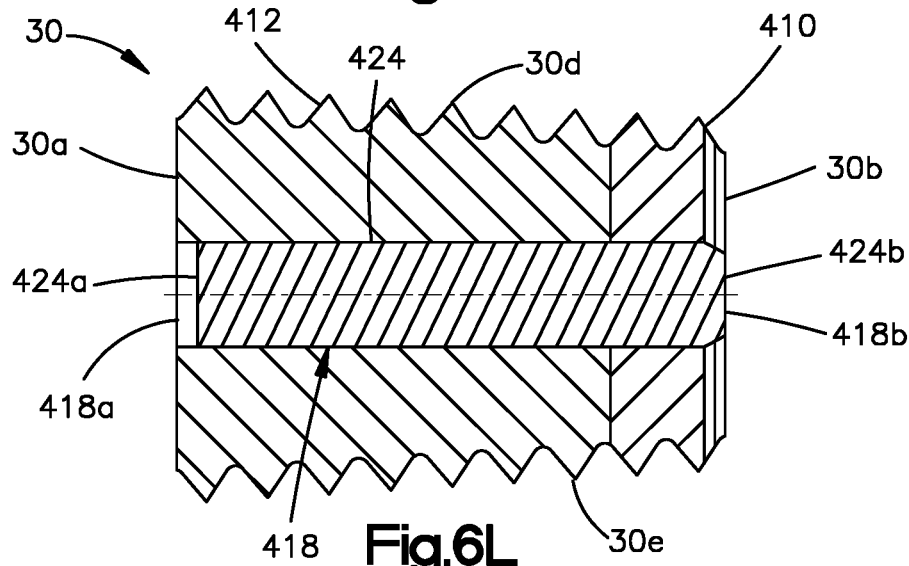
FIG. 6L is a sectional side elevation view of the spacer illustrated in FIG. 6A, but showing an aperture extending through the cortical spacer body and including angled (e.g. lordotic) top and bottom surfaces.
Figure 6M:
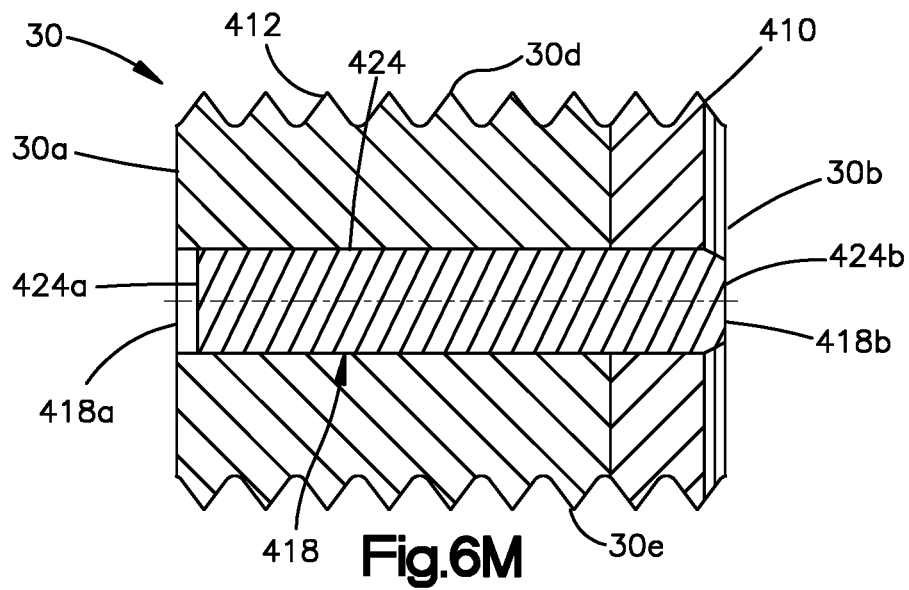
FIG. 6M is a sectional side elevation view of the spacer illustrated in FIG. 6L, but including parallel top and bottom surfaces.

The channel 418 has a second end opposite the first end. The second end of the channel 418 can be terminate within the cortical spacer body 410 as illustrated in FIGS. 6D and 6K, such that the first opening 418a is the only opening of the aperture. Alternatively, as illustrated in FIGS. 6L and 6M, the channel 418 can have a second opening 418b defined by the distal end surface 30b. Thus, the second end of the channel 418 can be defined by the second opening 418b. The channel 418 can therefore extend from the proximal end surface 30a to the distal end surface 30b. The second opening 418b can be an enclosed opening. That is, the second opening 418b can be enclosed by the distal end surface 30b along a plane defined by the lateral direction A and the transverse direction T. Alternatively, the second end of the channel 418 can terminate at the cortical spacer body 410. Thus, the second opening 418b can be defined by the cancellous spacer body 412. In one example, an entirety of the channel 418 can be enclosed by the spacer 30. That is, the entirety of the channel 418 can be enclosed between the first end of the channel 418 and the second end of the channel 418 along a plane defined by the lateral direction A and the transverse direction T. It should be appreciated, however, that at least one up to all of the first opening 418a, the second opening 418b, and at least a portion up to an entirety of the channel 418 between the first and second openings 418a and 418b can be open, and thus not completely enclosed, along a plane defined by the lateral direction A and the transverse direction T.

In one example, the channel 418 can define a central axis of elongation 422 that is equidistant with respect to each of the side surfaces 30c. The central axis of elongation 422 can therefore bifurcate the spacer 30 into two equal halves along the lateral direction A. Thus, the central axis of elongation can be oriented in the longitudinal direction L. It should be appreciated, however, that the central axis of elongation 422 can be oriented in any suitable alternative direction as desired. For instance, the central axis of elongation 422 can be elongate in a direction that includes a directional component in the longitudinal direction L, and one or more directional components in either or both of the lateral direction A and the transverse direction T. The channel 418 can be cylindrical or can define any suitable alternative shape as desired.

With continuing reference to FIGS. 6A-6J, the spacer 30 further includes a force transfer member 424 that is configured to be inserted into the channel 418. Thus, the channel 418 is sized and configured to receive the force transfer member 424. The force transfer member 424 can be made of any suitable biocompatible material having a hardness greater than the cancellous spacer body 412. For instance, the force transfer member 424 can be made of cortical bone, titanium, steel, PEEK, a polymer, ceramics, chronOs, CoCr (or other implantable metals), ultra high molecular weight polyethylene (UHMWPE), poly ether ether ketone (PEKK), Carbon-fiber reinforced poly ether ether ketone (PEEK), other suitable implantable polymers, or the like. The force transfer member 424 defines a first end 424a and a second end 424b opposite the first end 424a. The force transfer member 424 can define a length from the first end 424a to the second end 424b that is less than or equal to the length of the channel 418. The length can be straight and linear from the first end 424a to the second end 424b. The force transfer member 424 can be cylindrical in one embodiment. For instance, the force transfer member 424 can be configured as a dowel. When the force transfer member 424 is disposed in the channel 418, the first end 424a can be positioned adjacent the first opening 418a. In one example, the first end 424a can be recessed with respect to the first opening 418a along the distal direction. In another example, the first end 424a can be flush with the proximal end surface 30a. Thus, the first end 424a can define a surface geometry that matches the surface geometry of the proximal end surface 30. It should be appreciated that the spacers described herein can include as many force transfer members 424 as desired. Further, the first end 424a of one or more of the force transfer members 424 can be recessed with respect to the first opening 418a in the distal direction. Alternatively or additionally, the first end 424a of one or more of the force transfer members 424 can be flush with the proximal end surface 30a. Referring also to FIG. 3C, the abutment member 73 can contact the first end 424a when the frame 26 is attached to the spacer 30, and the force transfer member 424 is disposed in the channel 418. For instance, the abutment member 73 can be in abutment with the first end 424a along the longitudinal direction L.

Further, when the force transfer member 424 is disposed in the channel 418, the second end 424b can be in contact with the cortical spacer body 410. In one example, the second end 424b can be positioned at or adjacent the second end of the channel 418. As described above, the second end of the aperture can terminate at the cortical spacer body 410 or in the cortical spacer body 410. As a result, the second end 424b of the force transfer member can be in contact with the cortical spacer body 410. For instance, the second end 424b can be in abutment with the cortical spacer body 410 along the direction of elongation of the force transfer member 424, such as the longitudinal direction L. Alternatively or additionally, the second end 424b can be embedded in the cortical spacer body 410. Thus, the second end 424b can be press-fit in the channel 418 so as to contact the cortical spacer body 410. The second end 424b can be disposed at the second end of the channel 418. Alternatively, the second end 424b can be recessed with respect to the second end of the channel 418, and the distal end surface 30b, along the proximal direction. As described above, the channel 418 can alternatively extend through the spacer body from the proximal end surface 30a to the distal end surface 30b so as to define first and second openings 418a and 418b. The second end 424b of the force transfer member 424 can extend to the second opening 418b, and can thus be flush with the distal end surface 30b. Accordingly, the force transfer member 424 can be press-fit in the channel 418 at the cortical spacer body 410.

During operation, as the intervertebral implant 22 is inserted into the intervertebral space, the outer surface 54 of the body 46 of the support member 34 may be impacted by an impaction tool or the like in order to advance the implant 22 into the intervertebral space. Because the abutment member 73 is in contact with the force transfer member 424, for instance in abutment contact or in press-fit contact, or both, impaction forces is transferred from the frame 26, to the force transfer member 424, through the force transfer member 424, and to the cortical spacer body 410. Thus, though the support member 34 is positioned adjacent the cancellous spacer body 412, a substantial majority up to a substantial entirety of the impaction forces are absorbed by the cortical spacer body 412, which has a rigidity greater than that of the cancellous spacer body 412.

Thus, the intervertebral implant can be fabricated by engaging the engagement member 414 of the cortical spacer body 410 with the engagement member 416 of the cancellous spacer body 412, inserting the second end 424b of the force transfer member 424 into the first opening 418a of the force transfer channel 418, inserting the force transfer member 424 in the channel in the distal direction until the second end 424b contacts the cortical spacer body 410, and attaching the frame 26 to the spacer 30 such that the support member 34 extends along the proximal end surface 30a, the abutment member 73 abuts the first end 424a of the force transfer member and the first and second arms 38 and 42 engage so as to attach to the respective side surfaces 30c at the cortical spacer body 410.

It should be appreciated, as illustrated in FIGS. 6D and 6L that the top surface 30c and the bottom surface 30 can converge toward each other along the distal direction at an angle G. The angle G can be between 2 degrees and 15 degrees, for instance between 5 degrees and 10 degrees, for instance approximately 7 degrees. Thus, the top and bottom surfaces 30d and 30e can be geometrically configured to restore lordotic curvature to the vertebral bodies. Alternatively, as illustrated in FIGS. 6K and 6M, the top and bottom surfaces 30d and 30e can be parallel to each other along the longitudinal direction L.

Referring now to FIG. 6A and FIGS. 7A-7E, either or both of the top and bottom surfaces 30d and 30e can be smooth or can include any surface geometry as desired. The surface geometry can increase the surface area of the respective top and bottom surfaces 30d and 30e, thereby promoting bony ingrowth of the vertebral bodies into the top and bottom surfaces 30d and 30e. Further, the surface geometry can increase frictional forces between the top and bottom surfaces 10d and 10e and the respective superior and inferior surfaces 14a and 14b, thereby promoting stabilization of the spacer 30 within the intervertebral space. For instance, as illustrated in FIGS. 6A and 6D, the surface geometry can define elongate ridges 426. Each of the ridges 426 can extend out from a respective base 426a to a respective peak 426b. The ridges can be tapered from the base 426a to the peak 426b. For instance the peak 426b can be a pointed peak or a rounded peak. The ridges 426 can be oriented parallel to each other, or angularly offset with respect to each other as desired. For instance, the ridges 426 can be elongate along the lateral direction A, or any suitable alternative direction as desired. For instance, the ridges 426 can be elongate along the longitudinal direction L. Alternatively, the ridges 426 can be elongate along a direction angularly offset with respect to each of the lateral direction A and the longitudinal direction L. The ridges 426 can extend between the side surfaces 30c. For instance, the ridges 426 can extend from one of the side surfaces 30c to the other of the side surfaces 30c. The ridges 426 can further be oriented straight along the direction of elongation or curved or bent as desired. The ridges 426 can be spaced from each other uniformly or variably along a direction perpendicular to the direction of elongation of the ridges 426. Thus, the ridges 426 can be spaced from each other along the longitudinal direction L. The direction of elongation can be determined by the orientation of the ridges when the ridges 426 are oriented straight. Alternatively, the direction of elongation can be determined by a straight line that extends from one of the terminal ends of the ridges to the respective opposite terminal end of the ridges, for instance, when the ridges 426 are curved.

Figure 7A:
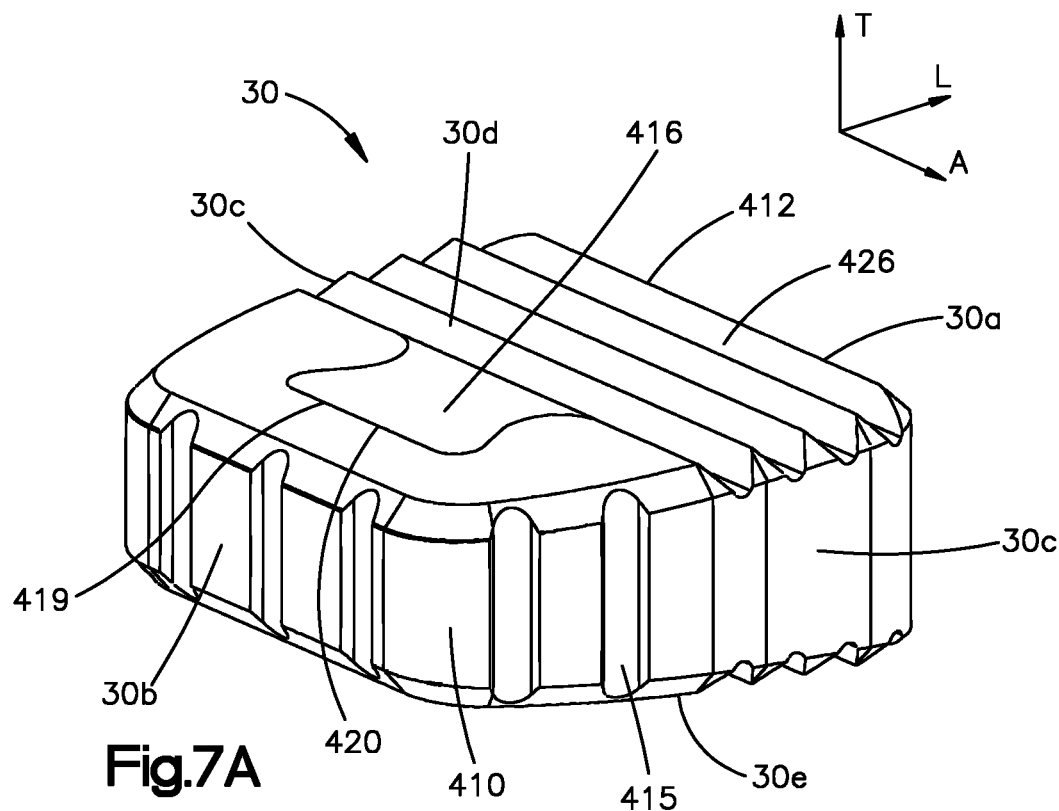
FIG. 7A is a perspective view of a spacer as illustrated in FIG. 6A, but including surface geometry in accordance with an alternative embodiment.

As illustrated in FIG. 6A, the ridges 426 can be disposed along an entirety of either or both of the top and bottom surfaces 30d and 30e along a direction perpendicular to the direction of elongation. For instance, the ridges 426 can be arranged from the proximal end surface 30a to distal end surface 30b. Alternatively, as illustrated in FIG. 7A, the ridges 426 can be disposed along a portion of either or both of the top and bottom surfaces 30d and 30e. For instance, the ridges 426 can be arranged along either or both of the top and bottom surfaces 30d and 30e of the spacer 30 at the cancellous spacer body 412, and not at the cortical body portion 410. In one example, the ridges 426 can be arranged along a portion of the cancellous spacer body 412, for instance, at a portion of the cancellous spacer body that does not include the engagement member 416. Alternatively, the ridges 426 can be arranged along an entirety of the cancellous spacer body 412. Alternatively or additionally, the ridges 426 can be arranged along a portion of the cortical spacer body 410.

Referring now to FIGS. 7B-7F, the surface geometry can alternatively or additionally include spikes 428. For instance, each of the spikes 428 can define a base 428a and extend out from the base 428a along the transverse direction T to a peak 428b. Thus, the spikes 428 at the top surface 30d can extend from the base 428a to the peak 428a in the upward direction, that is, away from the bottom surface 30e. Similarly, spikes 428 at the bottom surface 30e can extend from the base 428a to the peak 428a in the downward direction, that is, away from the top surface 30d. The spikes 428 can be tapered from the base 428a to the peak 428b. For instance the peak 428b can be a pointed peak or a rounded peak. The spikes 428 can be equidistantly spaced from each other along either or both of the lateral direction A and the longitudinal direction L. Alternatively or additionally, the spikes 428 can be spaced from each other variably along either or both of the both of the lateral direction A and the longitudinal direction L.

Figure 7B:
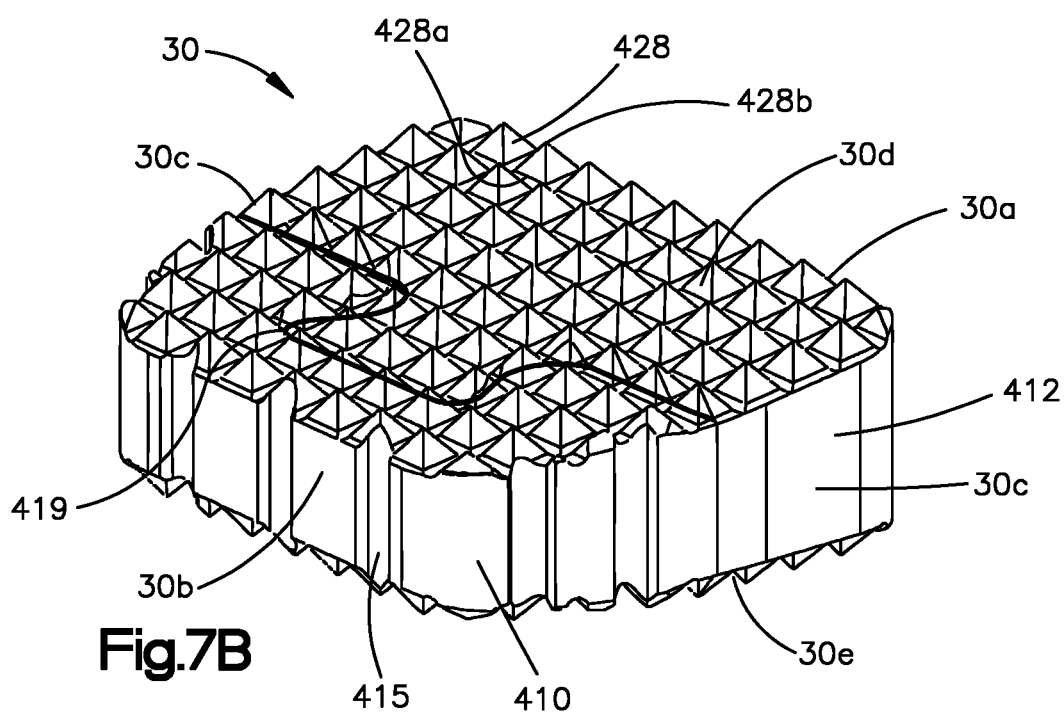
FIG. 7B is a perspective view of a spacer as illustrated in FIG. 7A, but including surface geometry in accordance with an another embodiment.
Figure 7C:
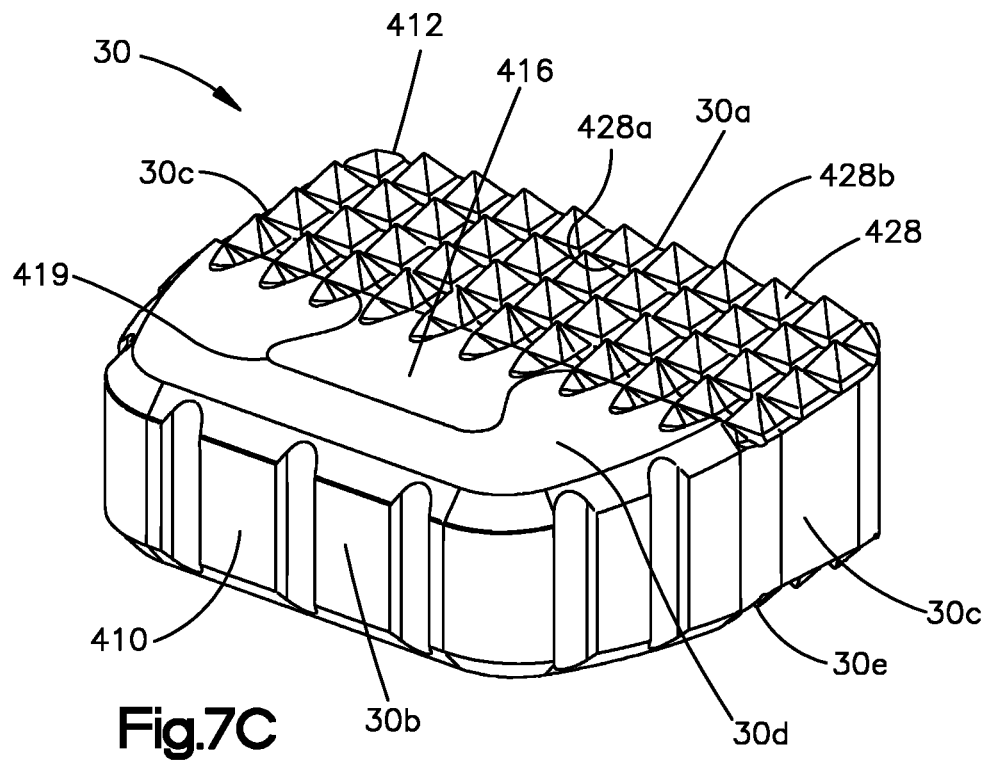
FIG. 7C is a perspective view of a spacer as illustrated in FIG. 6A, but including surface geometry in accordance with an another embodiment.
Figure 7D:
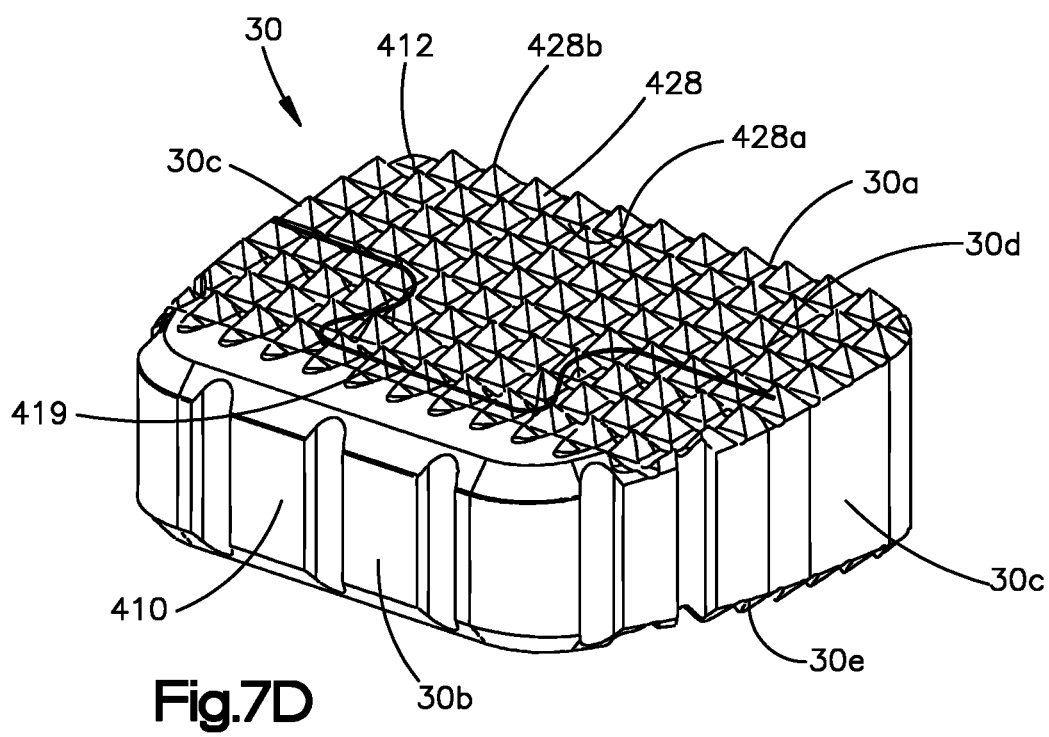
FIG. 7D is a perspective view of a spacer as illustrated in FIG. 7C, but including surface geometry in accordance with an another embodiment.

The spikes 428 can be arranged between the side surfaces 30c, and further between the proximal end surface 30a and the distal end surface 30b. For instance, as illustrated in FIG. 7B, the spikes 428 can be arranged from one of the side surfaces 30c to the other of the side surfaces 30c. Further, the spikes 428 can be arranged from the proximal end surface 30a to the distal end surface 30b. Thus, the spikes 428 can be defined by both of the cortical spacer body 410 and the cancellous spacer body 412. Alternatively, the spikes 428 can be defined by one of the cortical spacer body 410 and the cancellous spacer body 412. For example, as illustrated in FIG. 7C, the spikes 428 can be disposed along a portion of either or both of the top and bottom surfaces 30c and 30d. For instance, the spikes 428 can be arranged along either or both of the top and bottom surfaces 30d and 30e of the spacer 30 at the cancellous spacer body 412, and not at the cortical body portion 410. In one example, the spikes 428 can be arranged along a portion of the cancellous spacer body 412, for instance, at a portion of the cancellous spacer body that does not include the engagement member 416. Alternatively, the spikes 428 can be arranged along an entirety of the cancellous spacer body 412. Alternatively or additionally, the spikes 428 can be arranged along a portion of the cortical spacer body 410. As illustrated in FIG. 7D, the spikes 428 can be arranged along the top and bottom surfaces 30d and 30e of the entire cancellous spacer body 412, and a portion of the cortical spacer body 410. For example, the portion of the cortical spacer body 410 can be a proximal portion of the cortical spacer body that abuts the cancellous spacer body 412, including the engagement member 414. Alternatively, the portion of the cortical spacer body 410 can be a distal portion of the cortical spacer body 410 that is spaced from the cancellous spacer body 412.

Figure 7E:
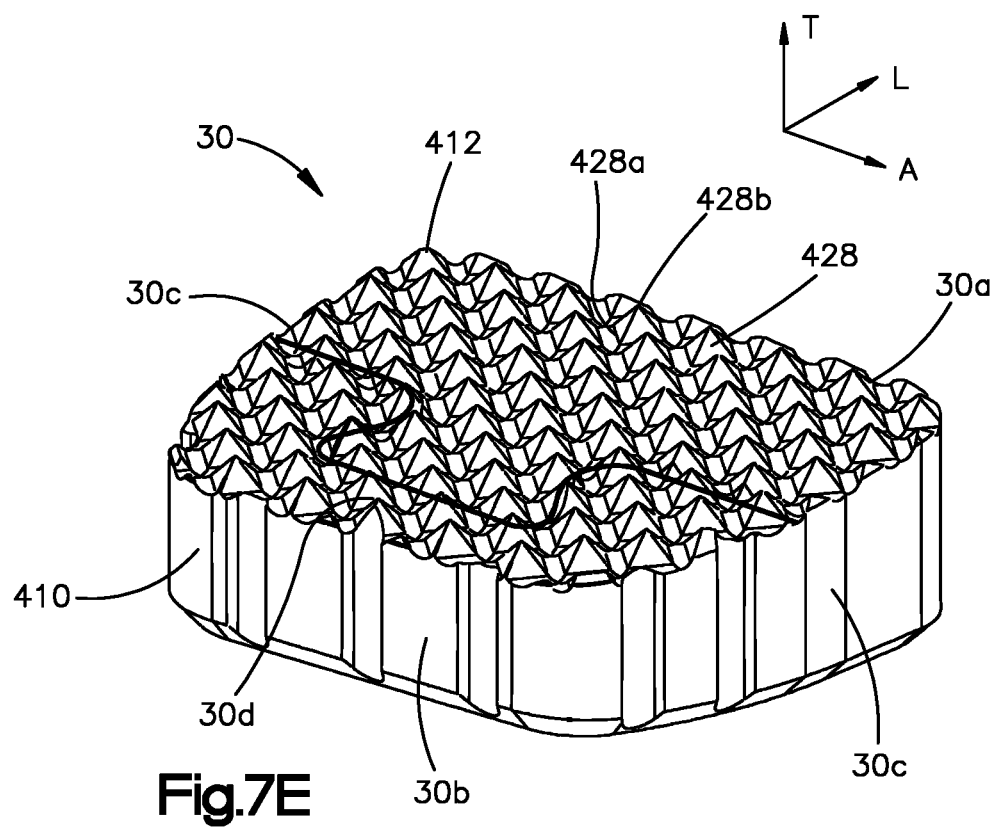
FIG. 7E is a perspective view of a spacer as illustrated in FIG. 7D, but including surface geometry in accordance with an another embodiment.

The spikes 428 can be pyramidal in shape or can assume any alternative shape as desired. In one example, the spikes 428 can define a plurality of surfaces, and edges at the interfaces between adjacent ones of the surfaces. As illustrated in FIG. 7B, the spikes 428 can be oriented surface-to-surface. That is, at least some up to all of the surfaces of at least some of the spikes 428 up to all of the spikes 428 face a respective surface of adjacent spikes 428 along either or both of the longitudinal direction L and the lateral direction A. Alternatively, as illustrated in FIG. 7E, the spikes 428 can be oriented edge-to-edge. That is, at least some up to all of the edges of at least some of the spikes 428 up to all of the spikes 428 face a respective edge of adjacent spikes 428 along either or both of the longitudinal direction L and the lateral direction A.

Figure 7F:
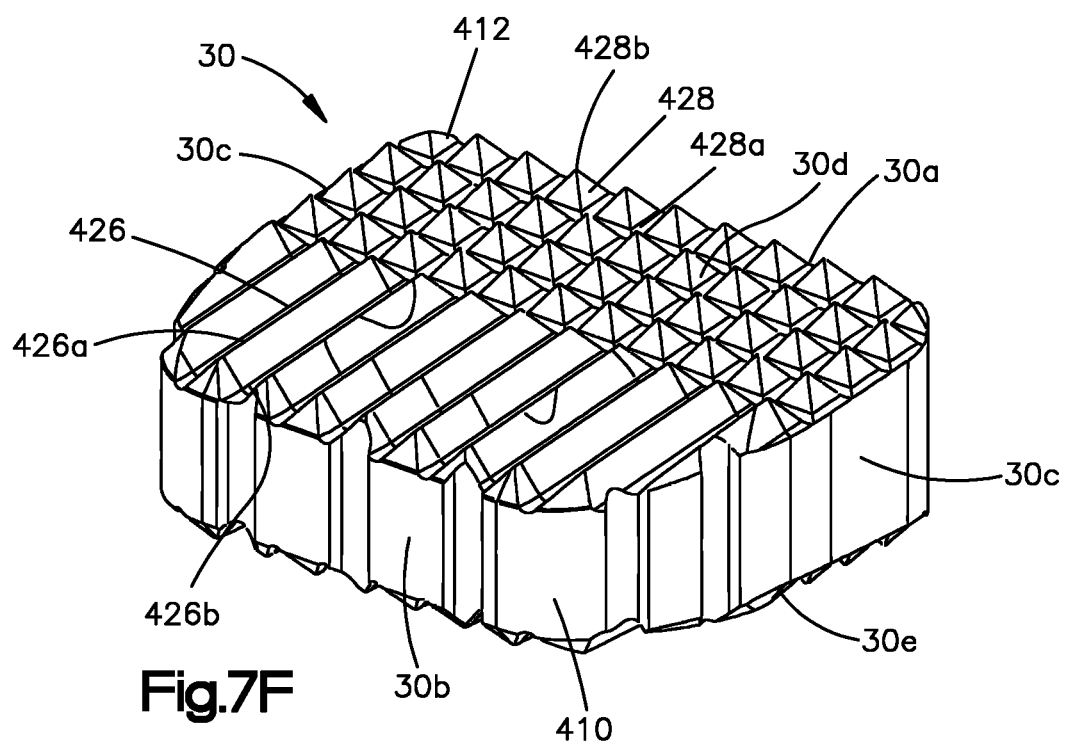
FIG. 7F is a perspective view of a spacer as illustrated in FIG. 7E, but including surface geometry in accordance with an another embodiment.

As illustrated in FIG. 7F, a first portion of the spacer 30 can include ridges 426, and a second portion of the spacer 30 different from the first portion can include spikes 428. The ridges 426 can be elongate along the longitudinal direction L. For instance, the first portion can be defined by the cortical spacer body 410, and the second portion can be defined by the cancellous spacer body 412. In one example, the first portion can include the cortical spacer body 410 and a portion of the cancellous spacer body 412. The portion of the cancellous spacer body 412 can include the engagement member 416. The second portion can include a portion of the cancellous spacer body 412 that does not include the engagement member 416. Alternatively, the second portion can include an entirety of the cancellous spacer body 412. Alternatively still, the second portion can be defined by the cortical spacer body 410, and the first portion can be defined by the cancellous spacer body 412. In one example, the second portion can include the cortical spacer body 410 and a portion of the cancellous spacer body 412. The portion of the cancellous spacer body 412 can include the engagement member 416. The first portion can include a portion of the cancellous spacer body 412 that does not include the engagement member 416. Alternatively, the first portion can include an entirety of the cancellous spacer body 412. It should be appreciated that while certain embodiments of the ridges 426 and the spikes 428 have been described the ridges 426 and the spikes 428 can be geometrically configured as desired, and arranged and oriented as desired. Further, it should be appreciated that while the surface geometry has been described with respect to ridges and spikes, the surface geometry can be shaped in accordance with any suitable alternative embodiment as desired.

Referring now to FIGS. 8A-11D generally, it is recognized that the spacer 30 can be constructed in accordance with any suitable alternative geometric configuration as desired. For instance, as illustrated in FIGS. 8A-8B, the first engagement member 414 of the cortical spacer body 410 can be configured as a projection, and the second engagement member 416 of the cancellous spacer body 412 can define a recess 419 that is sized and configured to receive the first engagement member 414. The first engagement member 414 can include a base 414a and at least one wing 414b such as a pair of wings 414b that extend from the stem 414a in the proximal direction, and project out with respect to the stem 414a in opposite directions away from each other along the lateral direction A. The second engagement member 416 can include a base 416a and a pair of necked portions 416b that extend out from the base 416a in the distal direction and project inward in opposite directions toward each other along the lateral direction A. The wings 414b can thus be disposed between the necked portions 416b and the base 416a. Similarly, the necked portions 416b can be disposed between the wings 414b and the base 414a. Accordingly, the first engagement member 414 is surrounded by the second engagement member 416 along the lateral direction A and in the proximal direction. Otherwise stated, the second engagement member 416 surrounds the first engagement member 414 along the lateral direction A and in the proximal direction.

Thus, as described above with respect to FIGS. 6A-6J, when the first and second engagement members 414 and 416 engage each other so as to join the cortical spacer body 410 to the cancellous spacer body 412, the engagement members 414 and 416 interfere with each other along both the longitudinal direction L and the lateral direction A. The interference thus prevents removal of the cortical spacer body 410 and the cancellous spacer body 412 along the longitudinal and lateral directions. Rather, in order to remove the cortical spacer body 410 and the cancellous spacer body 412 from each other, the cortical spacer body 410 and the cancellous spacer body 412 are moved with respect to each other along the transverse direction T until the engagement members 414 and 416 are removed from interference with each other.

It should be appreciated that the cortical spacer body 410 can include pair of sides 430 that are spaced from each other along the lateral direction A. The portions of the side surfaces 30c that are defined by the cortical spacer body 410 can be defined by respective different ones of the sides 430. Each of the sides 430 can further be spaced from the first engagement member 414 along the lateral direction A on opposite sides of the first engagement member 414. It can therefore be said the sides 430 flank opposed sides of the first engagement member 414 along the lateral direction A. Thus, the cortical spacer body 410 can define respective voids between the sides 430 and the first engagement member that receives the necked portions 416b of the cancellous spacer body 412. It can thus be said that the cortical spacer body 410 can partially surround the cancellous body portion 412. The sides 430 can terminate at a location aligned with the projection of the first engagement member 414 along the lateral direction A, as illustrated in FIG. 8A. Thus, the sides 430 can terminate at a location spaced in the distal direction from a lateral midline of the spacer 30 that divides the spacer into equal lengths along the longitudinal direction L. Further, the projection of the first engagement member 414 can terminate at a location spaced in the distal direction from a lateral midline of the spacer 30 that divides the spacer into equal lengths along the longitudinal direction L. Alternatively, as illustrated in FIG. 9A, the sides 430 can terminate at a location offset from the projection of the first engagement member 414 in the proximal direction. For instance, the sides 430 can terminate at a location spaced in the proximal direction from a lateral midline of the spacer 30 that divides the spacer into equal lengths along the longitudinal direction L. The sides 430 can further terminate at a location spaced from the proximal end surface 30a in the distal direction. As illustrated in FIGS. 8B and 9B, the spacer 30 can include the channel 418 and the force transfer member 424 as described above with respect to FIGS. 6A-M.

As illustrated in FIGS. 8A-8B, the cortical spacer body 410 can define a surface area at each of the top and bottom surfaces 30d and 30e as desired, for instance between 35 mm$^2$ and 60 mm$^2$, including between 40 mm$^2$ and 50 mm$^2$, for instance approximately 46 mm$^2$. The cancellous spacer body 412 can define a surface area at each of the top and bottom surfaces 30d and 30e as desired, for instance between 50 mm$^2$ and 100 mm$^2$, including between 70 mm$^2$ and 90 mm$^2$, for instance approximately 81 mm$^2$. As illustrated in FIGS. 9A-9B, the cortical spacer body 410 can define a surface area at each of the top and bottom surfaces 30d and 30e as desired, for instance between 50 mm$^2$ and 80 mm$^2$, including between 60 mm$^2$ and 70 mm$^2$, for instance approximately 62 mm$^2$. The cancellous spacer body 412 can define a surface area at each of the top and bottom surfaces 30d and 30e as desired, for instance between 90 mm$^2$ and 120 mm$^2$, including between 100 mm$^2$ and 110 mm$^2$, for instance approximately 104 mm$^2$.

Referring now to FIGS. 10A-10B, the first engagement member 414 can define a recess 419, and the second engagement member 416 be configured as a projection 420 that is sized to be received in the recess 419. Otherwise sated, the recess 419 is sized to receive the projection 420. Thus, the recess 419 defined by the first engagement member 414 is sized to receive the second engagement member 416. The first engagement member 414 can include a base 414a and a pair of necked portions 414b that extend out from the base 414a in the distal direction and project inward in opposite directions toward each other along the lateral direction A. The base 414a and the necked portions 414b can define the recess 419. The recess 419 can extend through the cortical spacer body 410 along the transverse direction T. The second engagement member 416 can include a base 416a and at least one wing 416b, such as a pair of wings 416b, that extends from the stem 416a in the proximal direction, and project out with respect to the stem 416a in opposite directions away from each other along the lateral direction A. The wings 416b can thus be disposed between the necked portions 414b and the base 414a. Similarly, the necked portions 414b can be disposed between the wings 416b and the base 416a. Accordingly, the second engagement member 416 is surrounded by the first engagement member 414 along the lateral direction A and in the distal direction. Otherwise stated, the first engagement member 414 surrounds the second engagement member 416 along the lateral direction A and in the distal direction.

It should be appreciated that the cortical spacer body 410 can include pair of sides 430 that are spaced from each other along the lateral direction A. The portions of the side surfaces 30c that are defined by the cortical spacer body 410 can be defined by respective different ones of the sides 430. Each of the sides 430 extend in the proximal direction from the necked portions on opposite lateral sides of the cortical spacer body 410. Thus, the cortical spacer body 410 can define a void 434 between the sides 430 in the lateral direction that receives the base 416a, such that the wings are inserted into the recess 419. The void 434 can thus define a lead-in, and can be open, to the recess 419 along the distal direction. It can thus be said that the cortical spacer body 410 can partially surround the cancellous body portion 412. The sides 430 can terminate at a location spaced in the proximal direction from a lateral midline of the spacer 30 that divides the spacer into equal lengths along the longitudinal direction L. The sides 430 can further terminate at a location spaced from the proximal end surface 30a in the distal direction. Alternatively, the sides 430 can terminate at a location offset from the projection of the first engagement member 414 in the distal direction. For instance, the sides 430 can terminate at a location spaced in the proximal direction from a lateral midline of the spacer 30 that divides the spacer into equal lengths along the longitudinal direction L. As illustrated in FIGS. 8B and 9B, the spacer 30 can include the channel 418 and the force transfer member 424 as described above with respect to FIGS. 6A-M.

Thus, when the first and second engagement members 414 and 416 engage each other so as to join the cortical spacer body 410 to the cancellous spacer body 412, the engagement members 414 and 416 interfere with each other along both the longitudinal direction L and the lateral direction A. The interference thus prevents removal of the cortical spacer body 410 and the cancellous spacer body 412 along the longitudinal and lateral directions. Rather, in order to remove the cortical spacer body 410 and the cancellous spacer body 412 from each other, the cortical spacer body 410 and the cancellous spacer body 412 are moved with respect to each other along the transverse direction T until the engagement members 414 and 416 are removed from interference with each other. As illustrated in FIG. 10B, the spacer 30 can include the channel 418 and the force transfer member 424 as described above with respect to FIGS. 6A-M.

As illustrated in FIGS. 10A-10B, the cortical spacer body 410 can define a surface area at each of the top and bottom surfaces 30d and 30e as desired, for instance between 50 mm$^2$ and 80 mm$^2$, including between 60 mm$^2$ and 70 mm$^2$, for instance approximately 62 mm$^2$. The cancellous spacer body 412 can define a surface area at each of the top and bottom surfaces 30d and 30e as desired, for instance between 90 mm$^2$ and 120 mm$^2$, including between 100 mm$^2$ and 110 mm$^2$, for instance approximately 104 mm$^2$.

Figure 11A:
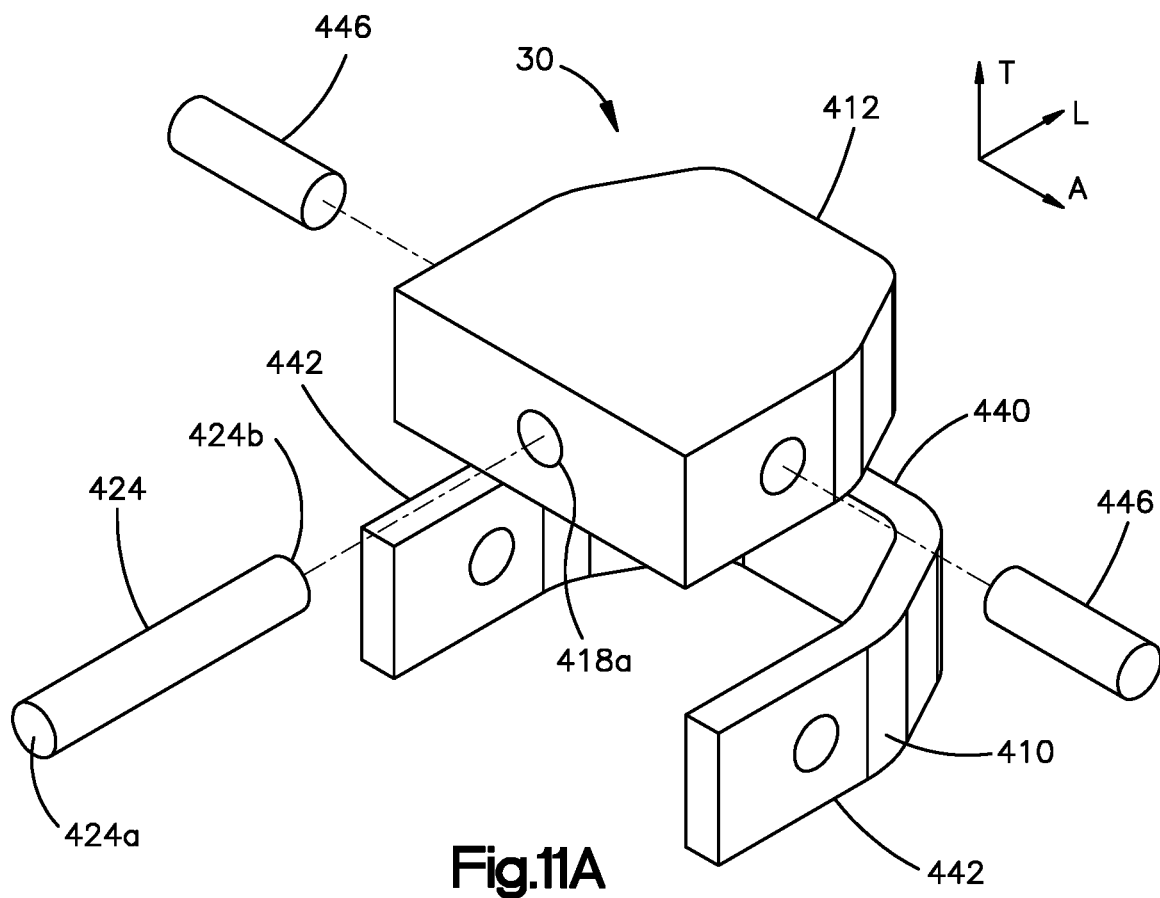
FIG. 11A is an exploded perspective view of a spacer similar to the spacer illustrated in FIG. 6A, but constructed in accordance with an alternative embodiment.
Figure 11B:
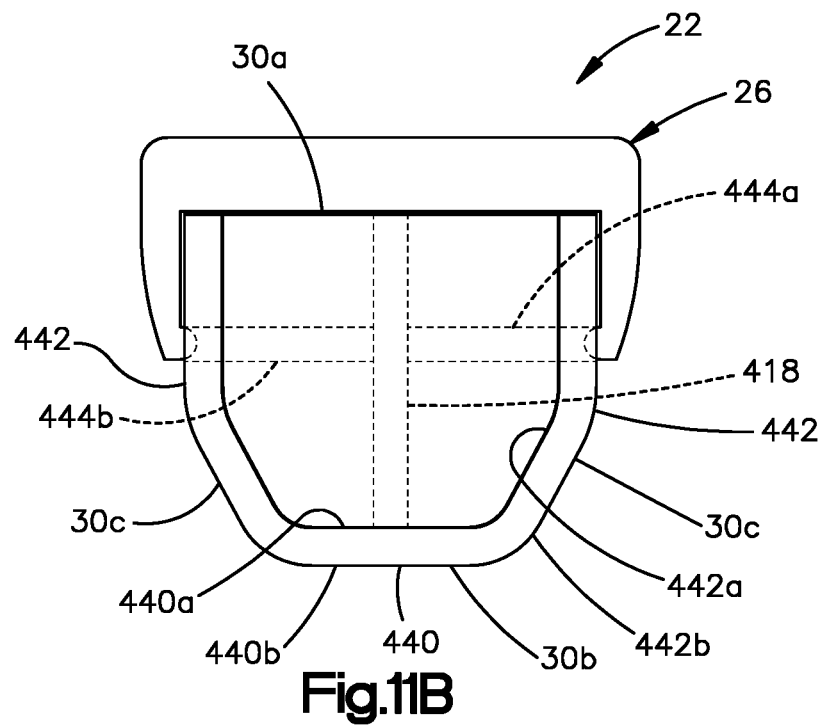
FIG. 11B is a top plan view of an intervertebral implant including a frame attached to the spacer illustrated in FIG. 11A.

Referring now to FIG. 11A-11B, the distal end surface 30b can be defined by the cortical spacer body 410, and the proximal end surface 30a is defined by the cancellous spacer body 412. For instance, the cortical spacer body 410 can define a cross member 440 that defines the distal end surface 30b. The cross member 440 defines an inner surface 440a and an outer surface 440b opposite the inner surface 440a. The inner surface 440a is configured to abut a distal end surface of the cancellous spacer body 412, and the outer surface 440b is configured to face the frame 26 when the frame 26 is attached to the spacer 30. The cross member 440 further defines opposed ends that are opposite each other along the lateral direction A, and first and second arms 442 that extend along the proximal direction from respective different ones of the opposed ends. The arms 442 can thus define sides 430 of the cortical spacer body 410 that are spaced from each other along the lateral direction A. Each of the arms 442 defines a respective inner surface 442a and an outer surface 442b opposite the inner surface 442a. The inner surfaces 442a are configured to abut opposed side surfaces of the cancellous spacer body 412 that are spaced from each other along the lateral direction A. The arms 442 can extend along an entirety of the length of the side surfaces 30c, and can terminate at a location substantially flush with the proximal end surface 30a. Accordingly, the cortical spacer body 410 can partially surround the cancellous spacer body 412. In particular, the cortical spacer body 410 can surround all sides of the cancellous spacer body, with the exception of the proximal end surface 30a, along a plane that is defined by the longitudinal direction L and the lateral direction A. Alternatively, the cortical spacer body 410 can further extend along the proximal end 30a, such that the cortical spacer body 410 entirely surrounds the cancellous body portion 412 along the plane that is defined by the longitudinal direction L and the lateral direction A. Thus, it can be said that the cortical spacer body 410 at least partially surrounds the cancellous body portion 412.

The spacer 30 further defines the channel 418 that extends through the cancellous spacer body 412. The channel 418 can terminate at the cortical spacer body 410. Alternatively, the channel 418 can extend at least into the cortical spacer body 410. For instance, the channel 418 can terminate in the cortical spacer body 410. Alternatively, the channel 418 can extend through the cortical spacer body 410. The channel 418 can have a first opening 418a defined by the proximal end surface 30a. Accordingly, the channel 418 can have a first end defined by the first opening 418a. The first opening 418a can be an enclosed opening. That is, the first opening 418a can be enclosed by the proximal end surface 30a along a plane defined by the lateral direction A and the transverse direction T. The first opening 418a can be sized to receive the abutment member 73 of the frame 26 when the frame 26 is attached to the spacer 30. Thus, the abutment member 73 can extend from the first opening 418a into the channel 418 in the distal direction.

The channel 418 has a second end opposite the first end. The second end of the channel 418 can be terminate within the cortical spacer body 410, such that the first opening 418a is the only opening of the aperture. Alternatively, the second end of the channel 418 can terminate at the cortical spacer body 410, such that the second end 418b is defined by the cancellous spacer body 412. Alternatively still, the channel 418 can extend through the cortical spacer body 410. Further, the spacer 30 further includes the force transfer member 424 that is configured to be inserted into the channel 418 as described above. Thus, the channel 418 is sized and configured to receive the force transfer member 424. When the force transfer member 424 is disposed in the channel 418, the first end 424a can be positioned adjacent the first opening 418a. In one example, the first end 424a can be recessed with respect to the first opening 418a along the distal direction. In another example, the first end 424a can be flush with the proximal end surface 30a. Thus, the first end 424a can define a surface geometry that matches the surface geometry of the proximal end surface 30. As described above, the abutment member 73 can contact the first end 424a when the frame 26 is attached to the spacer 30, and the force transfer member 424 is disposed in the channel 418. For instance, the first opening 418a can be sized to receive the abutment member 73 of the frame 26 when the frame 26 is attached to the spacer 30. Thus, the abutment member 73 can extend from the first opening 418a into the channel 418 and abut the first end 424a of the force transfer member 424, for instance along the longitudinal direction L.

Further, when the force transfer member 424 is disposed in the channel 418, the second end 424b can be in contact with the cortical spacer body 410. For instance, the second end 424b can abut the cortical spacer body 410 along the longitudinal direction L. Alternatively, the second end 424b can be embedded in the cortical spacer body 410. Alternatively still, the second end 424b can be flush with the distal end surface 30b. Thus, the second end 424b can be in abutment contact with the cortical spacer body 410 along the longitudinal direction L. Alternatively or additionally, the second end 424b can be in press fit contact with the cortical spacer body 410.

During operation, as the intervertebral implant 22 is inserted into the intervertebral space, the outer surface 54 of the body 46 of the support member 34 may be impacted by an impaction tool or the like in order to advance the implant 22 into the intervertebral space. Because the abutment member 73 is in contact with the force transfer member 424, for instance in abutment contact or in press-fit contact, or both, impaction forces is transferred from the frame 26, to the force transfer member 424, through the force transfer member 424, and to the cortical spacer body 410. Thus, though the support member 34 is positioned adjacent to the cancellous spacer body 412, a substantial majority up to a substantial entirety of the impaction forces are absorbed by the cortical spacer body 412, which has a rigidity greater than that of the cancellous spacer body 412.

As described above, the spacer body 30 defines a pair of side surfaces 30c. As illustrated in FIG. 11A, the spacer 30 can include an attachment channel 444 that can extend through the cortical spacer body 410 and into the cancellous spacer body 412 along a direction that is angularly offset with respect to the force transfer channel 418. In accordance with one embodiment, the attachment channel 444 include a first segment 444a that extends from a first one of the side surfaces 30c toward the second one of the side surfaces 30c, and terminates prior to intersecting the force transfer channel 418. The attachment channel 444 can include a second segment 444b that extends from the second one of the side surfaces 30c toward the first one of the side surfaces 30c, and terminates prior to intersecting the force transfer channel 418. The first and second segments 444a and 444b can be joined so as to intersect the force transfer channel 418. The spacer 30 can further include at least one coupling member 446 that is sized to be inserted into the attachment channel 444. Thus, the at least one coupling member 446 extends through one of the respective arms 442 and into the cancellous spacer body 412 in the attachment channel 444. In one example, the spacer 30 includes a first coupling member 446 that extends into the first segment 444a through a first respective one of the arms 442 and into the cancellous spacer body 412. The spacer 30 can further include a second coupling member 446 that extends into the second segment 444b through a second respective one of the arms 442 and into the cancellous spacer body 412. The coupling members 446 are elongate along a length that is less than the distance from the respective side surface 30c and the force transfer channel 418. Accordingly, the coupling members 446 attach the cortical spacer body 410 to the cancellous spacer body 412. Further the coupling members 446 avoid mechanical interference with the force transfer member 424 do not interfere with each other.

The spacer body 30 can further include the frame 26 having the support member 34 and the first and second arms 38 and 42 that extend out from the support member in the proximal direction as described above. The support member 34 is configured to abut the proximal end surface 30a, and the arms 38 and 42 are configured to abut and extend along respective different ones of the side surfaces 30c. The arms 38 and 42 can extend along the respective ones of the side surfaces 30c past the cortical spacer body 410 and can terminate at the cancellous spacer body 412. The retention members 116 of the frame 26 that extend in from each of the arms 38 and 42 can extend into respective side surfaces 30c in the manner as described above with respect to FIGS. 2C-2F. For instance, the at least one retention member 116 that extends from the first arm 38 can extend into the first segment 444a. The at least one retention member 116 that extends from the second arm 42 can extend into the second segment 444a. Alternatively, the arms 38 and 42 can extend along an entirety of the length of the side surfaces 30c from the proximal end surface 30a to the distal end surface 30b, and can terminate at a location substantially flush with the proximal end surface 30a.

Figure 11C:
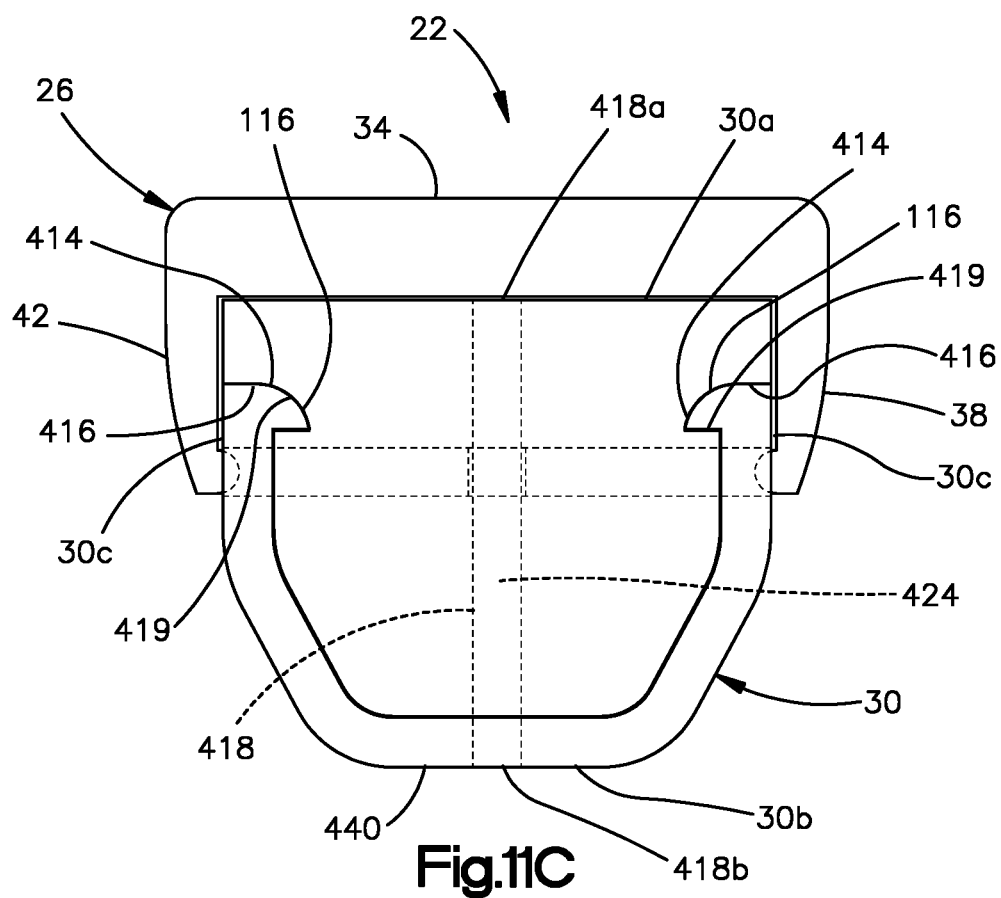
FIG. 11C is a to plan view of an intervertebral implant including a frame attached to a spacer constructed in accordance with an alternative embodiment.
Figure 11D:
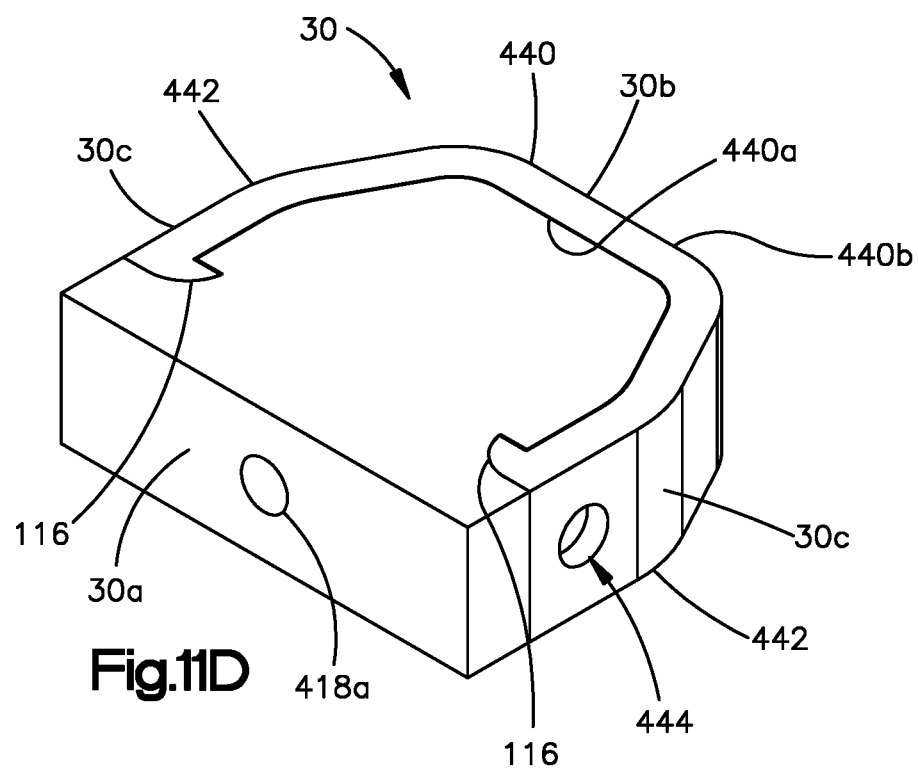
FIG. 11D is a perspective view of the spacer illustrated in FIG. 11C.

As described above with respect to FIGS. 11A-B, the arms 442 can extend along an entirety of the length of the side surfaces 30c, and can terminate at a location substantially flush with the proximal end surface 30a. Alternatively, as illustrated in FIGS. 11C-D, the arms 442 can extend along a portion of the length of the side surfaces 30c, and can terminate at a location spaced from the proximal end surface 30a. Thus, the cortical spacer body 410 can at least partially surround the cancellous spacer body 412. The cortical spacer body 410 can include respective engagement members 414 in the form of the retention members 116 that project inward from each of the arms 442 toward the other one of the arms. The cancellous spacer body 412 can include respective engagement members 416 configured as recesses 419 that are sized and configured to receive the engagement members 414 so as to couple the cortical spacer body 410 to the cancellous spacer body 412. As illustrated in FIGS. 11C-D, and FIGS. 6A-10B, the cortical spacer body 410 can be flush with the cancellous spacer body 412 at the respective side surfaces 30C. As illustrated in FIG. 11D, the frame 26 can be attached to the spacer 30 as described above with respect to FIG. 11B. While the cortical spacer body 410 can partially surround the cancellous spacer body 412 as described herein, it should be appreciated that the cortical spacer body 410 can entirely surround the cancellous spacer body 412 as desired. Thus, it can be said that the cortical spacer body 410 can at least partially surround the cancellous spacer body 412.

Referring now to FIGS. 12A-12D, the spacer 30 can be constructed in accordance with an alternative embodiment. As described above, the spacer can define a proximal end surface 30a and a distal end surface 30b that is spaced from the proximal end surface 30a along the longitudinal direction L. For instance, the distal end surface 30b is spaced from the proximal end surface 30a in the distal direction. Thus, the distal end surface 30b can be spaced from the proximal end 30a in the insertion direction of the spacer 30 into the intervertebral space. Accordingly, the distal end surface 30b is spaced from the proximal end 30a in the insertion direction of the intervertebral implant 22 into the intervertebral space. It should be appreciated that, when the implant 22, and thus the spacer 30, is implanted in the intervertebral space, the distal end surface 30b can be spaced posteriorly from the proximal end surface 30a. Alternatively, as described above, the spacer 30, and thus the intervertebral implant 22, can be inserted in the intervertebral space along an insertion direction that is in the lateral direction or the oblique direction.

The spacer 30 further defines a pair of opposed side surfaces 30c spaced from each other along the lateral direction A. Each of the side surfaces 30c further extends from the proximal end surface 30a to the distal end surface 30b. When the frame 26 is attached to the spacer 30 (see FIGS. 2A-B), the support member 34 can extend along the proximal end surface 30a, and the arms 38 and 42 can extend along at least a portion up to an entirety of the length along the longitudinal direction L of respective different ones of the sides 30c. It should be appreciated that the surfaces 30a-30e can be sized and shaped as desired. For instance at least one or more up to all of the surfaces 30a-30e can be planar, curved, bent, or otherwise non-planar as desired.

The spacer 30 further defines a top surface 30d and a bottom surface 30e spaced from the top surface 30d along the transverse direction T. For instance, the top surface 30d is spaced upward with respect to the bottom surface 30e. Thus, the top surface 30d is configured to face the superior vertebral surface 14a of the superior vertebral body 10a, and contact the superior vertebral surface 14a of the superior vertebral body 10a. The bottom surface 30e is configured to face the inferior vertebral surface 14b of the inferior vertebral body 10b, and contact the inferior vertebral surface 14b of the inferior vertebral body 10b. The spacer 30 can define a height from the top surface 30c to the bottom surface 30d in the transverse direction T. The spacer can further define a length from the proximal end surface 30a to the distal end surface 30b in the longitudinal direction. The distal end surface 30b can define a first width along the lateral direction A that is less than a second width along the lateral direction A of the proximal end surface 30a. Each of the first and second widths can extend along the lateral direction A from one of the side surfaces 30c to the other of the side surfaces 30c. At least one or both of the first and second widths can be greater than the height and less than the length.

As described above, the spacer 30 can be made from a bone graft material such as allograft bone, autograft bone, or xenograft bone, for example. For instance, the spacer 30 can include a cortical spacer body 410 and a cancellous spacer body 412. The cortical spacer body 410 can define at least a portion up to an entirety of the distal end surface 30b. The cancellous spacer body 412 can define at least a portion of the proximal end surface up to an entirety of the proximal end surface 30a. It will be appreciated, as described above, that at least one, such as each, of the fixation members, which can be configured as screws, that is inserted through the fixation element receiving aperture 58 (see FIGS. 3A-3C) toward the spacer 30 travels from the support member 34 and through the cancellous spacer body 412, and thus through the cancellous bone graft material, without passing through cortical spacer body 410, and thus without passing through any of the cortical bone graft material. Thus, a straight line passing centrally through the fixation element receiving apertures 58 is aligned with the cancellous spacer body 412 without first passing through the cortical spacer body 410.

Figure 12A:
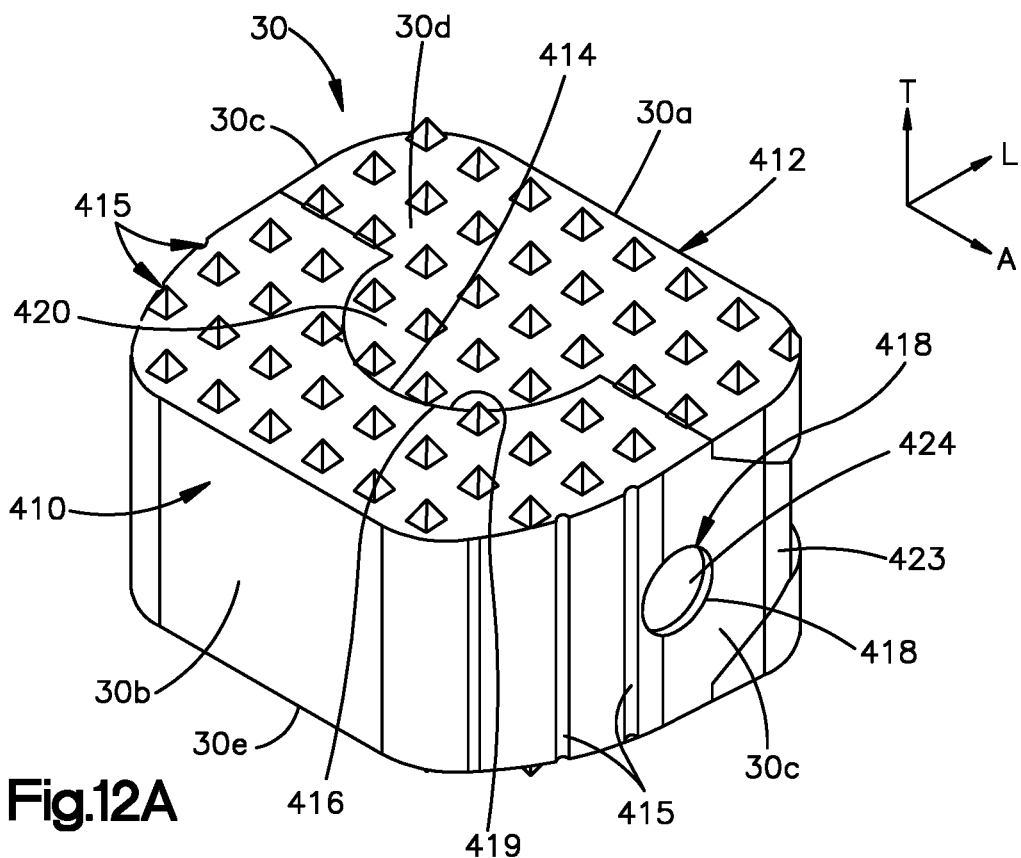
FIG. 12A is a perspective view of an intervertebral spacer constructed in accordance with an alternative embodiment, including grooves configured to engage the intervertebral implant frame illustrated in FIG. 3A.
Figure 12B:
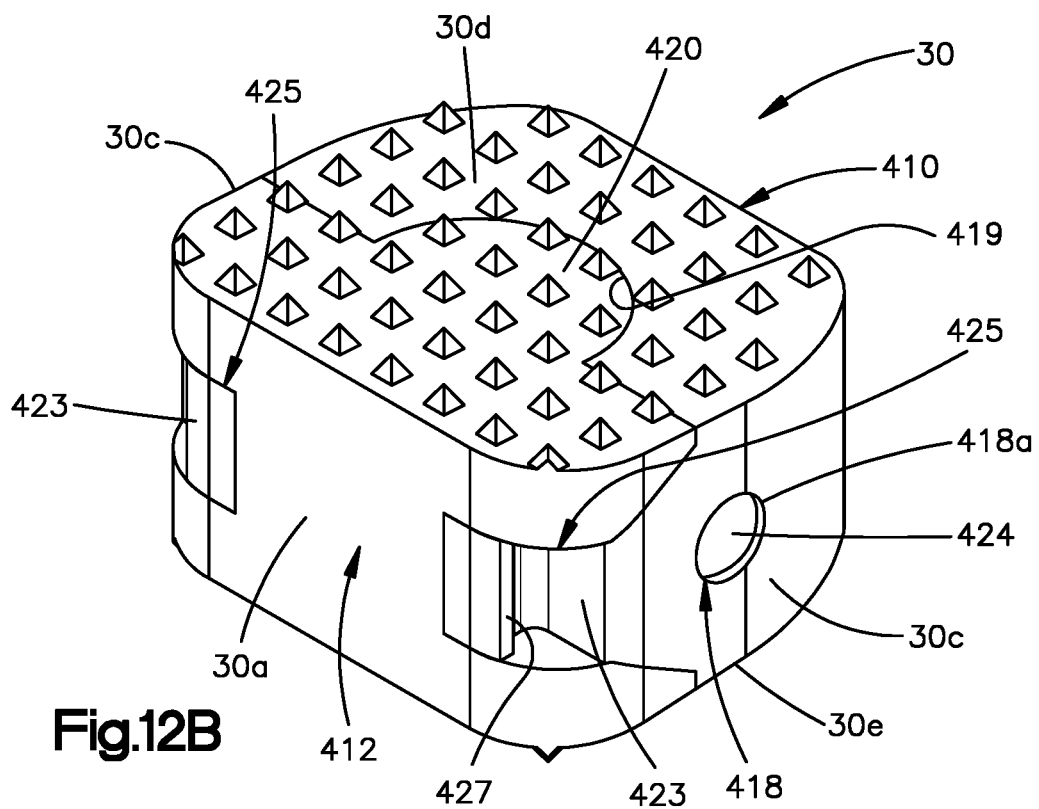
FIG. 12B is another perspective view of the intervertebral spacer as illustrated in FIG. 12A, but including smooth opposed lateral surfaces so as to engage an intervertebral implant frame in accordance with an alternative embodiment.
Figure 12E:
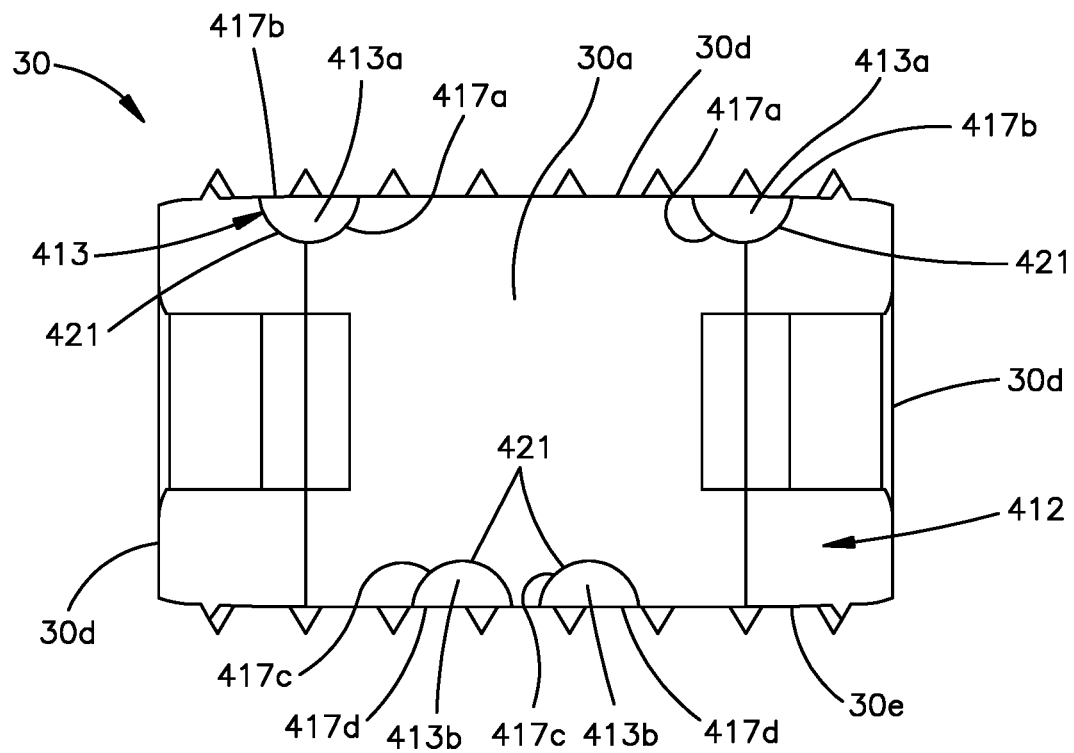
FIG. 12E is a schematic front elevation view of the intervertebral spacer of FIGS. 12A and 12B, showing apertures created by fixation elements that extend through the frame and into the corresponding vertebral body.

For instance, as illustrated in FIG. 12E, each of the fixation members can extend through the cancellous spacer body 412 so as to define a respective bone fixation channel 413 that extends through the cancellous spacer body 412. The bone fixation channel 413 can have a perimeter 421 that is defined by the cancellous spacer body 412. The perimeter 421 defined by the cancellous spacer body 412 can be arc-shaped. The channels 413 can include at least one first channel 413a, such as a pair of first channels 413a. The at least one first channel 413a can define a front opening 417a in the proximal end surface 30a, and a top opening 417b in the top surface 30d. The front opening 417a can be open at an intersection of the proximal end surface 30a and the top surface 30d. Accordingly, a length of the at least one first bone fixation channel 413a can be defined at a location distal of the front opening 417a. Further, the length of the at least one first bone fixation channel 413a can be open along both 1) in a superior direction that extends from the bottom surface 30e to the top surface 30d, and 2) a proximal direction that is opposite the distal direction at a location distal of the front opening 417a in the proximal end surface 30a.

Similarly, the channels 413 can include at least one second channel 413b, such as a pair of second channels 413b. The at least one second channel 413b can define a front opening 417c in the proximal end surface 30a, and a bottom opening 417d in the bottom surface 30e. The at least one second channel 413b can be open at an intersection of the proximal end surface 30a and the bottom surface 30e. Accordingly, a length of the at least one second bone fixation channel 413b can be defined at a location distal of the front opening 417c. Further the length of the at least one second bone fixation channel 413b can be open along both 1) in an inferior direction that extends from the top surface 30d to the bottom surface 30e, and 2) the proximal direction at a location distal of the front opening 417c in the proximal end surface 30a.

Figure 12F:
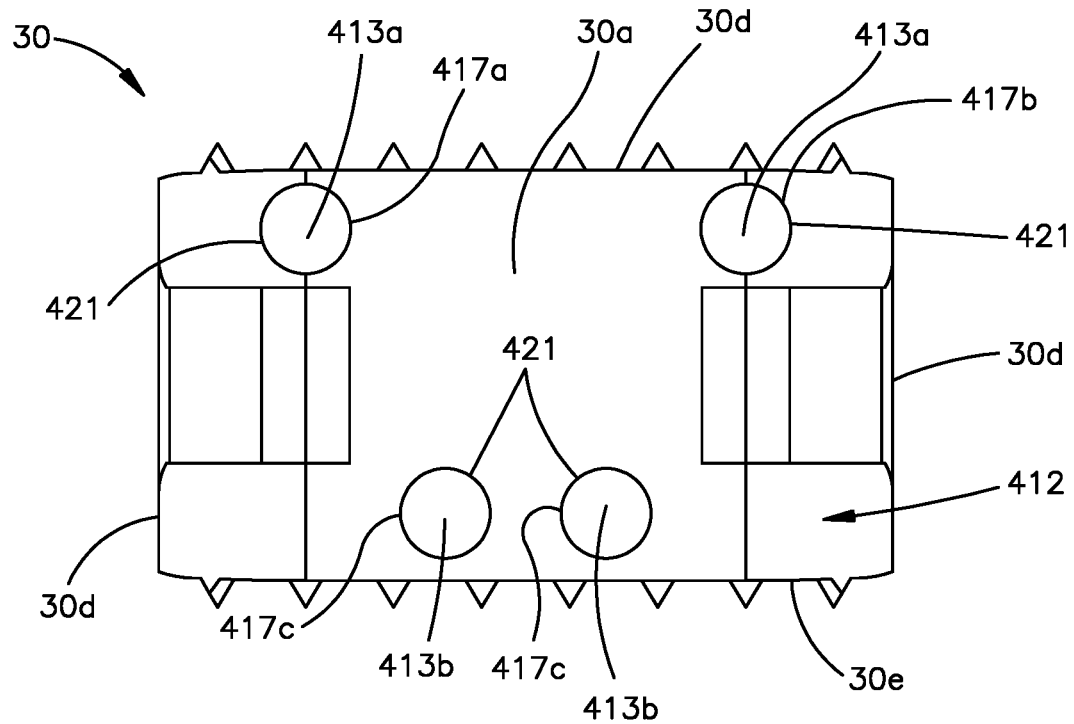
FIG. 12F is a schematic front elevation view showing apertures created by fixation elements that extend through the frame and into the corresponding vertebral body, the apertures configured in accordance with an alternative embodiment.

Alternatively, as illustrated in FIG. 12F, the front opening 417a of the at least one first channel 413a can be fully encircled by the cancellous spacer body 412 at the proximal end surface 30a. Thus, an entirety of the front opening 417a can be spaced from the top surface 30d along the inferior direction. Similarly, the top opening can be fully encircled by the cancellous spacer body 412 at the top surface 30d. Thus, the top opening can be spaced from the proximal end surface 30a along the distal direction. It should therefore be appreciated that the at least one first channel 413a can be fully encircled by the cancellous spacer body 412 along an entirety of its length from the front opening 413a to the top opening. Furthermore, the front opening 417c of the at least one second channel 413b can be fully encircled by the cancellous spacer body 412 at the proximal end surface 30a. Thus, an entirety of the front opening 417c can be spaced from the bottom surface 30e along the superior direction. Similarly, the bottom opening can be fully encircled by the cancellous spacer body 412 at the top surface 30d. Thus, the bottom opening can be spaced from the proximal end surface 30a along the distal direction. It should therefore be appreciated that the at least one second channel 413b can be fully encircled by the cancellous spacer body 412 along an entirety of its length from the front opening 413c to the bottom opening.

Referring again to FIGS. 12A-12D, the cortical spacer body 410 can further define a first portion of one or both of the side surfaces 30c, and the cancellous spacer body 412 can define a second portion of one or both of the side surfaces 30c. At least some of the first portion of the side surfaces 30c can be distal with respect to the second portion of the side surfaces 30c. For instance, the cortical spacer body 410 can define laterally opposed arms 423 that extend proximally along the opposed sides 30c, respectively, to the proximal end surface 30a. Thus, respective ends of the opposed arms 423 can be flush with the cancellous spacer body 412 at the proximal end surface 30a. The cancellous spacer body 412 can define laterally opposed recesses 425 that extend through the proximal end surface 30a and are sized to receive the opposed arms 423, respectively. Accordingly, the cortical spacer body 412 at the proximal end surface 30a can abut the support member of the frame. Thus, impaction forces in the insertion direction against the support member of the frame 26 that urge the implant to be inserted into the intervertebral space can be transferred from the frame 26 to the cortical spacer body 410 at the arms 423. Further, the arms 423 can define engagement members 427 that are configured to receive an insertion instrument that inserts the spacer 30 into the intervertebral space without the frame 26. Further, the cortical spacer body 410 can further define a first portion of either or both of the top and bottom surfaces 30*d* and 30*e*. The cancellous spacer body 412 can define a second portion of either or both of the top and bottom surfaces 30*d* and 30*e*. The first portion of the top and bottom surfaces 30*d* and 30*e* can be distal with respect to the second portion of the top and bottom surfaces 30*d* and 30*e*.

The cortical spacer body 410 and the cancellous spacer body 412 are configured to abut each other so as to define the spacer 30. For instance, the cortical spacer body 410 can include an engagement member 414, and the cancellous spacer body 412 can include an engagement member 416 that is configured to engage with the engagement member 414 of the cortical spacer body 410 so as to join the cortical spacer body 410 to the cancellous spacer body 412. In this regard, the engagement member 414 of the cortical spacer body 410 can be referred to as a first engagement member, and the engagement member 416 of the cancellous spacer body 412 can be referred to as a second engagement member. The first engagement member 414 can be disposed distal with respect to the second engagement member 416. Further, the first and second engagement members 414 and 416 can overlap along the longitudinal direction L such that a straight line that extends in the distal direction from the proximal end surface 30*a* can pass through both the first engagement member 414 and the second engagement member 416.

In accordance with one embodiment, the first engagement member 414 can define a recess 419, and the second engagement member 416 be configured as a projection 420 that is sized to be received in the recess 419. Otherwise sated, the recess 419 is sized to receive the projection 420. Thus, the recess 419 defined by the first engagement member 414 is sized to receive the second engagement member 416. The recess 419 can extend through the cortical spacer body 410 along the transverse direction T. Accordingly, the second engagement member 416 is surrounded by the first engagement member 414 along the lateral direction A and in the distal direction. Otherwise stated, the first engagement member 414 surrounds the second engagement member 416 along the lateral direction A and in the distal direction. It can thus be said that the cortical spacer body 410 can partially surround the cancellous body portion 412. Alternatively, the first engagement member 414 can be configured as a projection, and the second engagement member can be configured as a recess that receives the projection.

The spacer 30 further defines a force transfer channel 418 that extends through the cancellous spacer body 412 and the cortical spacer body 410 along the lateral direction A. Thus, the first opening 418*a* of the channel 418 can be defined by one of the side surfaces 30*c*, and the second opening 418*b* of the channel 418 can be defined by the other of the side surfaces 30*c*. In one embodiment, one or both of the first and second openings 418*a* and 418*b* can be defined by the cortical spacer body 410. In another embodiment, one or both of the first and second openings 418*a* and 418*b* can be defined by the cancellous spacer body 412. The first and second openings 418*a* can be defined by enclosed perimeters. A first portion of the channel 418 can further be defined by cancellous spacer body 410. For instance, the first portion of the channel 418 can extend from each of the respective sides 30*c* to the recess 419. A second portion the channel 418 can be defined by the cancellous spacer body 412. For instance, the second portion can be defined by the projection 420.

As illustrated in FIG. 12A, the spacer 30 can define a plurality of grooves 415 that can extend into the side surfaces 30*c* at the cortical spacer body 410, and the distal end surface 30*b*. The grooves 415 can extend at least into the spacer 30 along the transverse direction T, and can extend through the spacer 30 along the transverse direction T. The retention members 116 supported by the first arm 38 (see, e.g., FIG. 3A) are configured to be inserted into the grooves 415 at a first one of the side surfaces 30*c*. The retention members 116 supported by the second arm 42 are configured to be inserted into the grooves 415 at the second one of the side surfaces 30*c*. Alternatively, the spacer can be devoid of the grooves 415, such that the retention members 116 bite into the side surface 30*c* so as to create respective recesses that retain the retention members in the cortical spacer body 410. Alternatively, the first and second arms 38 and 42 can extend around the side surfaces and terminate at the distal end surface 30*b*. Thus, as described above, it should be appreciated that the frame is configured to secure the cancellous spacer body 412 at a location between the support member 34 of the frame 26 and the cortical spacer body 410.

With continuing reference to FIGS. 12A-12D, the spacer 30 further includes a force transfer member 424 that is configured to be inserted into the channel 418. Thus, the channel 418 is sized and configured to receive the force transfer member 424. The force transfer member 424 can be made of any suitable biocompatible material having a hardness greater than the cancellous spacer body 412. For instance, the force transfer member 424 can be made of cortical bone, titanium, steel, PEEK, a polymer, ceramics, chronOs, CoCr (or other implantable metals), ultra high molecular weight polyethylene (UHMWPE), poly ether ether ketone (PEKK), Carbon-fiber reinforced poly ether ether ketone (PEEK), other suitable implantable polymers, or the like. When the force transfer member 424 is disposed in the channel 418, the force transfer member 424 can secure the cortical spacer body 410 to the cancellous spacer body 412.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

What is claimed:

1. An intervertebral implant system comprising:
  an intervertebral implant configured to be inserted into an intervertebral space, the intervertebral implant including:
    i. a spacer including a cortical spacer body and a cancellous spacer body; and
    ii. a frame including 1) a support member configured to extend along a portion of the cancellous spacer body, such that the cancellous spacer body is disposed between the support member and at least a portion of the cortical spacer body, and 2) first and second frame arms that extend out from the support member and are configured to engage the spacer; and an expansion instrument configured to expand the intervertebral implant frame to receive the spacer, the expansion instrument including:
  i. a first member defining a first base and a first instrument arm that extends from the first base and is configured to releasably couple to the first frame arm; and
  ii. a second member defining a second base and a second instrument arm that extends from the second base and is configured to releasably couple to the second frame arm, wherein the second base is configured to be received by the first member,
  wherein the first and second members are configured to cause the first and second frame arms to move away from each other, and
  wherein the first and second bases are pivotable with respect to each other about a translatable pivot location.

2. The intervertebral implant system of claim 1, wherein the first member defines a first gap that extends into the first base, and the second base is translatable relative to the first base in the first gap so as to cause the respective first and second instrument arms to move away from each other.

3. The intervertebral implant system of claim 1, wherein the frame defines at least one fixation element receiving aperture that extends through the support member, such that a fixation element inserted through the at least one fixation element receiving aperture toward the spacer travels from the support member and through the cancellous spacer body without passing through any of the cortical spacer body.

4. The intervertebral implant as recited in claim 3, wherein the frame defines four fixation element receiving apertures that extend through the support member, such that four fixation elements that are inserted through respective ones of the four fixation element receiving apertures and pass entirely through the spacer travel through the cancellous bone graft material without passing through any of the cortical spacer body.

5. The intervertebral implant system as recited in claim 4, wherein 1) the spacer defines a top surface that extends from a proximal end surface of the spacer to a distal end surface of the spacer, and a bottom surface opposite the top surface, the bottom surface extending from the proximal end surface to the distal end surface, 2) each of the fixation elements create a respective channel in the cancellous spacer body after it extends through the at least one fixation element receiving aperture, and 3) each of the channels defines a respective first opening in the proximal end surface and a respective second opening in the top surface.

6. The intervertebral implant as recited in claim 5, wherein the first opening is completely encircled by the proximal end surface.

7. The intervertebral implant as recited in claim 5, wherein the at least one channel is open at an intersection of the proximal end surface and the top surface.

8. The intervertebral implant as recited in claim 5, wherein the at least one channel is open at an intersection of the proximal end surface and the bottom surface.

9. The intervertebral implant system of claim 1, wherein the spacer defines a proximal end that comprises the cancellous spacer body and none of the cortical spacer body, and a distal end that is spaced from the proximal end in a distal direction, the distal end comprising the cortical spacer body and none of the cancellous spacer body.

10. The intervertebral implant system of claim 1, wherein the first and second frame arms are configured to engage the cortical spacer body so as to retain the spacer with respect to the frame.

11. The intervertebral implant system of claim 1, wherein the first member defines a first gap that receives the second base, wherein at least a portion of the first gap extends into the first base but not through the first base so as to terminate at a first stop wall, and the second base is translatable relative to the first base in the first gap so as to increase a distance between the first and second instrument arms until the second base contacts the first stop wall.

12. The intervertebral implant system of claim 11, wherein the second member defines a second gap that extends into the second base, and the first member is configured to be received in the second gap.

13. The intervertebral implant system of claim 12, wherein 1) at least a portion of the second gap extends into the second base but not through the second base so as to terminate at a second stop wall, 2) the first base is translatable relative to the first base in the second gap so as to move the second instrument arm away from the first instrument arm until the first base contacts the second stop wall, and 3) the first base is translatable relative to the second base in the second gap so as to move the first instrument arm away from the second instrument arm until the first base contacts the second stop wall.

14. The intervertebral implant system of claim 13, wherein the first and second members define respective first and second handle portions that are movable toward each other so as to cause the first and second bases to translate within the second and first gaps, respectively, thereby moving the first and second instrument arms away from each other.

15. The intervertebral implant system of claim 1, wherein the first and second instrument arms comprise respective first and second engagement members that, in turn, define first and second dovetailed gripping portions, respectively, that are configured to releaseably couple the expansion instrument to the first and second frame arms, respectively.

16. The intervertebral implant system of claim 1, wherein the first and second instrument arms are configured to elastically deflect the first and second frame arms away from each other a sufficient distance such that the frame receives the spacer, and the first and second frame arms are configured to flex elastically so as to subsequently apply a retention force to the intervertebral spacer that retains the spacer in the frame.

17. The intervertebral implant system as recited in claim 1, wherein the cortical spacer body defines at least one groove sized to receive first and second retention members of the first and second frame arms, respectively.

18. The intervertebral implant system as recited in claim 1, wherein the spacer defines a proximal end surface that comprises the cancellous spacer body, and a distal end surface that defines the cortical spacer body, and wherein the distal end has a respective width, the proximal end has a respective width, and the respective width of the distal end is less than the respective width of the proximal end.

* * * * *